United States Patent
Rabuka et al.

(10) Patent No.: US 9,879,249 B2
(45) Date of Patent: Jan. 30, 2018

(54) ALDEHYDE-TAGGED PROTEIN-BASED DRUG CARRIERS AND METHODS OF USE

(71) Applicant: Redwood Bioscience, Inc., Burlingame, CA (US)

(72) Inventors: David Rabuka, Kensington, CA (US); Mark Alan Breidenbach, New York, NY (US)

(73) Assignee: Redwood Bioscience, Inc., Emeryville, CA (US)

( * ) Notice: Subject to any disclaimer, the term of this patent is extended or adjusted under 35 U.S.C. 154(b) by 172 days.

(21) Appl. No.: 14/959,360

(22) Filed: Dec. 4, 2015

(65) Prior Publication Data

US 2016/0160206 A1    Jun. 9, 2016

Related U.S. Application Data

(63) Continuation of application No. 12/706,679, filed on Feb. 16, 2010, now Pat. No. 9,238,878.

(60) Provisional application No. 61/153,162, filed on Feb. 17, 2009.

(51) Int. Cl.

| | | |
|---|---|---|
| *C12N 9/96* | (2006.01) | |
| *A61K 38/23* | (2006.01) | |
| *C12N 9/16* | (2006.01) | |
| *C40B 40/10* | (2006.01) | |
| *A61K 38/26* | (2006.01) | |
| *A61K 47/48* | (2006.01) | |

(52) U.S. Cl.
CPC ............... *C12N 9/96* (2013.01); *A61K 38/23* (2013.01); *A61K 38/26* (2013.01); *A61K 47/48284* (2013.01); *C12N 9/16* (2013.01); *C40B 40/10* (2013.01); *C12Y 301/06* (2013.01)

(58) Field of Classification Search
CPC . C12N 9/96; C12N 9/16; A61K 38/26; A61K 47/48284; A61K 38/23; C40B 40/10
See application file for complete search history.

(56) References Cited

U.S. PATENT DOCUMENTS

| | | |
|---|---|---|
| 4,332,717 A | 6/1982 | Kanaoka et al. |
| 4,342,832 A | 8/1982 | Goeddel et al. |
| 4,671,958 A | 6/1987 | Rodwell et al. |
| 4,952,394 A | 8/1990 | Senter |
| 5,204,449 A | 4/1993 | Puri |

(Continued)

FOREIGN PATENT DOCUMENTS

| | | |
|---|---|---|
| WO | WO 1990004413 | 5/1990 |
| WO | WO 1993012812 | 7/1993 |

(Continued)

OTHER PUBLICATIONS

Baenziger (2003) "A major step on the road to understanding a unique posttranslational modification and its role in a genetic disease" *Cell* 113(4):421-422.

(Continued)

*Primary Examiner* — Alexander D Kim
(74) *Attorney, Agent, or Firm* — Rudy J. Ng; Carol L. Francis; Bozicevic, Field & Francis LLP

(57) ABSTRACT

The disclosure provides aldehyde-tagged protein carriers that can be covalently and site-specifically bound to drug to provide a drug-containing scaffold. The invention also encompasses methods of production of such drug-containing scaffolds and intermediates, as well as methods of use.

26 Claims, 16 Drawing Sheets

(56) References Cited

U.S. PATENT DOCUMENTS

| | | |
|---|---|---|
| 5,208,020 A | 5/1993 | Chari et al. |
| 5,416,064 A | 5/1995 | Cheri et al. |
| 5,428,130 A | 6/1995 | Capon et al. |
| 5,455,165 A | 10/1995 | Capon et al. |
| 5,475,092 A | 12/1995 | Chari et al. |
| 5,484,892 A | 1/1996 | Tedder et al. |
| 5,514,582 A | 5/1996 | Capon et al. |
| 5,585,499 A | 12/1996 | Chari et al. |
| 5,624,821 A | 4/1997 | Winter et al. |
| 5,681,566 A | 10/1997 | Stevenson |
| 5,686,072 A | 11/1997 | Uhr et al. |
| 5,698,672 A | 12/1997 | Labroo et al. |
| 5,789,554 A | 8/1998 | Leung et al. |
| 5,831,000 A | 11/1998 | Murayama et al. |
| 5,846,545 A | 12/1998 | Chari et al. |
| 5,885,573 A | 3/1999 | Bluestone et al. |
| 5,980,895 A | 11/1999 | Pastan et al. |
| 5,981,485 A | 11/1999 | O'Connor et al. |
| 5,981,488 A | 11/1999 | Hoffman |
| 6,103,236 A | 8/2000 | Suzawa et al. |
| 6,121,022 A | 9/2000 | Presta et al. |
| 6,183,744 B1 | 2/2001 | Goldenberg |
| 6,187,287 B1 | 2/2001 | Leung et al. |
| 6,194,551 B1 | 2/2001 | Idusogie et al. |
| 6,254,868 B1 | 7/2001 | Leung et al. |
| 6,268,343 B1 | 7/2001 | Knudsen et al. |
| 6,284,727 B1 | 9/2001 | Kim et al. |
| 6,395,226 B1 | 5/2002 | Plunkett |
| 6,441,163 B1 | 8/2002 | Chari et al. |
| 6,528,624 B1 | 3/2003 | Idusogie et al. |
| 6,538,124 B1 | 3/2003 | Idusogie et al. |
| 6,548,644 B1 | 4/2003 | Pettit |
| 6,570,040 B2 | 5/2003 | Saxon et al. |
| 6,576,744 B1 | 6/2003 | Presnell et al. |
| 6,608,183 B1 | 8/2003 | Cox, III |
| 6,608,196 B2 | 8/2003 | Wang et al. |
| 6,653,104 B2 | 11/2003 | Goldenberg |
| 6,660,843 B1 | 12/2003 | Feige et al. |
| 6,692,924 B2 | 2/2004 | Presnell et al. |
| 6,710,169 B2 | 3/2004 | Capon et al. |
| 6,716,821 B2 | 4/2004 | Zhao et al. |
| 6,737,056 B1 | 5/2004 | Presta |
| 6,756,480 B2 | 6/2004 | Kostenuik et al. |
| 6,770,625 B2 | 8/2004 | Soltero et al. |
| 6,777,539 B2 | 8/2004 | Sprecher et al. |
| 6,800,740 B1 | 10/2004 | Cunningham et al. |
| 6,803,451 B2 | 10/2004 | Presnell et al. |
| 6,825,166 B2 | 11/2004 | McChesney et al. |
| 6,875,845 B2 | 4/2005 | Presnell et al. |
| 6,884,869 B2 | 4/2005 | Senter et al. |
| 6,897,044 B1 | 5/2005 | Braslawsky et al. |
| 6,897,292 B2 | 5/2005 | Presnell et al. |
| 6,900,218 B2 | 5/2005 | Wang et al. |
| 6,913,748 B2 | 7/2005 | Widdison |
| 6,927,042 B2 | 8/2005 | Schultz et al. |
| 6,989,366 B2 | 1/2006 | Beeley et al. |
| 6,989,452 B2 | 1/2006 | Ng et al. |
| 6,998,253 B1 | 2/2006 | Presta et al. |
| 7,045,337 B2 | 5/2006 | Schultz et al. |
| 7,045,498 B2 | 5/2006 | Kindsvogel et al. |
| 7,045,605 B2 | 5/2006 | Bader et al. |
| 7,049,316 B2 | 5/2006 | Zhao et al. |
| 7,056,701 B2 | 6/2006 | Fleer et al. |
| 7,087,600 B2 | 8/2006 | Ng et al. |
| 7,091,186 B2 | 8/2006 | Senter et al. |
| 7,097,840 B2 | 8/2006 | Erickson et al. |
| 7,098,308 B2 | 8/2006 | Senter et al. |
| 7,112,439 B2 | 9/2006 | Johnson et al. |
| 7,115,573 B2 | 10/2006 | Pickford et al. |
| 7,122,637 B2 | 10/2006 | Presta |
| 7,138,371 B2 | 11/2006 | DeFrees |
| 7,141,547 B2 | 11/2006 | Rosen et al. |
| 7,176,278 B2 | 2/2007 | Prior |
| 7,183,387 B1 | 2/2007 | Presta |
| 7,189,811 B2 | 3/2007 | Panda et al. |
| 7,189,835 B2 | 3/2007 | Raymond et al. |
| 7,189,839 B2 | 3/2007 | Presnell et al. |
| 7,214,663 B2 | 5/2007 | Bebbington et al. |
| 7,214,685 B2 | 5/2007 | Tietze et al. |
| 7,226,990 B2 | 6/2007 | Knudsen et al. |
| 7,230,068 B2 | 6/2007 | Wilson |
| 7,255,012 B2 | 8/2007 | Hedtke |
| 7,256,257 B2 | 8/2007 | Doronina et al. |
| 7,265,203 B2 | 9/2007 | Presnell et al. |
| 7,271,149 B2 | 9/2007 | Glaesner et al. |
| 7,271,255 B2 | 9/2007 | Raymond et al. |
| 7,276,497 B2 | 10/2007 | Chari et al. |
| 7,276,585 B2 | 10/2007 | Lazar et al. |
| 7,276,947 B2 | 10/2007 | Becker et al. |
| 7,297,775 B2 | 11/2007 | Idusogie et al. |
| 7,317,091 B2 | 1/2008 | Lazar et al. |
| 7,321,026 B2 | 1/2008 | Leung |
| 7,332,571 B2 | 2/2008 | Miao et al. |
| 7,332,581 B2 | 2/2008 | Presta |
| 7,335,742 B2 | 2/2008 | Presta |
| 7,338,659 B2 | 3/2008 | Leung |
| 7,351,555 B2 | 4/2008 | Presnell et al. |
| 7,355,008 B2 | 4/2008 | Stavenhagen et al. |
| 7,355,011 B2 | 4/2008 | Popplewell et al. |
| 7,355,012 B2 | 4/2008 | Pastan et al. |
| 7,361,347 B2 | 4/2008 | Adolf et al. |
| 7,368,565 B2 | 5/2008 | Chari et al. |
| 7,371,826 B2 | 5/2008 | Presta |
| 7,374,762 B2 | 5/2008 | Amphlett |
| 7,381,408 B2 | 6/2008 | Mezo et al. |
| 7,385,028 B2 | 6/2008 | Miao et al. |
| 7,388,026 B2 | 6/2008 | Zhao et al. |
| 7,404,956 B2 | 7/2008 | Peters et al. |
| 7,364,731 B2 | 8/2008 | Idusogie et al. |
| 7,410,779 B2 | 8/2008 | Fleer et al. |
| 7,411,056 B2 | 8/2008 | Presnell et al. |
| 7,416,727 B2 | 8/2008 | Presta |
| 7,423,116 B2 | 9/2008 | Doronina et al. |
| 7,425,541 B2 | 9/2008 | Dubois et al. |
| 7,435,416 B2 | 10/2008 | Devaux et al. |
| 7,435,550 B2 | 10/2008 | Novak et al. |
| 7,442,778 B2 | 10/2008 | Gegg et al. |
| 7,445,764 B1 | 11/2008 | Kratz |
| 7,456,260 B2 | 11/2008 | Rybak et al. |
| 7,473,796 B2 | 1/2009 | Chari et al. |
| 7,488,590 B2 | 2/2009 | Feige et al. |
| 7,491,809 B2 | 2/2009 | Presnell et al. |
| 7,494,649 B2 | 2/2009 | Amphlett et al. |
| 7,498,298 B2 | 3/2009 | Doronina et al. |
| 7,498,302 B2 | 3/2009 | Ng et al. |
| 7,501,120 B2 | 3/2009 | Amphlett et al. |
| 7,501,497 B2 | 3/2009 | Rixon et al. |
| 7,507,420 B2 | 3/2009 | Ng et al. |
| 7,514,080 B2 | 4/2009 | Amphlett et al. |
| 7,517,903 B2 | 4/2009 | Chen et al. |
| 7,521,541 B2 | 4/2009 | Eigenbrot et al. |
| 7,521,542 B2 | 4/2009 | Johnson et al. |
| 7,534,427 B2 | 5/2009 | Goldenberg et al. |
| 7,541,034 B1 | 6/2009 | Fitzgerald et al. |
| 7,553,816 B2 | 6/2009 | Senter et al. |
| 7,572,456 B2 | 8/2009 | Johnson et al. |
| 7,572,892 B2 | 8/2009 | Novak et al. |
| 7,575,748 B1 | 8/2009 | Erickson et al. |
| 7,601,354 B2 | 10/2009 | Chari |
| 7,608,686 B2 | 10/2009 | Gross et al. |
| 7,618,628 B2 | 11/2009 | Johnson et al. |
| 7,622,116 B2 | 11/2009 | Kuestner et al. |
| 7,629,452 B2 | 12/2009 | Sprecher et al. |
| 7,632,497 B2 | 12/2009 | Stavenhagen |
| 7,635,767 B2 | 12/2009 | Rixon et al. |
| 7,642,228 B2 | 1/2010 | Carter et al. |
| 7,655,660 B2 | 2/2010 | Zhao et al. |
| 7,655,661 B2 | 2/2010 | Zhao et al. |
| 7,657,380 B2 | 2/2010 | Lazar et al. |
| 7,659,241 B2 | 2/2010 | Senter et al. |
| 7,662,387 B2 | 2/2010 | Law et al. |
| 7,662,925 B2 | 2/2010 | Lazar et al. |
| 7,662,936 B2 | 2/2010 | Kadkhodayan et al. |
| 7,691,962 B2 | 4/2010 | Boyd et al. |

(56) References Cited

U.S. PATENT DOCUMENTS

| | | |
|---|---|---|
| 7,722,865 B2 | 5/2010 | Vellard et al. |
| 7,723,485 B2 | 5/2010 | Junutula et al. |
| 7,745,394 B2 | 6/2010 | Doronina et al. |
| 7,750,116 B1 | 7/2010 | Doronina et al. |
| 7,754,681 B2 | 7/2010 | Feng |
| 7,771,727 B2 | 8/2010 | Fuselier et al. |
| 7,777,019 B2 | 8/2010 | Pastan et al. |
| 7,803,915 B2 | 9/2010 | Cairns et al. |
| 7,816,317 B2 | 10/2010 | Bebbington et al. |
| 7,829,086 B2 | 11/2010 | Hilbert et al. |
| 7,829,531 B2 | 11/2010 | Senter et al. |
| 7,837,980 B2 | 11/2010 | Alley et al. |
| 7,847,105 B2 | 12/2010 | Gangwar et al. |
| 7,851,432 B2 | 12/2010 | Chari et al. |
| 7,851,437 B2 | 12/2010 | Senter et al. |
| 7,855,275 B2 | 12/2010 | Eigenbrot et al. |
| 7,858,759 B2 | 12/2010 | Brandt et al. |
| 7,893,023 B2 | 2/2011 | Tronet et al. |
| 7,906,545 B2 | 3/2011 | Zhao et al. |
| 7,960,512 B2 | 6/2011 | Stavenhagen et al. |
| 7,964,195 B2 | 6/2011 | Papkoff et al. |
| 7,964,566 B2 | 6/2011 | Doronina et al. |
| 7,964,567 B2 | 6/2011 | Doronina et al. |
| 7,978,319 B2 | 7/2011 | Okabe et al. |
| 8,163,882 B2 | 4/2012 | Presta |
| 8,192,737 B2 | 6/2012 | Stavenhagen et al. |
| 2002/0103345 A1 | 8/2002 | Zhu |
| 2002/0128448 A1 | 9/2002 | Reff |
| 2002/0146504 A1 | 10/2002 | Schwartz |
| 2002/0177756 A1 | 11/2002 | Pierre Godinot et al. |
| 2003/0082575 A1 | 5/2003 | Schultz et al. |
| 2003/0108609 A1 | 6/2003 | Berry et al. |
| 2003/0109682 A1 | 6/2003 | Santi et al. |
| 2003/0124669 A1 | 7/2003 | Pan et al. |
| 2003/0157108 A1 | 8/2003 | Presta |
| 2003/0166868 A1 | 9/2003 | Presta et al. |
| 2003/0171285 A1 | 9/2003 | Finn et al. |
| 2004/0010124 A1 | 1/2004 | Johnson et al. |
| 2004/0048395 A1 | 3/2004 | Lee et al. |
| 2004/0110226 A1 | 6/2004 | Lazar et al. |
| 2004/0115774 A1 | 6/2004 | Kochendorfer et al. |
| 2004/0132101 A1 | 7/2004 | Lazar et al. |
| 2004/0197866 A1 | 10/2004 | Johnson et al. |
| 2004/0219156 A1 | 11/2004 | Goldenberg et al. |
| 2004/0229250 A1 | 11/2004 | Figura et al. |
| 2004/0265952 A1 | 12/2004 | Deiters et al. |
| 2005/0037000 A1 | 2/2005 | Stavenhagen et al. |
| 2005/0064514 A1 | 3/2005 | Stavenhagen et al. |
| 2005/0084862 A1 | 4/2005 | Lee et al. |
| 2005/0118174 A1 | 6/2005 | Presta |
| 2005/0118182 A1 | 6/2005 | Pastan et al. |
| 2005/0142133 A1 | 6/2005 | Lazar |
| 2005/0147618 A1 | 7/2005 | Rivera et al. |
| 2005/0170404 A1 | 8/2005 | Cho et al. |
| 2005/0177878 A1 | 8/2005 | Melo et al. |
| 2005/0220762 A1 | 10/2005 | Cho et al. |
| 2005/0249723 A1 | 11/2005 | Lazar |
| 2005/0260711 A1 | 11/2005 | Datta et al. |
| 2005/0281829 A1 | 12/2005 | Hehir et al. |
| 2006/0013810 A1 | 1/2006 | Johnson et al. |
| 2006/0014212 A1 | 1/2006 | Benkovic et al. |
| 2006/0019347 A1 | 1/2006 | Cho et al. |
| 2006/0024298 A1 | 2/2006 | Lazar et al. |
| 2006/0035305 A1 | 2/2006 | Bertozzi |
| 2006/0057149 A1 | 3/2006 | Johnson et al. |
| 2006/0121032 A1 | 6/2006 | Dahiyat et al. |
| 2006/0134105 A1 | 6/2006 | Lazar et al. |
| 2006/0134709 A1 | 6/2006 | Stavenhagen et al. |
| 2006/0135427 A1 | 6/2006 | Hays et al. |
| 2006/0153860 A1 | 7/2006 | Cho et al. |
| 2006/0173170 A1 | 8/2006 | Chamberlain et al. |
| 2006/0182750 A1 | 8/2006 | Chari et al. |
| 2006/0183198 A1 | 8/2006 | Buechler et al. |
| 2006/0189529 A1 | 8/2006 | Cho et al. |
| 2006/0194290 A1 | 8/2006 | Presta |
| 2006/0194957 A1 | 8/2006 | Presta |
| 2006/0217289 A1 | 9/2006 | Miao et al. |
| 2006/0235208 A1 | 10/2006 | Lazar et al. |
| 2006/0275254 A1 | 12/2006 | Kim et al. |
| 2007/0004909 A1 | 1/2007 | Johnson et al. |
| 2007/0009523 A1 | 1/2007 | Presta |
| 2007/0020258 A1 | 1/2007 | Jardieu et al. |
| 2007/0020260 A1 | 1/2007 | Presta |
| 2007/0024389 A1 | 2/2007 | Mizutani |
| 2007/0031922 A1 | 2/2007 | Presta et al. |
| 2007/0036799 A1 | 2/2007 | Stavenhagen et al. |
| 2007/0037216 A1 | 2/2007 | Johnson et al. |
| 2007/0053901 A1 | 3/2007 | Lazar et al. |
| 2007/0077429 A1 | 4/2007 | Mirkin et al. |
| 2007/0122408 A1 | 5/2007 | Barbas, III |
| 2007/0123691 A1 | 5/2007 | Wilson |
| 2007/0123693 A1 | 5/2007 | Wilson |
| 2007/0135620 A1 | 6/2007 | Chamberlain et al. |
| 2007/0148170 A1 | 6/2007 | Desjarlais et al. |
| 2007/0148171 A1 | 6/2007 | Lazar et al. |
| 2007/0160597 A1 | 7/2007 | Lazar et al. |
| 2007/0166309 A1 | 7/2007 | Lazar et al. |
| 2007/0189962 A1 | 8/2007 | Pastan et al. |
| 2007/0198996 A1 | 8/2007 | Chiu et al. |
| 2007/0202098 A1 | 8/2007 | Lazar et al. |
| 2007/0219133 A1 | 9/2007 | Lazar et al. |
| 2007/0224189 A1 | 9/2007 | Lazar et al. |
| 2007/0224192 A1 | 9/2007 | Lazar et al. |
| 2007/0231329 A1 | 10/2007 | Lazar et al. |
| 2007/0237765 A1 | 10/2007 | Lazar et al. |
| 2007/0237766 A1 | 10/2007 | Lazar et al. |
| 2007/0237767 A1 | 10/2007 | Lazar et al. |
| 2007/0238665 A1 | 10/2007 | Lazar et al. |
| 2007/0243188 A1 | 10/2007 | Lazar et al. |
| 2007/0244303 A1 | 10/2007 | Johnson et al. |
| 2007/0248602 A1 | 10/2007 | Lazar et al. |
| 2007/0248603 A1 | 10/2007 | Lazar et al. |
| 2007/0264260 A1 | 11/2007 | Tuscano et al. |
| 2007/0269369 A1 | 11/2007 | Gegg et al. |
| 2007/0275460 A1 | 11/2007 | Desjarlais et al. |
| 2007/0286859 A1 | 12/2007 | Lazar et al. |
| 2008/0044417 A1 | 2/2008 | Johnson et al. |
| 2008/0044429 A1 | 2/2008 | Johnson et al. |
| 2008/0050310 A1 | 2/2008 | Ebens et al. |
| 2008/0050371 A1 | 2/2008 | Johnson et al. |
| 2008/0050374 A1 | 2/2008 | Cho et al. |
| 2008/0051563 A1 | 2/2008 | Lazar et al. |
| 2008/0057056 A1 | 3/2008 | Lazar et al. |
| 2008/0081038 A1 | 4/2008 | Cho et al. |
| 2008/0085277 A1 | 4/2008 | Cho et al. |
| 2008/0085538 A1 | 4/2008 | Buechler et al. |
| 2008/0095762 A1 | 4/2008 | Presta |
| 2008/0096819 A1 | 4/2008 | Grabstein et al. |
| 2008/0097083 A1 | 4/2008 | Cho et al. |
| 2008/0102124 A1 | 5/2008 | Cho et al. |
| 2008/0102125 A1 | 5/2008 | Cho et al. |
| 2008/0103293 A1 | 5/2008 | Cho et al. |
| 2008/0103294 A1 | 5/2008 | Cho et al. |
| 2008/0108791 A1 | 5/2008 | Cho et al. |
| 2008/0108792 A1 | 5/2008 | Hays et al. |
| 2008/0108797 A1 | 5/2008 | Cho et al. |
| 2008/0112943 A1 | 5/2008 | Mariani et al. |
| 2008/0112961 A1 | 5/2008 | Stavenhagen et al. |
| 2008/0113408 A1 | 5/2008 | Mariani et al. |
| 2008/0113411 A1 | 5/2008 | Sheffer et al. |
| 2008/0113412 A1 | 5/2008 | Sheffer et al. |
| 2008/0113457 A1 | 5/2008 | Tsay et al. |
| 2008/0113912 A1 | 5/2008 | Hays et al. |
| 2008/0113913 A1 | 5/2008 | Hays et al. |
| 2008/0113914 A1 | 5/2008 | Hays et al. |
| 2008/0114154 A1 | 5/2008 | Cho et al. |
| 2008/0114155 A1 | 5/2008 | Cho et al. |
| 2008/0118505 A1 | 5/2008 | Tedder |
| 2008/0119640 A1 | 5/2008 | Hays et al. |
| 2008/0125574 A1 | 5/2008 | Sheffer et al. |
| 2008/0131435 A1 | 6/2008 | Stavenhagen et al. |
| 2008/0132681 A1 | 6/2008 | Hays et al. |
| 2008/0138338 A1 | 6/2008 | Idusogie et al. |
| 2008/0138344 A1 | 6/2008 | Stavenhagen et al. |

(56) References Cited

U.S. PATENT DOCUMENTS

| | | |
|---|---|---|
| 2008/0138349 A1 | 6/2008 | Stavenhagen et al. |
| 2008/0146781 A1 | 6/2008 | Cho et al. |
| 2008/0152649 A1 | 6/2008 | Chamberlain et al. |
| 2008/0154025 A1 | 6/2008 | Lazar et al. |
| 2008/0161539 A1 | 7/2008 | Cho et al. |
| 2008/0161541 A1 | 7/2008 | Lazar et al. |
| 2008/0167452 A1 | 7/2008 | Maiti et al. |
| 2008/0177027 A1 | 7/2008 | Miao et al. |
| 2008/0177038 A1 | 7/2008 | Miao et al. |
| 2008/0181890 A1 | 7/2008 | Lazar et al. |
| 2008/0182968 A1 | 7/2008 | Lazar et al. |
| 2008/0182969 A1 | 7/2008 | Miao et al. |
| 2008/0187491 A1 | 8/2008 | Miao et al. |
| 2008/0187956 A1 | 8/2008 | Carrico et al. |
| 2008/0194459 A1 | 8/2008 | Miao et al. |
| 2008/0199471 A1 | 8/2008 | Bernett et al. |
| 2008/0199909 A1 | 8/2008 | Buechler et al. |
| 2008/0206242 A1 | 8/2008 | Lawrence et al. |
| 2008/0206853 A1 | 8/2008 | Lee et al. |
| 2008/0206867 A1 | 8/2008 | Desjarlais et al. |
| 2008/0207877 A1 | 8/2008 | Cho et al. |
| 2008/0213840 A1 | 9/2008 | Miao et al. |
| 2008/0219974 A1 | 9/2008 | Bernett et al. |
| 2008/0225287 A1 | 9/2008 | Mirkin et al. |
| 2008/0227205 A1 | 9/2008 | Cho |
| 2008/0242845 A1 | 10/2008 | Lazar et al. |
| 2008/0244222 A1 | 10/2008 | Supalov et al. |
| 2008/0248028 A1 | 10/2008 | Lazar et al. |
| 2008/0249288 A1 | 10/2008 | Mezo et al. |
| 2008/0254027 A1 | 10/2008 | Bernett et al. |
| 2008/0255045 A1 | 10/2008 | Cujec et al. |
| 2008/0260731 A1 | 10/2008 | Bernett et al. |
| 2008/0268518 A1 | 10/2008 | Miao et al. |
| 2008/0268519 A1 | 10/2008 | Miao et al. |
| 2008/0274105 A1 | 11/2008 | Presta |
| 2008/0274108 A1 | 11/2008 | Presta |
| 2008/0274506 A1 | 11/2008 | Presta |
| 2008/0292621 A1 | 11/2008 | Lazar et al. |
| 2008/0317758 A9 | 12/2008 | Presta |
| 2009/0004734 A1 | 1/2009 | Pastan et al. |
| 2009/0005312 A1 | 1/2009 | Hansen et al. |
| 2009/0010920 A1 | 1/2009 | Lazar et al. |
| 2009/0041758 A1 | 2/2009 | Glaser et al. |
| 2009/0041770 A1 | 2/2009 | Chamberlain et al. |
| 2009/0042291 A1 | 2/2009 | Chu et al. |
| 2009/0053211 A9 | 2/2009 | Lazar et al. |
| 2009/0053240 A1 | 2/2009 | Lazar et al. |
| 2009/0060910 A1 | 3/2009 | Johnson et al. |
| 2009/0068175 A1 | 3/2009 | Lazar et al. |
| 2009/0068177 A1 | 3/2009 | Lazar et al. |
| 2009/0081208 A1 | 3/2009 | Lazar et al. |
| 2009/0092599 A1 | 4/2009 | Lazar et al. |
| 2009/0098124 A1 | 4/2009 | Stavehagen et al. |
| 2009/0136485 A1 | 5/2009 | Chu et al. |
| 2009/0142340 A1 | 6/2009 | Lazar et al. |
| 2009/0143246 A1 | 6/2009 | Mirkin et al. |
| 2009/0155587 A1 | 6/2009 | Mirkin et al. |
| 2009/0162353 A1 | 6/2009 | Johnson et al. |
| 2009/0162382 A1 | 6/2009 | Bernett et al. |
| 2009/0163699 A1 | 6/2009 | Chamberlain et al. |
| 2009/0185290 A1 | 7/2009 | Li et al. |
| 2009/0202536 A1 | 8/2009 | Ebens et al. |
| 2009/0202537 A1 | 8/2009 | Johnson et al. |
| 2009/0214526 A1 | 8/2009 | Lazar et al. |
| 2009/0215991 A1 | 8/2009 | Lazar et al. |
| 2009/0281286 A1 | 11/2009 | Gregg et al. |
| 2009/0286964 A1 | 11/2009 | Gregg et al. |
| 2009/0305411 A1 | 12/2009 | FitzGerald et al. |
| 2009/0324593 A1 | 12/2009 | Johnson et al. |
| 2010/0129908 A1 | 5/2010 | Fang et al. |
| 2010/0143368 A1 | 6/2010 | King et al. |
| 2010/0204454 A1 | 8/2010 | Chamberlain et al. |
| 2010/0210543 A1 | 8/2010 | Rabuka et al. |
| 2010/0234571 A1 | 9/2010 | Chamberlain et al. |
| 2010/0234572 A1 | 9/2010 | Chamberlain et al. |
| 2010/0234573 A1 | 9/2010 | Chamberlain et al. |
| 2010/0234574 A1 | 9/2010 | Chamberlain et al. |
| 2010/0234575 A1 | 9/2010 | Chamberlain et al. |
| 2010/0311954 A1 | 12/2010 | Chamberlain et al. |
| 2011/0020344 A1 | 1/2011 | Dimitrov et al. |
| 2011/0065185 A1 | 3/2011 | Pastan et al. |
| 2011/0142859 A1 | 6/2011 | Ebens et al. |
| 2011/0293632 A1 | 12/2011 | Presta |

FOREIGN PATENT DOCUMENTS

| | | |
|---|---|---|
| WO | WO 1994026778 | 11/1994 |
| WO | WO 1996004925 | 2/1996 |
| WO | WO 1999058572 | 11/1999 |
| WO | WO 2000042072 | 7/2000 |
| WO | WO 2001081415 | 1/2001 |
| WO | WO 2001060991 | 8/2001 |
| WO | WO 2003027135 | 4/2003 |
| WO | WO 2003105782 | 12/2003 |
| WO | WO 2004072275 | 8/2004 |
| WO | WO 2004082640 | 9/2004 |
| WO | WO 2004099249 | 11/2004 |
| WO | WO 2005000892 | 1/2005 |
| WO | WO 2005035727 | 4/2005 |
| WO | WO 2005047336 | 5/2005 |
| WO | WO 2005052006 | 6/2005 |
| WO | WO 2005074524 | 8/2005 |
| WO | WO 2005074546 | 8/2005 |
| WO | WO 2005074650 | 8/2005 |
| WO | WO 2006009901 | 1/2006 |
| WO | WO 2006068802 | 6/2006 |
| WO | WO 2006069220 | 6/2006 |
| WO | WO 2006071840 | 7/2006 |
| WO | WO 2006073846 | 7/2006 |
| WO | WO 2006091231 | 8/2006 |
| WO | WO 2006069246 | 9/2006 |
| WO | WO 2006132969 | 12/2006 |
| WO | WO 2006133089 | 12/2006 |
| WO | WO 2007021297 | 2/2007 |
| WO | WO 2007056083 | 5/2007 |
| WO | WO 2007056448 | 5/2007 |
| WO | WO 2007059312 | 5/2007 |
| WO | WO 2007070659 | 6/2007 |
| WO | WO 2007079130 | 7/2007 |
| WO | WO 2007094916 | 8/2007 |
| WO | WO 2007103470 | 9/2007 |
| WO | WO 2007140371 | 12/2007 |
| WO | WO 2008011446 | 1/2008 |
| WO | WO 2008030558 | 3/2008 |
| WO | WO 2008030612 | 3/2008 |
| WO | WO 2008030613 | 3/2008 |
| WO | WO 2008030614 | 3/2008 |
| WO | WO 2008036350 | 3/2008 |
| WO | WO 2008070569 | 6/2008 |
| WO | WO 2008077079 | 6/2008 |
| WO | WO 2008083346 | 7/2008 |
| WO | WO 2008121563 | 10/2008 |
| WO | WO 2008137471 | 11/2008 |
| WO | WO 2009058492 | 5/2009 |
| WO | WO 2009120611 | 10/2009 |
| WO | WO 2010096394 | 8/2010 |

OTHER PUBLICATIONS

Berteau et al. (2006) "A new type of bacterial sulfatase reveals a novel maturation pathway in prokaryotes" *J. Biol. Chem.* 281(32):22464-22470.

Cosma et al. (2003) "The multiple sulfatase deficiency gene encodes an essential and limiting factor for the activity of sulfatases" *Cell* 113(4):445-456.

Cosma et al. (2004) "Molecular and functional analysis of SUMF1 mutations in multiple sulfatase deficiency" *Hum. Mutat.* 23, 576-581.

Dierks et al. (1997) "Conversion of cysteine to formylglycine: a protein modification in the endoplasmic reticulum" *Proc Natl Acad Sci U S A* 94(22):11963-8.

(56) References Cited

OTHER PUBLICATIONS

Dierks et al. (1998) "Conversion of cysteine to formylglycine in eukaryotic sulfatases occurs by a common mechanism in the endoplasmic reticulum" *FEBS Lett.* 423(1):61-5.
Dierks et al. (1999) "Sequence determinants directing conversion of cysteine to formylglycine in eukaryotic sulfatases" *EMBO J* 18(8):2084-2091.
Dierks et al. (2003) "Multiple sulfatase deficiency is caused by mutations in the gene encoding the human Cα-formylglycine generating enzyme" *Cell* 113(4):435-444.
Dierks et al. (2005) "Molecular basis for multiple sulfatase deficiency and mechanism for formylglycine generation of the human formylglycine-generating enzyme" *Cell.* 121(4):541-552.
Fang et al. (2004) "Post-translational formylglycine modification of bacterial sulfatases by the radical S-adenosylmethionine protein AtsB" *J Biol Chem.* 79(15):14570-8.
GenBank Accession No. NM_182760 "*Homo sapiens* sulfatase modifying factor 1 (SUMF1), transcript variant 1, mRNA" dated Nov. 28, 2012.
Jefferis & Lefranc (2009) "Human Immunoglobulin Allotypes" *MAbs* 1(4):332-338.
Landgrebe et al. (2003) "The human SUMF1 gene, required for posttranslational sulfatase modification, defines a new gene family which is conserved from pro- to eukaryotes" *Gene.* 316:47-56.
Preusser-Kunze et al. (2005) "Molecular characterization of the human Cα-formylglycine-generating enzyme" *J. Biol. Chem.* 280(15):14900-10.
Roeser et al. (2006) "A general binding mechanism for all human sulfatases by the formylglycine-generating enzyme" *Proc Natl Acad Sci USA* 103(1):81-86.
Sardiello et al. (2005) "Sulfatases and sulfatase modifying factors: an exclusive and promiscuous relationship" *Hum Mol Genet.* 14(21):3203-3217.
Szameit et al. (1999) "The iron sulfur protein AtsB is required for posttranslational formation of formylglycine in the *Klebsiella* sulfatase" *J Biol Chem* 274(22):15375-15381.
Connolly "Analytical molecular surface calculation" *J. Appl. Cryst.* (1983) 16:548-558.
GenBank Accession No. AAG00909 "recombinant IgG1 heavy chain [*Homo sapiens*]" dated May 11, 2001.
Kabsch & Sander (1983) "Dictionary of protein secondary structure: pattern recognition of hydrogen-bonded and geometrical features" *Biopolymers* 22: 2577-637.
Lee & Richards (1971) "The interpretation of protein structures: estimation of static accessibility" *J. Mol. Biol.* 55(3):379-400.
Mahal et al. (1997) "Engineering chemical reactivity on cell surfaces through oligosaccharide biosynthesis" *Science* 276(5315):1125-1128.
Adams, et al. (2003) "Safety and Utilization of Blood Components as Therapeutic Delivery Systems" *Curr Pharm Biotechnol* 4(5):275-282.
Andreotti, et al. (2006) "Structural determinants of salmon calcitonin bioactivity: the role of the Leu-based amphipathic α-helix" *J. Biol. Chem.* 281(34):24193-24203.
Baggio, et al. (2008) "An albumin-exendin-4 conjugate engages central and peripheral circuits regulating murine energy and glucose homeostasis" *Gastroenterology* 134(4):1137-1147.
Baker (2002) "Albumin, steroid hormones and the origin of vertebrates" *J Endocrinol* 175(1):121-127.
Brubaker (2007) "Incretin-based therapies: mimetics versus protease inhibitors" *TRENDS Endoccrinol. Metab.*18(6):240-245.
Carter & Senter (2008) "Antibody-Drug Conjugates for Cancer Therapy" *Cancer J* 14(3):154-619.
Doronina, et al. (2008) "Novel peptide linkers for highly potent antibody-auristatin conjugate" *Bioconjugate Chem* 19(10):1960-1963.
Dou, et al. (2008) "Expression, purification, and characterization of recombinant human serum albumin fusion protein with two human glucagon-like peptide-1 mutants in *Pichia pastoris*" *Protein Expr Purif* 61(1):45-49.

Harohalli, et al. (2002) "Site-directed mutagenesis studies of human serum albumin define tryptophan at amino acid position 214 as the principal site for nitrosation" *J Biomed Sci* 9(1):47-58.
Junutula, et al. (2008) "Site-specific conjugation of a cytotoxic drug to an antibody improves the therapeutic index" *Nat Biotechnol* 26(8):925-932.
Komarova (2003) "Regulation of Osteoclasts by Calcitonin and Amphiphilic Calcitonin Conjugates: Role of Cytosolic Calcium" *Calcif Tissue Int* 73(3):265-273.
Kumar, et al. (2007) "Gene therapy of diabetes using a novel GLP-1/IgG1-Fc fusion construct normalizes glucose levels in db/db mice" *Gene Ther.* 14(2):162-172.
Léger, et al. (2004) "Identification of CJC-1131-albumin bioconjugate as a stable and bioactive GLP-1(7-36) analog" *Bioorg. Med. Chem. Lett.* 14(17):4395-4398.
Matthews, (2008) et al. "Pharmacodynamics, Pharmacokinetics, Safety, and Tolerability of Albiglutide, a Long-Acting Glucagon-Like Peptide-1 Mimetic, in Patients with Type 2 Diabetes" *J. Clin. Endocrinol. Metab.* 93(12):4810-4817.
McDonagh, et al. (2006) "Engineered antibody-drug conjugates with defined sites and stoichiometries of drug attachment" *Protein Eng Des Sel* 19(7):299-307.
Müller, et al. (2007) "Improved pharmacokinetics of recombinant bispecific antibody molecules by fusion to human serum albumin" *J Bio Chem* 282(17):12650-12660.
Peterson, et al. (2002) "Probing the structure of the warfarin-binding site on human serum albumin using site-directed mutagenesis" *Proteins* 47(2):116-125.
Picha, et al. (2008) "Protein Engineering Strategies for Sustained Glucagon-Like Peptide-1 Receptor-Dependent Control of Glucose Homeostasis" *Diabetes* 57(7):1926-1934.
Wu & Senter (2005) "Arming antibodies: prospects and challenges for immunoconjugates" *Nat Biotechnol* 23(9):1137-1146.
Youn, et al. (2007) "High-yield production of biologically active mono-PEGylated salmon calcitonin by site-specific PEGylation" *J. Control. Release* 117(3):371-379.
Arslan et al. (1997) "Structurally Modified Firefly Luciferase. Effects of Amino Acid Substitution at Position 286" *J Am Chem Soc* 119(45)10877-10887.
Bain et al. (1989) "Biosynthetic site-specific incorporation of a non-natural amino acid into a polypeptide" *J Am Chem Soc* 111(20):8013-8014.
Boer et al. (2003) "The genome-wide transcriptional responses of *Saccharomyces cerevisiae* grown on glucose in aerobic chemostat cultures limited for carbon, nitrogen, phosphorus, or sulfur" *J Biol Chem* 278(5):3265-3274.
Cornish et al. (1994) "Site-specific incorporation of biophysical probes into proteins" *Proc Natl Acad Sci USA* 91(8):2910-2914.
Cornish et al. (1995) "Probing Protein Structure and Function with an Expanded Genetic Code" *Angew Chem Int Ed Engl* 34:621-633.
Deiters et al. (2003) "Adding amino acids with novel reactivity to the genetic code of *Saccharomyces cerevisiae*" *J Am Chem Soc* 125(39):11782-11783.
Hall et al. (2005) "Contribution of horizontal gene transfer to the evolution of *Saccharomyces cerevisiae*" *Eukaryot Cell* 4(6):1102-1115.
Hecht (1992) "Probing the Synthetic Capabilities of a Center of Biochemical Catalysis" *Acc Chem Res* 25(12):545-552.
Hortin & Boime (1983) "Applications of amino acid analogs for studying co- and posttranslational modifications of proteins" *Meth Enzymol* 96:777-784.
Kirshenbaum et al. (2002) "Biosynthesis of proteins incorporating a versatile set of phenylalanine analogues" *Chembiochem* 3(2-3):235-237.
Takebe (1988) "SR alpha promoter: an efficient and versatile mammalian cDNA expression system composed of the simian virus 40 early promoter and the R-U5 segment of human T-cell leukemia virus type 1 long terminal repeat" *Mol Cell Biol* 8(1):466-472.
Abdel-Magid et al. (2006) "A review on the use of Sodium Triacetoxyborohydride in the Reductive Amination of Ketones and Aldehydes" *Organic Process Research & Development* 10: 971-1031.

(56) References Cited

OTHER PUBLICATIONS

Carrico (2008) "Chemoselective modification of proteins: hitting the target," Chemical Society Reviews, 31: 1423-1431 (Epub Jun. 5, 2008).
Carter et al. (1998) "Humanization of an anti-p185 her2 antibody for human cancer therapy" Proceedings of the National Academy of Sciences U.S.A 89: 4285-4289.
Presta (2008) "Molecular engineering and design of therapeutic antibodies" Current Opinion in Immunology 20: 460-470.
Prescher et al. (2005) "Chemistry in living system," Nature Chemical Biology 1(1):13-21.
Rush et al. (2008) "New Aldehyde Tag Sequences Identified by Screening Formylglycine Generating Enzymes in Vitro and in Vivo." J. Am. Chem. Soc.130: 12240-12241.
Carrico et al (2007) "Introducing genetically encoded aldehydes into proteins" Nature Chemical Biology, 3(6) 321-322.
Smith et al (2014) "Chemenzymatic Fc Glycosylation via Engineered Aldehyde Tags" Bioconjugate Chemistry 25(4): 788-795.
Wu et al. (2009) "Site-specific chemical modification of recombinant proteins produced in mammalian cells by using the benetically encoded aldehyde tag" PNAS 106(9): 300-3005.
Advani et al. (2010) "Safety, pharmacokinetics, and preliminary clinical activity of inotuzumab ozogamicin, a novel immunoconjugate for the treatment of B-cell non-Hodgkin's lymphoma: results of a phase I study" J Clin Oncol 28(12):2085-2093.
Amlot et al. (1993) "A phase I study of an anti-CD22-deglycosylated ricin A chain immunotoxin in the treatment of B-cell lymphomas resistant to conventional therapy" Blood 82(9):2624-2633.
Asai et al. (1999) "Synthesis and antitumor activity of water-soluble duocarmycin B1 prodrugs" Bioorg Med Chem Lett 9(20):2995-2998.
Baird & Holowka (1985) "Structural mapping of Fc receptor bound immunoglobulin E: proximity to the membrane surface of the antibody combining site and another site in the Fab segments" Biochem 24(22):6252-6259.
Boghaert et al. (2008) "Determination of pharmacokinetic values of calicheamicin-antibody conjugates in mice by plasmon resonance analysis of small (5 microl) blood samples" Cancer Chemother Pharmacol 61(6):1027-1035.
Dijoseph et al. (2004) "Antibody-targeted chemotherapy with CMC-544: a CD22-targeted immunoconjugate of calicheamicin for the treatment of B-lymphoid malignancies" Blood 103(5):1807-1814.
Dijoseph et al. (2004) "Potent and specific antitumor efficacy of CMC-544, a CD22-targeted immunoconjugate of calicheamicin, against systemically disseminated B-cell lymphoma" Clin Cancer Res 10:8620-8629.
Dijoseph et al. (2006) "Antitumor efficacy of a combination of CMC-544 (inotuzumab ozogamicin), a CD22-targeted cytotoxic immunoconjugate of calicheamicin, and rituximab against non-Hodgkin's B-cell lymphoma" Clin Cancer Res 12(1):242-249.
Dijoseph et al. (2007) "Therapeutic potential of CD22-specific antibody-targeted chemotherapy using inotuzumab ozogamicin (CMC-544) for the treatment of acute lymphoblastic leukemia" Leukemia 21(11):2240-2245.
Fanslow et al. (1992) "Soluble forms of CD40 inhibit biologic responses of human B cells" J Immunol 149(2):655-660.
Ghetie et al. (1991) "Antitumor activity of Fab' and IgG-anti-CD22 immunotoxins in disseminated human B lymphoma grown in mice with severe combined immunodeficiency disease: effect on tumor cells in extranodal sites" Cancer Res 51(21):5876-5880.
Gilon et al. (1967) "Synthesis of ω-aminooxy acids by oxygen-alkyl fission of lactones: An improved synthesis of DL-canaline" Tetrahedron 23(11):4441-4447.
Idusogie et al. (2000) "Mapping of the C1q binding site on rituxan, a chimeric antibody with a human IgG1 Fc" J Immunol 164(8):4178-4184.

ImmunoGen, Inc. (2008) "ImmunoGen, Inc. Announces Clinical Findings Reported at ASCO with Targeted Anticancer Compounds IMGN242 and AVE1642" http://www.drugs.com/clinical_trials/immunogen-inc-announces-clinical-findings-reported-asco-targeted-anticancer-compounds-imgn242-4545.html#ixzz0r9nPIIXM.
Jeffrey et al. (2005) "Design, synthesis, and in vitro evaluation of dipeptide-based antibody minor groove binder conjugates" J Med Chem 48(5):1344-1358.
Johnson & Wu (2000) "Kabat database and its applications: 30 years after the first variability plot" Nucl Acids Res 28(1):214-218.
Jones et al. (2000) "A convenient synthesis of N-(tert-butyloxycarbonyl)aminooxy ethers" Tetrahedron Lett 41(10):1531-1533.
Kan (2001) "Thioether-bonded constructs of Fab'gamma and Fc gamma modules utilizing differential reduction of interchain disulfide bonds" J Immunol 166(2):1320-1326.
Ogura et al. (2010) "Phase I Study of Inotuzumab Ozogamicin (CMC-544) in Japanese Patients with Follicular Lymphoma Pretreated with Rituximab-Based Therapy" Cancer Sci 101(8):1840-1845. Epub Apr. 23, 2012 doi:10.1111/j. 1349-7006.2010.01601.x.
Passerini Reaction (2012) Wikipedia, available online at http://en.wikipedia.org/wiki/Passerini_reaction.
Pettit (1996) "Progress in the discovery of biosynthetic anticancer drugs" J Nat Prod 59(8):812-821.
Pleass (1999) "Identification of residues in the CH2/CH3 domain interface of IgA essential for interaction with the human fcalpha receptor (FcalphaR) CD89" J Biol Chem 274(33):23508-23514.
Presta (2002) "Engineering therapeutic antibodies for improved function" Biochem Soc Trans 30(4):487-490.
Rakestraw et al. (1990) "Preparation and characterization of immunoconjugates for antibody-targeted photolysis" Bioconjugate Chem 1(3):212-221.
Rutishauser et al. (1968) "Amino Acid Sequence of the Fc Region of a Human γ G-Immunoglobulin" Proc Natl Acad Sci USA 61(4)1414-1421.
Sayers et al. (1998) "Amino acid residues that influence Fc epsilon RI-mediated effector functions of human immunoglobulin E" Biochemistry 37(46):16152-16164.
Shields (2001) "High resolution mapping of the binding site on human IgG1 for Fc gamma RI, Fc gamma RII, Fc gamma RIII, and FcRn and design of IgG1 variants with improved binding to the Fc gamma R" J Biol Chem 276(9):6591-6604.
Singh & Francis (1978) "A direct binding assay for rheumatoid factor serum antiglobulins using fluorescein-labelled Fc fragment of human immunoglobulin-G" J Clin Path 31(10):963-973.
Singh et al. (2008) "Recent Trends in Targeted Anticancer Prodrug and Conjugate Design" Curr Med Chem15(18):1802-1826.
Sondermann & Oosthuizen (2002) "Mediation and Modulation of Antibody Function" Biochem Soc Trans 30(pt.4):481-486.
Stevenson et al. (1997) "Conjugation of human Fc gamma in closed-hinge or open-hinge configuration to Fab'gamma and analogous ligands" J Immunol 158(5):2242-2250.
Stevenson et al. (1999) "Preparation of fcgamma for addition to sulfhydryl-expressing ligands with minimal disturbance of the hinge" J Immunol Meth 231(1-2):169-175.
Stimmel et al. (2000) "Site-specific conjugation on serine → cysteine variant monoclonal antibodies" J Biol Chem 275(39):30445-30450.
Takeshita (2009) "CMC-544 (inotuzumab ozogamicin) shows less effect on multidrug resistant cells: analyses in cell lines and cells from patients with B-cell chronic lymphocytic leukaemia and lymphoma" Br J Haematol 146:34-43.
Taylor (2010) Mutations in an avian IgY-Fc fragment reveal the locations of monocyte Fc receptor binding sites Dev Comp Immunol 34(2):97-101.
Thrasher et al. (1975) "The effect of fluorescein conjugation on Fc-dependent properties of rabbit antibody" J Immunol 114(2 pt. 2):762-764.
Vitetta et al. (1991) "Phase I immunotoxin trial in patients with B-cell lymphoma" Cancer Res 51(15):4052-4058.
Wooley et al. (1993) "Influence of a recombinant human soluble tumor necrosis factor receptor FC fusion protein on type II collagen-induced arthritis in mice" J Immunol 151(11):6602-6607.

(56) References Cited

OTHER PUBLICATIONS

Xu et al. (1999) "Bis(Hydroxamamide)-Based Bifunctional Chelating Agent $^{99m}$Tc Labeling of Polypeptides" *Bioconjug Chem* 10(1):9-17.

Human Serum Albumin (rHSA) carrier protein sequences

Native prepro leader sequence underlined; removed in 2-step process (in humans) before secretion of mature protein:

```
MKWVTFISLL FLFSSAYSRG VFRRDAHKSE VAHRFKDLGE ENFKALVLIA FAQYLQQCPF EDHVKLVNEV
TEFAKTCVAD ESAENCDKSL HTLFGDKLCT VATLRETYGE MADCCAKQEP ERNECFLQHK DDNPNLPRLV
RPEVDVMCTA FHDNEETFLK KYLYEIARRH PYFYAPELLF FAKRYKAAFT ECCQAADKAA CLLPKLDELR
DEGKASSAKQ RLKCASLQKF GERAFKAWAV ARLSQRFPKA EFAEVSKLVT DLTKVHTECC HGDLLECADD
RADLAKYICE NQDSISSKLK ECCEKPLLEK SHCIAEVEND EMPADLPSLA ADFVESKDVC KNYAEAKDVF
LGMFLYEYAR RHPDYSVVLL LRLAKTYETT LEKCCAAADP HECYAKVFDE FKPLVEEPQN LIKQNCELFE
QLGEYKFQNA LLVRYTKKVP QVSTPTLVEV SRNLGKVGSK CCKHPEAKRM PCAEDYLSVV LNQLCVLHEK
TPVSDRVTKC CTESLVNRRP CFSALEVDET YVPKEFNAET FTFHADICTL SEKERQIKKQ TALVELVKHK
PKATKEQLKA VMDDFAAFVE KCCKADDKET CFAEEGKKLV AASQAALGL
```

585 AA in mature protein, MW=66472 Da

Corresponding DNA sequence from human DNA:

```
atgaagtgggtaacctttattccctttcttcttctcttagctcggcttattccaggggtgtgtttcgtcgagatgc
acacaagagtgaggttgctcatcggtttaaagatttgggagaagaaaatttcaaagctttggtgttgattgccttg
ctcagtatcttcagcagtgcagtgtccattgaagatcatgtaaattagtgacaaatgaagtaactgaatttgcaac
gttgctgatgagtcagctgtgaatgctgtgactgattggtgagacaaaattatgcacagttgcaac
tcttcgtgaaaatgtgacaaccctatggtgaatgctgtgtgagaccctgagtgatgtgactgcttcttgcaac
acaaagatgacaaccaacctcccccgattgtacagaagacagggttgatgtgcactgtttcatgacaat
gaagagacattttttgaaaaaatactaagctgtcttttacagaatgttgccaagctgctgataaagctgcctgttgccaagc
ctttgctaaaaagtataaagctgcttttacagaatgttgccaagctgctgataaagctgcctgttgccaaagc
tcgatgaacttcgggatgaaggaagttcgtcgtcagtagtcagagactcaagtgccagtcctcaaaaatttga
gaaagagctttcaaagcttgggatgggcagtagtcgcgagccagagatttcccaaagctgagttgagttgtcagaagtttccaa
```

FIG. 3

N-terminal Aldehyde tag modified rHSA (with prepro leader sequence underlined)

*MKWVTFISLL FLFSSAYSRG VFRRLCTPSR* DAHKSEVAHR FKDLGEENFK ALVLIAFAQY LQQCPFEDHV
KLVNEVTEFA KTCVADESAE NCDKSLHTLF GDKLCTVATL RETYGEMADC CAKQEPERNE CFLQHKDDNP
NLPRLVRPEV DVMCTAFHDN EETFLKKYLY EIARRHPYFY APELLFFAKR YKAAFTECCQ AADKAACLLP
KLDELRDEGK ASSAKQRLKC ASLQKFGERA FKAWAVARLS QRFPKAEFAE VSKLVTDLTK VHTECCHGDL
LECADDRADL AKYICENQDS ISSKLKECCE KPLLEKSHCI AEVENDEMPA DLPSLAADFV ESKDVCKNYA
EAKDVFLGMF LYEYARRHPD YSVVLLRLA KTYETTLEKC CAAADPHECY AKVFDEFKPL VEEPQNLIKQ
NCELFEQLGE YKFQNALLVR YTKKVPQVST PTLVEVSRNL GKVGSKCCKH PEAKRMPCAE DYLSVVLNQL
CVLHEKTPVS DRVTKCCTES LVNRRPCFSA LEVDETYVPK EFNAETFTFH ADICTLSEKE RQIKKQTALV
ELVKHKPKAT KEQLKAVMDD FAAFVEKCCK ADDKETCFAE EGKKLVAASQ AALGL

C-terminal Aldehyde tag modified rHSA

*MKWVTFISLL FLFSSAYSRG VFRRDAHKSE* VAHRFKDLGE ENFKALVLIA FAQYLQQCPF EDHVKLVNEV
TEFAKTCVAD ESAENCDKSL HTLFGDKLCT VATLRETYGE MADCCAKQEP ERNECFLQHK DDNPNLPRLV
RPEVDVMCTA FHDNEETFLK KYLYEIARRH PYFYAPELLF FAKRYKAAFT ECCQAADKAA CLLPKLDELR
DEGKASSAKQ RLKCASLQKF GERAFKAWAV ARLSQRFPKA EFAEVSKLVT DLTKVHTECC HGDLLECADD
RADLAKYICE NQDSISSKLK ECCEKPLLEK SHCIAEVEND EMPADLPSLA ADFVESKDVC KNYAEAKDVF
LGMFLYEYAR RHPDYSVVLL LRLAKTYETT LEKCCAAADP HECYAKVFDE FKPLVEEPQN LIKQNCELFE
QLGEYKFQNA LLVRYTKKVP QVSTPTLVEV SRNLGKVGSK CCKHPEAKRM PCAEDYLSVV LNQLCVLHEK
TPVSDRVTKC CTESLVNRRP CFSALEVDET YVPKEFNAET FTFHADICTL SEKERQIKKQ TALVELVKHK
PKATKEQLKA VMDDFAAFVE KCCKADDKET CFAEEGKKLV AASQAALGLL *CTPSR*

Internal loop Aldehyde tag modified rHSA

*MKWVTFISLL FLFSSAYSRG VFRRDAHKSE* VAHRFKDLGE ENFKALVLIA FAQYLQQCPF EDHVKLVNEV
TEFAKTCVAD ESAENCDKSL HTLFGDKLCT VATLRETYGE MADCCAKQEP ERNECFLQHK DDNPNLPRLV
RPEVDVMCTA FHDNEETFLK KYLYEIARRH PYFYAPELLF FAKRYKAAFT ECCQAADKAA CLLPKLDELR
DEGKASSAKQ RLKCASLQKF GERAFKAWAV ARLSQRFPKA EFAEVSKLVT DLTKVHTECC HGDLLECADD
RADLAKYICE NQDSISSKLK ECCEKPLLEK SHCIAEVEND EMPA*LCTPSR* DLPSLAADFV ESKDVCKNYA
EAKDVFLGMF LYEYARRHPD YSVVLLRLA KTYETTLEKC CAAADPHECY AKVFDEFKPL VEEPQNLIKQ
NCELFEQLGE YKFQNALLVR YTKKVPQVST PTLVEVSRNL GKVGSKCCKH PEAKRMPCAE DYLSVVLNQL
CVLHEKTPVS DRVTKCCTES LVNRRPCFSA LEVDETYVPK EFNAETFTFH ADICTLSEKE RQIKKQTALV
ELVKHKPKAT KEQLKAVMDD FAAFVEKCCK ADDKETCFAE EGKKLVAASQ AALGL

FIG. 4

N-, C- Termini Aldehyde tag modified rHSA

MKWVTFISLL FLFSSAYSRG VFRRLCTPSR DAHKSEVAHR FKDLGEENFK ALVLIAFAQY LQQCPFEDHV
KLVNEVTEFA KTCVADESAE NCDKSLHTLF GDKLCTVATL RETYGEMADC CAKQEPERNE CFLQHKDDNP
NLPRLVRPEV DVMCTAFHDN EETFLKKYLY EIARRHPYFY APELLFFAKR YKAAFTECCQ AADKAACLLP
KLDELRDEGK ASSAKQRLKC ASLQKFGERA FKAWAVARLS QRFPKAEFAE VSKLVTDLTK VHTECCHGDL
LECADDRADL AKYICENQDS ISSKLKECCE KPLLEKSHCI AEVENDEMPA DLPSLAADFV ESKDVCKNYA
EAKDVFLGMF LYEYARRHPD YSVVLLLRLA KTYETTLEKC CAAADPHECY AKVFDEFKPL VEEPQNLIKQ
NCELFEQLGE YKFQNALLVR YTKKVPQVST PTLVEVSRNL GKVGSKCCKH PEAKRMPCAE DYLSVVLNQL
CVLHEKTPVS DRVTKCCTES LVNRRPCFSA LEVDETYVPK EFNAETFTFH ADICTLSEKE RQIKKQTALV
ELVKHKPKAT KEQLKAVMDD FAAFVEKCCK ADDKETCFAE EGKKLVAASQ AALGLLCTPS R

N-, C- Termini, Internal loop Aldehyde tag modified rHSA

MKWVTFISLL FLFSSAYSRG VFRRLCTPSR DAHKSEVAHR FKDLGEENFK ALVLIAFAQY LQQCPFEDHV
KLVNEVTEFA KTCVADESAE NCDKSLHTLF GDKLCTVATL RETYGEMADC CAKQEPERNE CFLQHKDDNP
NLPRLVRPEV DVMCTAFHDN EETFLKKYLY EIARRHPYFY APELLFFAKR YKAAFTECCQ AADKAACLLP
KLDELRDEGK ASSAKQRLKC ASLQKFGERA FKAWAVARLS QRFPKAEFAE VSKLVTDLTK VHTECCHGDL
LECADDRADL AKYICENQDS ISSKLKECCE KPLLEKSHCI AEVENDEMPA LCTPSRDLPS LAADFVESKD
VCKNYAEAKD VFLGMFLYEY ARRHPDYSVV LLLRLAKTYE TTLEKCCAAA DPHECYAKVF DEFKPLVEEP
QNLIKQNCEL FEQLGEYKFQ NALLVRYTKK VPQVSTPTLV EVSRNLGKVG SKCCKHPEAK RMPCAEDYLS
VVLNQLCVLH EKTPVSDRVT KCCTESLVNR RPCFSALEVD ETYVPKEFNA ETFTFHADIC TLSEKERQIK
KQTALVELVK HKPKATKEQL KAVMDDFAAF VEKCCKADDK ETCFAEEGKK LVAASQAALG LLCTPSR

FIG. 4 (Cont.)

DNA Sequences Encoding Exemplary Aldehyde-Tagged rHSA
N-terminal Aldehyde tag modified rHSA
```
atgaaatgggtgacctttattagcctgctgtttctgtttagcagcgcgtatagccgcggc
gtgtttcgccgcctgtgcaccccgagccgcgatgcgcataaaagcgaagtggcgcatcgc
tttaaagatctgggcgaagaaaactttaaagcgctggtgctgattgcgtttgcgcagtat
ctgcagcagtgccgtttgaagatcatgtgaaactggtgaacgaagtgacgaatttgcg
aaaacctgcgtggcggatgaaagcgcggaaaactgcgataaaagcctgcataccctgttt
ggcgataaactgtgcaccgtggcgaccctgcgcgaaacctatggcgaaatggcggattgc
tgcgcgaaacaggaaccggaacgcaacgaatgctttctgcagcataaagatgataacccg
aacctgccgcgcctggtgcgcccggaagtggatgtgatgtgcaccgcgtttcatgataac
gaagaaacctttctgaaaaaatatctgtatgaaattgcgcgccgccatccgtattttat
gcgccggaactgctgttttttgcgaaacgctataaagcggcgtttaccgaatgctgccag
gcggcggataaagcggcgtgcctgctgccgaaactggatgaactgcgcgatgaaggcaaa
gcgagcagcgcgaaacagcgcctgaaatgcgcgagcctgcagaaatttggcgaacgcgcg
tttaaagcgtgggcggtggcgcgcctgagccagcgctttccgaaagcggaatttgcggaa
gtgagcaaactggtgaccgatctgaccaaagtgcataccgaatgctgccatggcgatctg
ctggaatgcgcggatgatcgcgcggatctggcgaaatatatttgcgaaaaccaggatagc
attagcagcaaactgaaagaatgctgcgaaaaaccgctgctggaaaaaagccattgcatt
gcggaagtggaaaacgatgaaatgccggcggatctgccgagcctggcggcggatttgtg
gaaagcaaagatgtgtgcaaaaactatgcggaagcgaaagatgtgtttctgggcatgttt
ctgtatgaatatgcgcgccgccatccggattatagcgtggtgctgctgctgcgcctggcg
aaaacctatgaaaccaccctggaaaaatgctgcgcggcggcggatccgcatgaatgctat
gcgaaagtgtttgatgaatttaaaccgctggtggaagaaccgcagaacctgattaaacag
aactgcgaactgtttgaacagctgggcgaatataaatttcagaacgcgctgctggtgcgc
tataccaaaaaagtgccgcaggtgagcaccccgaccctggtggaagtgagccgcaacctg
ggcaaagtgggcagcaaatgctgcaaacatccggaagcgaaacgcatgccgtgcgcggaa
gattatctgagcgtggtgctgaaccagctgtgcgtgctgcatgaaaaaccccggtgagc
gatcgcgtgaccaaatgctgcaccgaaagcctggtgaaccgccgcccgtgctttagcgcg
ctggaagtggatgaaacctatgtgccgaaagaatttaacgcggaaacctttaccttcat
gcggatatttgcaccctgagcgaaaaagaacgccagattaaaaaacagaccgcgctggtg
gaactggtgaaacataaaccgaaagcgaccaaagaacagctgaaagcggtgatggatgat
tttgcggcgtttgtggaaaaatgctgcaaagcggatgataaagaaacctgctttgcggaa
gaaggcaaaaaactggtggcggcgagccaggcggcgctgggcctg
```

FIG. 5

DNA Sequences Encoding Exemplary Aldehyde-Tagged rHSA

C-terminal Aldehyde tag modified rHSA

```
atgaaatgggtgacctttattagcctgctgtttctgtttagcagcgcgtatagccgcggc
gtgtttcgccgcgatgcgcataaaagcgaagtggcgcatcgctttaaagatctgggcgaa
gaaaactttaaagcgctggtgctgattgcgtttgcgcagtatctgcagcagtgcccgttt
gaagatcatgtgaaactggtgaacgaagtgaccgaatttgcgaaaacctgcgtggcggat
gaaagcgcggaaaactgcgataaaagcctgcataccctgtttggcgataaactgtgcacc
gtggcgaccctgcgcgaaacctatggcgaaatggcggattgctgcgcgaaacaggaaccg
gaacgaacgaatgctttctgcagcataaagatgataacccgaacctgccgcgcctggtg
cgcccggaagtggatgtgatgtgcaccgcgtttcatgataacgaagaaacctttctgaaa
aaatatctgtatgaaattgcgcgccgccatccgtatttttatgcgccggaactgctgttt
tttgcgaaacgctataaagcggcgtttaccgaatgctgccaggcggcggataaagcggcg
tgcctgctgccgaaactggatgaactgcgcgatgaaggcaaagcgagcagcgcgaaacag
cgcctgaaatgcgcgagcctgcagaaatttggcgaacgcgcgtttaaagcgtgggcggtg
gcgcgcctgagccagcgctttccgaaagcggaatttgcggaagtgagcaaactggtgacc
gatctgaccaaagtgcataccgaatgctgccatggcgatctgctggaatgcgcggatgat
cgcgcggatctggcgaaatatatttgcgaaaaccaggatagcattagcagcaaactgaaa
gaatgctgcgaaaaaccgctgctggaaaaaagccattgcattgcggaagtggaaaacgat
gaaatgccggcggatctgccgagcctggcggcggattttgtggaaagcaaagatgtgtgc
aaaaactatgcggaagcgaaagatgtgtttctgggcatgtttctgtatgaatatgcgcgc
cgccatccggattatagcgtggtgctgctgctgcgcctggcgaaaacctatgaaaccacc
ctggaaaaatgctgcgcggcggcggatccgcatgaatgctatgcgaaagtgtttgatgaa
tttaaaccgctggtggaagaaccgcagaacctgattaaacagaactgcgaactgtttgaa
cagctgggcgaatataaatttcagaacgcgctgctggtgcgctataccaaaaaagtgccg
caggtgagcacccgaccctggtggaagtgagccgcaacctgggcaaagtgggcagcaaa
tgctgcaaacatccggaagcgaaacgcatgccgtgcgcggaagattatctgagcgtggtg
ctgaaccagctgtgcgtgctgcatgaaaaaccccggtgagcgatcgcgtgaccaaatgc
tgcaccgaaagcctggtgaaccgccgccgtgctttagcgcgctggaagtggatgaaacc
tatgtgccgaaagaatttaacgcggaaacctttaccttcatgcggatatttgcaccctg
agcgaaaaagaacgccagattaaaaaacagaccgcgctggtggaactggtgaaacataaa
ccgaaagcgaccaaagaacagctgaaagcggtgatggatgattttgcggcgtttgtggaa
aaatgctgcaaagcggatgataaagaacctgctttgcggaagaaggcaaaaaactggtg
gcggcgagccaggcggcgctgggcctgctgtgcaccccgagccgc
```

FIG. 6

DNA Sequences Encoding Exemplary Aldehyde-Tagged rHSA
Internal loop Aldehyde tag modified rHSA atgaaatgggtgacctttattagcctgctgtttctgtttagcagcgcgtatagccgcggc
gtgtttcgccgcgatgcgcataaaagcgaagtggcgcatcgctttaaagatctgggcgaa
gaaaactttaaagcgctggtgctgattgcgtttgcgcagtatctgcagcagtgcccgttt
gaagatcatgtgaaactggtgaacgaagtgaccgaatttgcgaaaacctgcgtggcggat
gaaagcgcggaaaactgcgataaagcctgcataccctgtttggcgataaactgtgcacc
gtggcgaccctgcgcgaaacctatggcgaaatggcggattgctgcgcgaaacaggaaccg
gaacgcaacgaatgctttctgcagcataaagatgataacccgaacctgccgcgcctggtg
cgcccggaagtggatgtgatgtgcaccgcgtttcatgataacgaagaaacctttctgaaa
aaatatctgtatgaaattgcgcgccgccatccgtattttatgcgccggaactgctgttt
tttgcgaaacgctataaagcggcgtttaccgaatgctgccaggcggcggataaagcggcg
tgcctgctgccgaaactggatgaactgcgcgatgaaggcaaagcgagcagcgcgaaacag
cgcctgaaatgcgcgagcctgcagaaatttggcgaacgcgcgtttaaagcgtggcggtg
gcgcgcctgagccagcgcttccgaaagcggaatttgcggaagtgagcaaactggtgacc
gatctgaccaaagtgcataccgaatgctgccatggcgatctgctggaatgcgcggatgat
cgcgcggatctggcgaaatatatttgcgaaaaccaggatagcattagcagcaaactgaaa
gaatgctgcgaaaaaccgctgctggaaaaagccattgcattgcggaagtggaaaacgat
gaaatgccggcgctgtgcaccccgagccgcgatctgccgagcctggcggcggattttgtg
gaaagcaaagatgtgtgcaaaaactatgcggaagcgaaagatgtgtttctgggcatgttt
ctgtatgaatatgcgcgccgccatccggattatagcgtggtgctgctgctgcgcctggcg
aaaacctatgaaaccaccctggaaaaatgctgcgcggcggcggatccgcatgaatgctat
gcgaaagtgtttgatgaatttaaaccgctggtggaagaaccgcagaacctgattaaacag
aactgcgaactgtttgaacagctgggcgaatataaatttcagaacgcgctgctggtgcgc
tataccaaaaaagtgccgcaggtgagcaccccgaccctggtggaagtgagccgcaacctg
ggcaaagtgggcagcaaatgctgcaaacatccggaagcgaaacgcatgccgtgcgcggaa
gattatctgagcgtggtgctgaaccagctgtgcgtgctgcatgaaaaacccggtgagc
gatcgcgtgaccaaatgctgcaccgaaagcctggtgaaccgcgcccgtgctttagcgcg
ctggaagtggatgaaacctatgtgccgaaagaatttaacgcggaaacctttaccttcat
gcggatatttgcaccctgagcgaaaagaacgccagattaaaaacagaccgcgctggtg
gaactggtgaaacataaaccgaaagcgaccaaagaacagctgaaagcggtgatggatgat
tttgcggcgtttgtggaaaaatgctgcaaagcggatgataaagaaacctgctttgcggaa
gaaggcaaaaaactggtggcggcgagccaggcggcgctgggcctg

FIG. 7

DNA Sequences Encoding Exemplary Aldehyde-Tagged rHSA N-, C- Termini Aldehyde tag modified rHSA

```
atgaaatgggtgacctttattagcctgctgtttctgtttagcagcgcgtatagccgcggc
gtgtttcgccgcctgtgcaccccgagccgcgatgcgcataaaagcgaagtggcgcatcgc
tttaaagatctgggcgaagaaactttaaagcgctggtgctgattgcgtttgcgcagtat
ctgcagcagtgcccgtttgaagatcatgtgaaactggtgaacgaagtgaccgaatttgcg
aaaacctgcgtggcggatgaaagcgcggaaaactgcgataaaagcctgcataccctgttt
ggcgataaactgtgcaccgtggcgaccctgcgcgaaacctatggcgaaatggcggattgc
tgcgcgaaacaggaaccggaacgcaacgaatgctttctgcagcataaagatgataaccog
aacctgccgcgcctggtgcgcccggaagtggatgtgatgtgcaccgcgtttcatgataac
gaagaaacctttctgaaaaaatatctgtatgaaattgcgcgccgccatccgtattttat
gcgccggaactgctgttttttgcgaaacgctataaagcggcgtttaccgaatgctgccag
gcggcggataaagcggcgtgcctgctgccgaaactggatgaactgcgcgatgaaggcaaa
gcgagcagcgcgaaacagcgcctgaaatgcgcgagcctgcagaaatttggcgaacgcgcg
tttaaagcgtgggcggtggcgcgcctgagccagcgctttccgaaagcggaatttgcggaa
gtgagcaaactggtgaccgatctgaccaaagtgcataccgaatgctgccatggcgatctg
ctggaatgcgcggatgatcgcgcggatctggcgaaatatatttgcgaaaaccaggatagc
attagcagcaaactgaaagaatgctgcgaaaaaccgctgctggaaaaagccattgcatt
gcggaagtggaaaacgatgaaatgccggcggatctgccgagcctggcggcggatttgtg
gaaagcaaagatgtgtgcaaaaactatgcggaagcgaaagatgtgtttctgggcatgttt
ctgtatgaatatgcgcgccgccatccggattatagcgtggtgctgctgctgcgcctggcg
aaaacctatgaaaccaccctggaaaaatgctgcgcggcggcggatccgcatgaatgctat
gcgaaagtgtttgatgaatttaaaccgctggtggaagaaccgcagaacctgattaaacag
aactgcgaactgtttgaacagctgggcgaatataaatttcagaacgcgctgctggtgcgc
tataccaaaaaagtgccgcaggtgagcaccccgaccctggtggaagtgagccgcaacctg
ggcaaagtgggcagcaaatgctgcaaacatccggaagcgaaacgcatgccgtgcgcggaa
gattatctgagcgtggtgctgaaccagctgtgcgtgctgcatgaaaaaacccggtgagc
gatcgcgtgaccaaatgctgcaccgaaagcctggtgaaccgccgccgtgctttagcgcg
ctggaagtggatgaaacctatgtgccgaaagaatttaacgcggaaaccttaccttcat
gcggatatttgcaccctgagcgaaaaagaacgccagattaaaaaacagaccgcgctggtg
gaactggtgaaacataaaccgaaagcgaccaaagaacagctgaaagcggtgatggatgat
tttgcggcgtttgtggaaaaatgctgcaaagcggatgataaagaacctgctttgcggaa
gaaggcaaaaaactggtggcggcgagccaggcggcgctgggcctgctgtgcaccccgagc
cgc
```

FIG. 8

DNA Sequences Encoding Exemplary Aldehyde-Tagged rHSA
N-, C- Termini, Internal loop Aldehyde tag modified rHSA atgaaatgggtgacctttattagcctgctgtttctgtttagcagcgcgtatagccgcggc
gtgtttcgcgcctgtgcaccccgagccgcgatgcgcataaaagcgaagtggcgcatcgc
tttaaagatctgggcgaagaaaactttaaagcgctggtgctgattgcgtttgcgcagtat
ctgcagcagtgcccgtttgaagatcatgtgaaactggtgaacgaagtgaccgaatttgcg
aaaacctgcgtggcggatgaaagcgcggaaaactgcgataaagcctgcatacccctgttt
ggcgataaactgtgcaccgtggcgaccctgcgcgaaacctatggcgaaatggcggattgc
tgcgcgaaacaggaaccggaacgcaacgaatgcttctgcagcataaagatgataaccccg
aacctgccgcgcctggtgcgcccggaagtggatgtgatgtgcaccgcgtttcatgataac
gaagaaacctttctgaaaaaatatctgtatgaaattgcgcgccgccatccgtatttttat
gcgccggaactgctgttttttgcgaaacgctataaagcggcgtttaccgaatgctgccag
gcggcggataaagcggcgtgcctgctgccgaaactggatgaactgcgcgatgaaggcaaa
gcgagcagcgcgaaacagcgcctgaaatgcgcgagcctgcagaaatttggcgaacgcgcg
tttaaagcgtgggcggtggcgcgcctgagccagcgctttccgaaagcggaatttgcggaa
gtgagcaaactggtgaccgatctgaccaaagtgcataccgaatgctgccatggcgatctg
ctggaatgcgcggatgatcgcgcggatctggcgaaatatatttgcgaaaaccaggatagc
attagcagcaaactgaaagaatgctgcgaaaaaccgctgctggaaaaaagccattgcatt
gcggaagtggaaaacgatgaaatgccggcgctgtgcaccccgagccgcgatctgccgagc
ctggcggcggattttgtggaaagcaaagatgtgtgcaaaaactatgcggaagcgaaagat
gtgtttctgggcatgtttctgtatgaatatgcgcgccgccatccggattatagcgtggtg
ctgctgctgcgcctggcgaaaacctatgaaaccaccctggaaaaatgctgcgcggcggcg
gatccgcatgaatgctatgcgaaagtgtttgatgaatttaaaccgctggtggaagaaccg
cagaacctgattaaacagaactgcgaactgtttgaacagctgggcgaatataaatttcag
aacgcgctgctggtgcgctataccaaaaaagtgccgcaggtgagcaccccgacccctggtg
gaagtgagccgcaacctgggcaaagtgggcagcaaatgctgcaaacatccggaagcgaaa
cgcatgccgtgcgcggaagattatctgagcgtggtgctgaaccagctgtgcgtgctgcat
gaaaaaacccccggtgagcgatcgcgtgaccaaatgctgcaccgaaagcctggtgaaccgc
cgcccgtgctttagcgcgctggaagtggatgaaacctatgtgccgaaagaatttaacgcg
gaaacctttacctttcatgcggatatttgcacccctgagcgaaaaagaacgccagattaaa
aaacagaccgcgctggtggaactggtgaaacataaaccgaaagcgaccaaagaacagctg
aaagcggtgatggatgattttgcggcgtttgtggaaaaatgctgcaaagcggatgataaa
gaaacctgctttgcggaagaaggcaaaaaactggtggcggcgagccaggcggcgctgggc
ctgctgtgcacccccgagccgc

FIG. 9

Exemplary Aldehyde-Tagged Fc Proteins

N- Terminal Recombinant Mouse IgG1-Fc carrier protein sequences

LCTPSRRSPP LKECPPCAAP DLLGGPSVFI FPPKIKDVLM ISLSPMVTCV VVDVSEDDPD VQISWFVNNV
EVHTAQTQTH REDYNSTLRV VSALPIQHQD WMSGKEFKCK VNNRALPSPI EKTISKPRGP VRAPQVYVLP
PPAEEMTKKE FSLTCMITGF LPAEIAVDWT SNGRTEQNYK NTATVLDSDG SYFMYSKLRV QKSTWERGSL
FACSVVHEGL HNHLTTKTIS RSLGK

C- Terminal Recombinant Mouse IgG1-Fc carrier protein sequences

RSPPLKECPP CAAPDLLGGP SVFIFPPKIK DVLMISLSPM VTCVVVDVSE DDPDVQISWF
VNNVEVHTAQ TQTHREDYNS TLRVVSALPI QHQDWMSGKE FKCKVNNRAL PSPIEKTISK
PRGPVRAPQV YVLPPPAEEM TKKEFSLTCM ITGFLPAEIA VDWTSNGRTE QNYKNTATVL
DSDGSYFMYS KLRVQKSTWE RGSLFACSVV HEGLHNHLTT KTISRSLGKL CTPSR

Multiple C- Terminal Recombinant Mouse IgG1-Fc carrier protein sequences

RSPPLKECPP CAAPDLLGGP SVFIFPPKIK DVLMISLSPM VTCVVVDVSE DDPDVQISWF
VNNVEVHTAQ TQTHREDYNS TLRVVSALPI QHQDWMSGKE FKCKVNNRAL PSPIEKTISK
PRGPVRAPQV YVLPPPAEEM TKKEFSLTCM ITGFLPAEIA VDWTSNGRTE QNYKNTATVL
DSDGSYFMYS KLRVQKSTWE RGSLFACSVV HEGLHNHLTT KTISRSLGKL CTPSRGGGGL
CTPSR

N-, C- Termini Recombinant Mouse IgG1-Fc carrier protein sequences

LCTPSRRSPP LKECPPCAAP DLLGGPSVFI FPPKIKDVLM ISLSPMVTCV VVDVSEDDPD VQISWFVNNV
EVHTAQTQTH REDYNSTLRV VSALPIQHQD WMSGKEFKCK VNNRALPSPI EKTISKPRGP VRAPQVYVLP
PPAEEMTKKE FSLTCMITGF LPAEIAVDWT SNGRTEQNYK NTATVLDSDG SYFMYSKLRV QKSTWERGSL
FACSVVHEGL HNHLTTKTIS RSLGKLCTPS
R

N- Terminal Recombinant Human IgG1-Fc carrier protein sequences

LCTPSRDKTH TCPPCPAPEL LGGPSVFLFP PKPKDTLMIS RTPEVTCVVV DVSHEDPEVK FNWYVDGVEV
HNAKTKPREE QYNSTYRVVS VLTVLHQDWL NGKEYKCKVS NKALPAPIEK TISKAKGQPR EPQVYTLPPS
REEMTKNQVS LTCLVKGFYP SDIAVEWESN GQPENNYKTT PPVLDSDGSF FLYSKLTVDK SRWQQGNVFS
CSVMHEGLHN HYTQKSLSLS PGK

FIG. 11

C- Terminal Recombinant Human IgG1-Fc carrier protein sequences

DKTHTCPPCP APELLGGPSV FLFPPKPKDT LMISRTPEVT CVVVDVSHED PEVKFNWYVD
GVEVHNAKTK PREEQYNSTY RVVSVLTVLH QDWLNGKEYK CKVSNKALPA PIEKTISKAK
GQPREPQVYT LPPSREEMTK NQVSLTCLVK GFYPSDIAVE WESNGQPENN YKTTPPVLDS
DGSFFLYSKL TVDKSRWQQG NVFSCSVMHE GLHNHYTQKS LSLSPGKLCT PSR

Multiple C- Terminal Recombinant Human IgG1-Fc carrier protein sequences

DKTHTCPPCP APELLGGPSV FLFPPKPKDT LMISRTPEVT CVVVDVSHED PEVKFNWYVD
GVEVHNAKTK PREEQYNSTY RVVSVLTVLH QDWLNGKEYK CKVSNKALPA PIEKTISKAK
GQPREPQVYT LPPSREEMTK NQVSLTCLVK GFYPSDIAVE WESNGQPENN YKTTPPVLDS
DGSFFLYSKL TVDKSRWQQG NVFSCSVMHE GLHNHYTQKS LSLSPGKLCT PSRGGGGLCT
PSR

N-, C- Terminal Recombinant Human IgG1-Fc carrier protein sequences

LCTPSRDKTH TCPPCPAPEL LGGPSVFLFP PKPKDTLMIS RTPEVTCVVV DVSHEDPEVK FNWYVDGVEV
HNAKTKPREE QYNSTYRVVS VLTVLHQDWL NGKEYKCKVS NKALPAPIEK TISKAKGQPR EPQVYTLPPS
REEMTKNQVS LTCLVKGFYP SDIAVEWESN GQPENNYKTT PPVLDSDGSF FLYSKLTVDK SRWQQGNVFS
CSVMHEGLHN HYTQKSLSLS PGKLCTPSR

FIG. 11 (Cont.)

```
SEQUENCE LISTING

<160> NUMBER OF SEQ ID NOS: 127

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide

<400> SEQUENCE: 1

Leu Cys Thr Pro Ser Arg
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide

<400> SEQUENCE: 2

Met Cys Thr Pro Ser Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Val Cys Thr Pro Ser Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Leu Cys Ser Pro Ser Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Leu Cys Ala Pro Ser Arg
```

```
<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Leu Cys Val Pro Ser Arg
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Leu Cys Gly Pro Ser Arg
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Ile Cys Thr Pro Ala Arg
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Leu Cys Thr Pro Ser Lys
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Met Cys Thr Pro Ser Lys
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Val Cys Thr Pro Ser Lys
1               5
```

```
<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

Leu Cys Ser Pro Ser Lys
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide

<400> SEQUENCE: 13

Leu Cys Ala Pro Ser Lys
1               5

<210> SEQ ID NO 14
<211> LENGTH: 6
<212> TYPE: PRT
<213> ORGANISM: Artificial Sequence
<220> FEATURE:
<223> OTHER INFORMATION: Synthetic peptide

<400> SEQUENCE: 14

Leu Cys Val Pro Ser Lys
1               5

<210> SEQ ID NO 15
<211> LENGTH: 6
<212> TYPE: PRT
<213> ORGANISM: Artificial Sequence
<220> FEATURE:
<223> OTHER INFORMATION: Synthetic peptide

<400> SEQUENCE: 15

Leu Cys Gly Pro Ser Lys
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide

<400> SEQUENCE: 16

Leu Cys Thr Pro Ser Ala
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide

<400> SEQUENCE: 17

Ile Cys Thr Pro Ala Ala
1               5
```

```
<210> SEQ ID NO 18
<211> LENGTH: 6
<212> TYPE: PRT
<213> ORGANISM: Artificial Sequence
<220> FEATURE:
<223> OTHER INFORMATION: Synthetic peptide

<400> SEQUENCE: 18

Met Cys Thr Pro Ser Ala
 1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic peptide

<400> SEQUENCE: 19

Val Cys Thr Pro Ser Ala
 1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide

<400> SEQUENCE: 20

Leu Cys Ser Pro Ser Ala
 1               5

<210> SEQ ID NO 21
<211> LENGTH: 6
<212> TYPE: PRT
<213> ORGANISM: Artificial Sequence
<220> FEATURE:
<223> OTHER INFORMATION: Synthetic peptide

<400> SEQUENCE: 21

Leu Cys Ala Pro Ser Ala
 1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic peptide

<400> SEQUENCE: 22

Leu Cys Val Pro Ser Ala
 1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide

<400> SEQUENCE: 23

Leu Cys Gly Pro Ser Ala
 1               5
```

```
<210> SEQ ID NO 24
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 24

Leu Gly Thr Pro Ser Arg
 1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 25

Met Gly Thr Pro Ser Arg
 1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 26

Val Gly Thr Pro Ser Arg
 1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 27

Leu Gly Ser Pro Ser Arg
 1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 28

Leu Gly Ala Pro Ser Arg
 1               5
```

```
<210> SEQ ID NO 29
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 29

Leu Gly Val Pro Ser Arg
 1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 30

Leu Gly Gly Pro Ser Arg
 1               5

<210> SEQ ID NO 31
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 31

Ile Gly Thr Pro Ala Arg
 1               5

<210> SEQ ID NO 32
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 32

Leu Gly Thr Pro Ser Lys
 1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 33

Met Gly Thr Pro Ser Lys
 1               5
```

```
<210> SEQ ID NO 34
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 34

Val Gly Thr Pro Ser Lys
 1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 35

Leu Gly Ser Pro Ser Lys
 1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 36

Leu Gly Ala Pro Ser Lys
 1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 37

Leu Gly Val Pro Ser Lys
 1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 38

Leu Gly Gly Pro Ser Lys
```

<210> SEQ ID NO 39
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 39

Leu Gly Thr Pro Ser Ala
 1               5

<210> SEQ ID NO 40
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 40

Met Gly Thr Pro Ser Ala
 1               5

<210> SEQ ID NO 41
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 41

Val Gly Thr Pro Ser Ala
 1               5

<210> SEQ ID NO 42
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 42

Leu Gly Ser Pro Ser Ala
 1               5

<210> SEQ ID NO 43
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 43

Leu Gly Ala Pro Ser Ala
1               5

<210> SEQ ID NO 44
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 44

Leu Gly Val Pro Ser Ala
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: FORMYLATION
<222> LOCATION: 2

<400> SEQUENCE: 45

Leu Gly Gly Pro Ser Ala
1               5

<210> SEQ ID NO 46
<211> LENGTH: 7
<212> TYPE: PRT
<213> ORGANISM: Artificial Sequence
<220> FEATURE:
<223> OTHER INFORMATION: Synthetic peptide

<400> SEQUENCE: 46

Ala Ala Leu Leu Thr Gly Arg
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic peptide

<400> SEQUENCE: 47

Ser Gln Leu Leu Thr Gly Arg
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic peptide

<400> SEQUENCE: 48

Ala Ala Phe Met Thr Gly Arg
1               5

<210> SEQ ID NO 49
<211> LENGTH: 7
<212> TYPE: PRT
<213> ORGANISM: Artificial Sequence

```
<220> FEATURE:
<223> OTHER INFORMATION: Synthetic peptide

<400> SEQUENCE: 49

Ala Ala Phe Leu Thr Gly Arg
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic peptide

<400> SEQUENCE: 50

Ser Ala Phe Leu Thr Gly Arg
1               5

<210> SEQ ID NO 51
<211> LENGTH: 7
<212> TYPE: PRT
<213> ORGANISM: Artificial Sequence
<220> FEATURE:
<223> OTHER INFORMATION: Synthetic peptide

<400> SEQUENCE: 51

Ala Ser Ile Leu Thr Gly Lys
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic peptide

<400> SEQUENCE: 52

Val Ser Phe Leu Thr Gly Arg
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic peptide

<400> SEQUENCE: 53

Ala Ser Leu Leu Thr Gly Leu
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic peptide

<400> SEQUENCE: 54

Ala Ser Ile Leu Ile Thr Gly
1               5

<210> SEQ ID NO 55
<211> LENGTH: 7
<212> TYPE: PRT
<213> ORGANISM: Artificial Sequence
<220> FEATURE:
```

<223> OTHER INFORMATION: Synthetic peptide

<400> SEQUENCE: 55

Val Ser Phe Leu Thr Gly Arg
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic peptide

<400> SEQUENCE: 56

Ser Ala Ile Met Thr Gly Arg
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic peptide

<400> SEQUENCE: 57

Ser Ala Ile Val Thr Gly Arg
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic peptide

<400> SEQUENCE: 58

Thr Asn Leu Trp Arg Gly
1               5

<210> SEQ ID NO 59
<211> LENGTH: 7
<212> TYPE: PRT
<213> ORGANISM: Artificial Sequence
<220> FEATURE:
<223> OTHER INFORMATION: Synthetic peptide

<400> SEQUENCE: 59

Thr Asn Leu Trp Arg Gly Gln
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic peptide

<400> SEQUENCE: 60

Thr Asn Leu Cys Ala Ala Ser
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic peptide

```
<400> SEQUENCE: 61

Val Ser Leu Trp Thr Gly Lys
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic peptide

<400> SEQUENCE: 62

Ser Met Leu Leu Thr Gly
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic peptide

<400> SEQUENCE: 63

Ser Met Leu Leu Thr Gly Asn
1               5

<210> SEQ ID NO 64
<211> LENGTH: 7
<212> TYPE: PRT
<213> ORGANISM: Artificial Sequence
<220> FEATURE:
<223> OTHER INFORMATION: Synthetic peptide

<400> SEQUENCE: 64

Ser Met Leu Leu Thr Gly Thr
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic peptide

<400> SEQUENCE: 65

Ala Ser Phe Met Ala Gly Gln
1               5

<210> SEQ ID NO 66
<211> LENGTH: 7
<212> TYPE: PRT
<213> ORGANISM: Artificial Sequence
<220> FEATURE:
<223> OTHER INFORMATION: Synthetic peptide

<400> SEQUENCE: 66

Ala Ser Leu Leu Thr Gly Leu
1               5

<210> SEQ ID NO 67
<211> LENGTH: 7
<212> TYPE: PRT
<213> ORGANISM: Artificial Sequence
<220> FEATURE:
<223> OTHER INFORMATION: Synthetic peptide
```

```
<400> SEQUENCE: 67

Gly Ser Leu Phe Thr Gly Arg
1               5

<210> SEQ ID NO 68
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: Misc_feature
<222> LOCATION: 6
<223> OTHER INFORMATION: Xaa is M or A

<400> SEQUENCE: 68

Cys Gly Pro Ser Arg Xaa Ser
1               5

<210> SEQ ID NO 69
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: Misc_feature
<222> LOCATION: 6
<223> OTHER INFORMATION: Xaa is M or A

<400> SEQUENCE: 69

Cys Gly Pro Ser Arg Xaa
1               5

<210> SEQ ID NO 70
<211> LENGTH: 609
<212> TYPE: PRT
<213> ORGANISM: Homo sapiens

<400> SEQUENCE: 70

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175
```

-continued

```
Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
            245                 250                 255

Lys Leu Val Thr Asp Leu Thr Lys Val His Thr Glu Cys Cys His Gly
        260                 265                 270

Asp Leu Leu Glu Cys Ala Asp Asp Arg Ala Asp Leu Ala Lys Tyr Ile
    275                 280                 285

Cys Glu Asn Gln Asp Ser Ile Ser Ser Lys Leu Lys Glu Cys Cys Glu
290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
            325                 330                 335

Lys Asp Val Cys Lys Asn Tyr Ala Glu Ala Lys Asp Val Phe Leu Gly
        340                 345                 350

Met Phe Leu Tyr Glu Tyr Ala Arg Arg His Pro Asp Tyr Ser Val Val
    355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
        420                 425                 430

Val Arg Tyr Thr Lys Lys Val Pro Gln Val Ser Thr Pro Thr Leu Val
    435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
        500                 505                 510

Ser Ala Leu Glu Val Asp Glu Thr Tyr Val Pro Lys Glu Phe Asn Ala
    515                 520                 525

Glu Thr Phe Thr Phe His Ala Asp Ile Cys Thr Leu Ser Glu Lys Glu
530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
        580                 585                 590
```

Ala Glu Glu Gly Lys Lys Leu Val Ala Ala Ser Gln Ala Ala Leu Gly
        595                 600                 605

Leu

<210> SEQ ID NO 71
<211> LENGTH: 1827
<212> TYPE: DNA
<213> ORGANISM: Homo sapiens

<400> SEQUENCE: 71

| | | | | | |
|---|---|---|---|---|---|
| atgaagtggg | taacctttat | ttcccttctt | tttctcttta | gctcggctta | ttccaggggt | 60 |
| gtgtttcgtc | gagatgcaca | caagagtgag | gttgctcatc | ggtttaaaga | tttgggagaa | 120 |
| gaaaatttca | agccttggt | gttgattgcc | tttgctcagt | atcttcagca | gtgtccattt | 180 |
| gaagatcatg | taaaattagt | gaatgaagta | actgaatttg | caaaaacatg | tgttgctgat | 240 |
| gagtcagctg | aaaattgtga | caaatcactt | cataccctt | ttggagacaa | attatgcaca | 300 |
| gttgcaactc | ttcgtgaaac | ctatggtgaa | atggctgact | gctgtgcaaa | acaagaacct | 360 |
| gagagaaatg | aatgcttctt | gcaacacaaa | gatgacaacc | caaacctccc | ccgattggtg | 420 |
| agaccagagg | ttgatgtgat | gtgcactgct | tttcatgaca | atgaagagac | atttttgaaa | 480 |
| aaatacttat | atgaaattgc | cagaagacat | ccttactttt | atgccccgga | actcctttc | 540 |
| tttgctaaaa | ggtataaagc | tgcttttaca | gaatgttgcc | aagctgctga | taaagctgcc | 600 |
| tgcctgttgc | caaagctcga | tgaacttcgg | gatgaaggga | aggcttcgtc | tgccaaacag | 660 |
| agactcaagt | gtgccagtct | ccaaaaattt | ggagaaagag | ctttcaaagc | atgggcagta | 720 |
| gctcgcctga | gccagagatt | tcccaaagct | gagtttgcag | aagtttccaa | gttagtgaca | 780 |
| gatcttacca | agtccacac | ggaatgctgc | catggagatc | tgcttgaatg | tgctgatgac | 840 |
| agggcggacc | ttgccaagta | tatctgtgaa | aatcaagatt | cgatctccag | taaactgaag | 900 |
| gaatgctgtg | aaaaacctct | gttggaaaaa | tcccactgca | ttgccgaagt | ggaaaatgat | 960 |
| gagatgcctg | ctgacttgcc | ttcattagct | gctgattttg | ttgaaagtaa | ggatgtttgc | 1020 |
| aaaaactatg | ctgaggcaaa | ggatgtcttc | ctgggcatgt | ttttgtatga | atatgcaaga | 1080 |
| aggcatcctg | attactctgt | cgtgctgctg | ctgagacttg | ccaagacata | tgaaaccact | 1140 |
| ctagagaagt | gctgtgccgc | tgcagatcct | catgaatgct | atgccaaagt | gttcgatgaa | 1200 |
| tttaaacctc | ttgtggaaga | gcctcagaat | ttaatcaaac | aaaattgtga | gcttttgag | 1260 |
| cagcttggag | agtacaaatt | ccagaatgcg | ctattagttc | gttacaccaa | gaaagtaccc | 1320 |
| caagtgtcaa | ctccaactct | tgtagaggtc | tcaagaaacc | taggaaaagt | gggcagcaaa | 1380 |
| tgttgtaaac | atcctgaagc | aaaaagaatg | ccctgtgcag | aagactatct | atccgtggtc | 1440 |
| ctgaaccagt | tatgtgtgtt | gcatgagaaa | acgccagtaa | gtgacagagt | caccaaatgc | 1500 |
| tgcacagaat | ccttggtgaa | caggcgacca | tgcttttcag | ctctggaagt | cgatgaaaca | 1560 |
| tacgttccca | agagtttaa | tgctgaaaca | ttcaccttcc | atgcagatat | atgcacactt | 1620 |
| tctgagaagg | agagacaaat | caagaaacaa | actgcacttg | ttgagctcgt | gaaacacaag | 1680 |
| cccaaggcaa | caaagagca | actgaaagct | gttatggatg | atttcgcagc | ttttgtagag | 1740 |
| aagtgctgca | aggctgacga | taaggagacc | tgctttgccg | aggagggtaa | aaaacttgtt | 1800 |
| gctgcaagtc | aagctgcctt | aggctta | | | | 1827 |

<210> SEQ ID NO 72
<211> LENGTH: 615
<212> TYPE: PRT

<213> ORGANISM: Artificial Sequence
<220> FEATURE:
<223> OTHER INFORMATION: Synthetic peptide

<400> SEQUENCE: 72

```
Met Lys Trp Val Thr Phe Ile Ser Leu Leu Phe Leu Phe Ser Ser Ala
1               5                   10                  15

Tyr Ser Arg Gly Val Phe Arg Arg Leu Cys Thr Pro Ser Arg Asp Ala
            20                  25                  30

His Lys Ser Glu Val Ala His Arg Phe Lys Asp Leu Gly Glu Glu Asn
        35                  40                  45

Phe Lys Ala Leu Val Leu Ile Ala Phe Ala Gln Tyr Leu Gln Gln Cys
50                  55                  60

Pro Phe Glu Asp His Val Lys Leu Val Asn Glu Val Thr Glu Phe Ala
65                  70                  75                  80

Lys Thr Cys Val Ala Asp Glu Ser Ala Glu Asn Cys Asp Lys Ser Leu
                85                  90                  95

His Thr Leu Phe Gly Asp Lys Leu Cys Thr Val Ala Thr Leu Arg Glu
            100                 105                 110

Thr Tyr Gly Glu Met Ala Asp Cys Cys Ala Lys Gln Glu Pro Glu Arg
        115                 120                 125

Asn Glu Cys Phe Leu Gln His Lys Asp Asp Asn Pro Asn Leu Pro Arg
130                 135                 140

Leu Val Arg Pro Glu Val Asp Val Met Cys Thr Ala Phe His Asp Asn
145                 150                 155                 160

Glu Glu Thr Phe Leu Lys Lys Tyr Leu Tyr Glu Ile Ala Arg Arg His
                165                 170                 175

Pro Tyr Phe Tyr Ala Pro Glu Leu Leu Phe Phe Ala Lys Arg Tyr Lys
            180                 185                 190

Ala Ala Phe Thr Glu Cys Cys Gln Ala Ala Asp Lys Ala Ala Cys Leu
        195                 200                 205

Leu Pro Lys Leu Asp Glu Leu Arg Asp Glu Gly Lys Ala Ser Ser Ala
210                 215                 220

Lys Gln Arg Leu Lys Cys Ala Ser Leu Gln Lys Phe Gly Glu Arg Ala
225                 230                 235                 240

Phe Lys Ala Trp Ala Val Ala Arg Leu Ser Gln Arg Phe Pro Lys Ala
                245                 250                 255

Glu Phe Ala Glu Val Ser Lys Leu Val Thr Asp Leu Thr Lys Val His
            260                 265                 270

Thr Glu Cys Cys His Gly Asp Leu Leu Glu Cys Ala Asp Asp Arg Ala
        275                 280                 285

Asp Leu Ala Lys Tyr Ile Cys Glu Asn Gln Asp Ser Ile Ser Ser Lys
290                 295                 300

Leu Lys Glu Cys Cys Glu Lys Pro Leu Leu Glu Lys Ser His Cys Ile
305                 310                 315                 320

Ala Glu Val Glu Asn Asp Glu Met Pro Ala Asp Leu Pro Ser Leu Ala
                325                 330                 335

Ala Asp Phe Val Glu Ser Lys Asp Val Cys Lys Asn Tyr Ala Glu Ala
            340                 345                 350

Lys Asp Val Phe Leu Gly Met Phe Leu Tyr Glu Tyr Ala Arg Arg His
        355                 360                 365

Pro Asp Tyr Ser Val Val Leu Leu Leu Arg Leu Ala Lys Thr Tyr Glu
370                 375                 380

Thr Thr Leu Glu Lys Cys Cys Ala Ala Ala Asp Pro His Glu Cys Tyr
```

```
                385                 390                 395                 400
Ala Lys Val Phe Asp Glu Phe Lys Pro Leu Val Glu Glu Pro Gln Asn
                    405                 410                 415

Leu Ile Lys Gln Asn Cys Glu Leu Phe Glu Gln Leu Gly Glu Tyr Lys
                420                 425                 430

Phe Gln Asn Ala Leu Leu Val Arg Tyr Thr Lys Lys Val Pro Gln Val
            435                 440                 445

Ser Thr Pro Thr Leu Val Glu Val Ser Arg Asn Leu Gly Lys Val Gly
        450                 455                 460

Ser Lys Cys Cys Lys His Pro Glu Ala Lys Arg Met Pro Cys Ala Glu
465                 470                 475                 480

Asp Tyr Leu Ser Val Val Leu Asn Gln Leu Cys Val Leu His Glu Lys
                485                 490                 495

Thr Pro Val Ser Asp Arg Val Thr Lys Cys Cys Thr Glu Ser Leu Val
                500                 505                 510

Asn Arg Arg Pro Cys Phe Ser Ala Leu Glu Val Asp Glu Thr Tyr Val
            515                 520                 525

Pro Lys Glu Phe Asn Ala Glu Thr Phe Thr Phe His Ala Asp Ile Cys
        530                 535                 540

Thr Leu Ser Glu Lys Glu Arg Gln Ile Lys Lys Gln Thr Ala Leu Val
545                 550                 555                 560

Glu Leu Val Lys His Lys Pro Lys Ala Thr Lys Glu Gln Leu Lys Ala
                565                 570                 575

Val Met Asp Asp Phe Ala Ala Phe Val Glu Lys Cys Cys Lys Ala Asp
                580                 585                 590

Asp Lys Glu Thr Cys Phe Ala Glu Glu Gly Lys Lys Leu Val Ala Ala
            595                 600                 605

Ser Gln Ala Ala Leu Gly Leu
        610                 615

<210> SEQ ID NO 73
<211> LENGTH: 615
<212> TYPE: PRT
<213> ORGANISM: Artificial Sequence
<220> FEATURE:
<223> OTHER INFORMATION: Synthetic peptide

<400> SEQUENCE: 73

Met Lys Trp Val Thr Phe Ile Ser Leu Leu Phe Leu Phe Ser Ser Ala
 1               5                  10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
```

```
                130                 135                 140
Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
                180                 185                 190

Cys Gln Ala Ala Asp Lys Ala Ala Cys Leu Leu Pro Lys Leu Asp Glu
                195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
                260                 265                 270

Asp Leu Leu Glu Cys Ala Asp Asp Arg Ala Asp Leu Ala Lys Tyr Ile
                275                 280                 285

Cys Glu Asn Gln Asp Ser Ile Ser Ser Lys Leu Lys Glu Cys Cys Glu
                290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
                340                 345                 350

Met Phe Leu Tyr Glu Tyr Ala Arg Arg His Pro Asp Tyr Ser Val Val
                355                 360                 365

Leu Leu Leu Arg Leu Ala Lys Thr Tyr Glu Thr Thr Leu Glu Lys Cys
370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
                420                 425                 430

Val Arg Tyr Thr Lys Lys Val Pro Gln Val Ser Thr Pro Thr Leu Val
                435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
                500                 505                 510

Ser Ala Leu Glu Val Asp Glu Thr Tyr Val Pro Lys Glu Phe Asn Ala
                515                 520                 525

Glu Thr Phe Thr Phe His Ala Asp Ile Cys Thr Leu Ser Glu Lys Glu
                530                 535                 540

Arg Gln Ile Lys Lys Gln Thr Ala Leu Val Glu Leu Val Lys His Lys
545                 550                 555                 560
```

```
Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
            595                 600                 605

Leu Leu Cys Thr Pro Ser Arg
            610             615

<210> SEQ ID NO 74
<211> LENGTH: 615
<212> TYPE: PRT
<213> ORGANISM: Artificial Sequence
<220> FEATURE:
<223> OTHER INFORMATION: Synthetic peptide

<400> SEQUENCE: 74

Met Lys Trp Val Thr Phe Ile Ser Leu Leu Phe Leu Phe Ser Ser Ala
  1               5                  10                  15

Tyr Ser Arg Gly Val Phe Arg Arg Asp Ala His Lys Ser Glu Val Ala
             20                  25                  30

His Arg Phe Lys Asp Leu Gly Glu Glu Asn Phe Lys Ala Leu Val Leu
         35                  40                  45

Ile Ala Phe Ala Gln Tyr Leu Gln Gln Cys Pro Phe Glu Asp His Val
     50                  55                  60

Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300
```

```
Lys Pro Leu Leu Glu Lys Ser His Cys Ile Ala Glu Val Glu Asn Asp
305                 310                 315                 320

Glu Met Pro Ala Leu Cys Thr Pro Ser Arg Asp Leu Pro Ser Leu Ala
            325                 330                 335

Ala Asp Phe Val Glu Ser Lys Asp Val Cys Lys Asn Tyr Ala Glu Ala
        340                 345                 350

Lys Asp Val Phe Leu Gly Met Phe Leu Tyr Glu Tyr Ala Arg Arg His
    355                 360                 365

Pro Asp Tyr Ser Val Val Leu Leu Arg Leu Ala Lys Thr Tyr Glu
370                 375                 380

Thr Thr Leu Glu Lys Cys Cys Ala Ala Ala Asp Pro His Glu Cys Tyr
385                 390                 395                 400

Ala Lys Val Phe Asp Glu Phe Lys Pro Leu Val Glu Glu Pro Gln Asn
                405                 410                 415

Leu Ile Lys Gln Asn Cys Glu Leu Phe Glu Gln Leu Gly Glu Tyr Lys
            420                 425                 430

Phe Gln Asn Ala Leu Leu Val Arg Tyr Thr Lys Lys Val Pro Gln Val
        435                 440                 445

Ser Thr Pro Thr Leu Val Glu Val Ser Arg Asn Leu Gly Lys Val Gly
    450                 455                 460

Ser Lys Cys Cys Lys His Pro Glu Ala Lys Arg Met Pro Cys Ala Glu
465                 470                 475                 480

Asp Tyr Leu Ser Val Val Leu Asn Gln Leu Cys Val Leu His Glu Lys
                485                 490                 495

Thr Pro Val Ser Asp Arg Val Thr Lys Cys Cys Thr Glu Ser Leu Val
            500                 505                 510

Asn Arg Arg Pro Cys Phe Ser Ala Leu Glu Val Asp Glu Thr Tyr Val
        515                 520                 525

Pro Lys Glu Phe Asn Ala Glu Thr Phe Thr Phe His Ala Asp Ile Cys
    530                 535                 540

Thr Leu Ser Glu Lys Glu Arg Gln Ile Lys Lys Gln Thr Ala Leu Val
545                 550                 555                 560

Glu Leu Val Lys His Lys Pro Lys Ala Thr Lys Glu Gln Leu Lys Ala
                565                 570                 575

Val Met Asp Asp Phe Ala Ala Phe Val Glu Lys Cys Cys Lys Ala Asp
            580                 585                 590

Asp Lys Glu Thr Cys Phe Ala Glu Glu Gly Lys Lys Leu Val Ala Ala
        595                 600                 605

Ser Gln Ala Ala Leu Gly Leu
    610                 615

<210> SEQ ID NO 75
<211> LENGTH: 621
<212> TYPE: PRT
<213> ORGANISM: Artificial Sequence
<220> FEATURE:
<223> OTHER INFORMATION: Synthetic peptide

<400> SEQUENCE: 75

Met Lys Trp Val Thr Phe Ile Ser Leu Leu Phe Leu Phe Ser Ser Ala
1               5                   10                  15

Tyr Ser Arg Gly Val Phe Arg Arg Leu Cys Thr Pro Ser Arg Asp Ala
            20                  25                  30

His Lys Ser Glu Val Ala His Arg Phe Lys Asp Leu Gly Glu Glu Asn
        35                  40                  45
```

```
Phe Lys Ala Leu Val Leu Ile Ala Phe Ala Gln Tyr Leu Gln Gln Cys
 50                  55                  60

Pro Phe Glu Asp His Val Lys Leu Val Asn Glu Val Thr Glu Phe Ala
 65                  70                  75                  80

Lys Thr Cys Val Ala Asp Glu Ser Ala Glu Asn Cys Asp Lys Ser Leu
                 85                  90                  95

His Thr Leu Phe Gly Asp Lys Leu Cys Thr Val Ala Thr Leu Arg Glu
            100                 105                 110

Thr Tyr Gly Glu Met Ala Asp Cys Cys Ala Lys Gln Glu Pro Glu Arg
            115                 120                 125

Asn Glu Cys Phe Leu Gln His Lys Asp Asp Asn Pro Asn Leu Pro Arg
130                 135                 140

Leu Val Arg Pro Glu Val Asp Val Met Cys Thr Ala Phe His Asp Asn
145                 150                 155                 160

Glu Glu Thr Phe Leu Lys Lys Tyr Leu Tyr Glu Ile Ala Arg Arg His
                165                 170                 175

Pro Tyr Phe Tyr Ala Pro Glu Leu Leu Phe Phe Ala Lys Arg Tyr Lys
            180                 185                 190

Ala Ala Phe Thr Glu Cys Cys Gln Ala Ala Asp Lys Ala Ala Cys Leu
            195                 200                 205

Leu Pro Lys Leu Asp Glu Leu Arg Asp Glu Gly Lys Ala Ser Ser Ala
210                 215                 220

Lys Gln Arg Leu Lys Cys Ala Ser Leu Gln Lys Phe Gly Glu Arg Ala
225                 230                 235                 240

Phe Lys Ala Trp Ala Val Ala Arg Leu Ser Gln Arg Phe Pro Lys Ala
                245                 250                 255

Glu Phe Ala Glu Val Ser Lys Leu Val Thr Asp Leu Thr Lys Val His
            260                 265                 270

Thr Glu Cys Cys His Gly Asp Leu Leu Glu Cys Ala Asp Asp Arg Ala
            275                 280                 285

Asp Leu Ala Lys Tyr Ile Cys Glu Asn Gln Asp Ser Ile Ser Ser Lys
290                 295                 300

Leu Lys Glu Cys Cys Glu Lys Pro Leu Leu Glu Lys Ser His Cys Ile
305                 310                 315                 320

Ala Glu Val Glu Asn Asp Glu Met Pro Ala Asp Leu Pro Ser Leu Ala
                325                 330                 335

Ala Asp Phe Val Glu Ser Lys Asp Val Cys Lys Asn Tyr Ala Glu Ala
            340                 345                 350

Lys Asp Val Phe Leu Gly Met Phe Leu Tyr Glu Tyr Ala Arg Arg His
            355                 360                 365

Pro Asp Tyr Ser Val Val Leu Leu Leu Arg Leu Ala Lys Thr Tyr Glu
370                 375                 380

Thr Thr Leu Glu Lys Cys Cys Ala Ala Ala Asp Pro His Glu Cys Tyr
385                 390                 395                 400

Ala Lys Val Phe Asp Glu Phe Lys Pro Leu Val Glu Glu Pro Gln Asn
                405                 410                 415

Leu Ile Lys Gln Asn Cys Glu Leu Phe Glu Gln Leu Gly Glu Tyr Lys
            420                 425                 430

Phe Gln Asn Ala Leu Leu Val Arg Tyr Thr Lys Lys Val Pro Gln Val
            435                 440                 445

Ser Thr Pro Thr Leu Val Glu Val Ser Arg Asn Leu Gly Lys Val Gly
450                 455                 460
```

Ser Lys Cys Cys Lys His Pro Glu Ala Lys Arg Met Pro Cys Ala Glu
465                 470                 475                 480

Asp Tyr Leu Ser Val Val Leu Asn Gln Leu Cys Val Leu His Glu Lys
                485                 490                 495

Thr Pro Val Ser Asp Arg Val Thr Lys Cys Cys Thr Glu Ser Leu Val
            500                 505                 510

Asn Arg Arg Pro Cys Phe Ser Ala Leu Glu Val Asp Glu Thr Tyr Val
        515                 520                 525

Pro Lys Glu Phe Asn Ala Glu Thr Phe Thr Phe His Ala Asp Ile Cys
    530                 535                 540

Thr Leu Ser Glu Lys Glu Arg Gln Ile Lys Lys Gln Thr Ala Leu Val
545                 550                 555                 560

Glu Leu Val Lys His Lys Pro Lys Ala Thr Lys Glu Gln Leu Lys Ala
                565                 570                 575

Val Met Asp Asp Phe Ala Ala Phe Val Glu Lys Cys Cys Lys Ala Asp
                580                 585                 590

Asp Lys Glu Thr Cys Phe Ala Glu Glu Gly Lys Lys Leu Val Ala Ala
        595                 600                 605

Ser Gln Ala Ala Leu Gly Leu Leu Cys Thr Pro Ser Arg
    610                 615                 620

<210> SEQ ID NO 76
<211> LENGTH: 627
<212> TYPE: PRT
<213> ORGANISM: Artificial Sequence
<220> FEATURE:
<223> OTHER INFORMATION: Synthetic peptide

<400> SEQUENCE: 76

Met Lys Trp Val Thr Phe Ile Ser Leu Leu Phe Leu Phe Ser Ser Ala
1               5                   10                  15

Tyr Ser Arg Gly Val Phe Arg Arg Leu Cys Thr Pro Ser Arg Asp Ala
                20                  25                  30

His Lys Ser Glu Val Ala His Arg Phe Lys Asp Leu Gly Glu Glu Asn
            35                  40                  45

Phe Lys Ala Leu Val Leu Ile Ala Phe Ala Gln Tyr Leu Gln Gln Cys
        50                  55                  60

Pro Phe Glu Asp His Val Lys Leu Val Asn Glu Val Thr Glu Phe Ala
65                  70                  75                  80

Lys Thr Cys Val Ala Asp Glu Ser Ala Glu Asn Cys Asp Lys Ser Leu
                85                  90                  95

His Thr Leu Phe Gly Asp Lys Leu Cys Thr Val Ala Thr Leu Arg Glu
            100                 105                 110

Thr Tyr Gly Glu Met Ala Asp Cys Cys Ala Lys Gln Glu Pro Glu Arg
        115                 120                 125

Asn Glu Cys Phe Leu Gln His Lys Asp Asp Asn Pro Asn Leu Pro Arg
130                 135                 140

Leu Val Arg Pro Glu Val Asp Val Met Cys Thr Ala Phe His Asp Asn
145                 150                 155                 160

Glu Glu Thr Phe Leu Lys Lys Tyr Leu Tyr Glu Ile Ala Arg Arg His
                165                 170                 175

Pro Tyr Phe Tyr Ala Pro Glu Leu Leu Phe Phe Ala Lys Arg Tyr Lys
            180                 185                 190

Ala Ala Phe Thr Glu Cys Cys Gln Ala Ala Asp Lys Ala Ala Cys Leu
        195                 200                 205

```
Leu Pro Lys Leu Asp Glu Leu Arg Asp Glu Gly Lys Ala Ser Ser Ala
    210                 215                 220

Lys Gln Arg Leu Lys Cys Ala Ser Leu Gln Lys Phe Gly Glu Arg Ala
225                 230                 235                 240

Phe Lys Ala Trp Ala Val Ala Arg Leu Ser Gln Arg Phe Pro Lys Ala
                245                 250                 255

Glu Phe Ala Glu Val Ser Lys Leu Val Thr Asp Leu Thr Lys Val His
                260                 265                 270

Thr Glu Cys Cys His Gly Asp Leu Leu Glu Cys Ala Asp Asp Arg Ala
                275                 280                 285

Asp Leu Ala Lys Tyr Ile Cys Glu Asn Gln Asp Ser Ile Ser Ser Lys
            290                 295                 300

Leu Lys Glu Cys Cys Glu Lys Pro Leu Leu Glu Lys Ser His Cys Ile
305                 310                 315                 320

Ala Glu Val Glu Asn Asp Glu Met Pro Ala Leu Cys Thr Pro Ser Arg
                    325                 330                 335

Asp Leu Pro Ser Leu Ala Ala Asp Phe Val Glu Ser Lys Asp Val Cys
            340                 345                 350

Lys Asn Tyr Ala Glu Ala Lys Asp Val Phe Leu Gly Met Phe Leu Tyr
            355                 360                 365

Glu Tyr Ala Arg Arg His Pro Asp Tyr Ser Val Val Leu Leu Leu Arg
370                 375                 380

Leu Ala Lys Thr Tyr Glu Thr Thr Leu Glu Lys Cys Cys Ala Ala Ala
385                 390                 395                 400

Asp Pro His Glu Cys Tyr Ala Lys Val Phe Asp Glu Phe Lys Pro Leu
                405                 410                 415

Val Glu Glu Pro Gln Asn Leu Ile Lys Gln Asn Cys Glu Leu Phe Glu
                420                 425                 430

Gln Leu Gly Glu Tyr Lys Phe Gln Asn Ala Leu Leu Val Arg Tyr Thr
            435                 440                 445

Lys Lys Val Pro Gln Val Ser Thr Pro Thr Leu Val Glu Val Ser Arg
450                 455                 460

Asn Leu Gly Lys Val Gly Ser Lys Cys Cys Lys His Pro Glu Ala Lys
465                 470                 475                 480

Arg Met Pro Cys Ala Glu Asp Tyr Leu Ser Val Val Leu Asn Gln Leu
                485                 490                 495

Cys Val Leu His Glu Lys Thr Pro Val Ser Asp Arg Val Thr Lys Cys
            500                 505                 510

Cys Thr Glu Ser Leu Val Asn Arg Arg Pro Cys Phe Ser Ala Leu Glu
            515                 520                 525

Val Asp Glu Thr Tyr Val Pro Lys Glu Phe Asn Ala Glu Thr Phe Thr
530                 535                 540

Phe His Ala Asp Ile Cys Thr Leu Ser Glu Lys Glu Arg Gln Ile Lys
545                 550                 555                 560

Lys Gln Thr Ala Leu Val Glu Leu Val Lys His Lys Pro Lys Ala Thr
                565                 570                 575

Lys Glu Gln Leu Lys Ala Val Met Asp Asp Phe Ala Ala Phe Val Glu
            580                 585                 590

Lys Cys Cys Lys Ala Asp Asp Lys Glu Thr Cys Phe Ala Glu Glu Gly
            595                 600                 605

Lys Lys Leu Val Ala Ala Ser Gln Ala Ala Leu Gly Leu Leu Cys Thr
610                 615                 620

Pro Ser Arg
```

<210> SEQ ID NO 77
<211> LENGTH: 1845
<212> TYPE: DNA
<213> ORGANISM: Artificial Sequence
<220> FEATURE:
<223> OTHER INFORMATION: Synthetic nucleotide

<400> SEQUENCE: 77

```
atgaaatggg tgacctttat tagcctgctg tttctgttta gcagcgcgta tagccgcggc      60
gtgtttcgcc gcctgtgcac cccgagccgc gatgcgcata aaagcgaagt ggcgcatcgc     120
tttaaagatc tgggcgaaga aactttaaa gcgctggtgc tgattgcgtt tgcgcagtat     180
ctgcagcagt gcccgtttga agatcatgtg aaactggtga acgaagtgac cgaatttgcg     240
aaaacctgcg tggcggatga agcgcggaa aactgcgata aaagcctgca taccctgttt     300
ggcgataaac tgtgcaccgt ggcgaccctg cgcgaaacct atggcgaaat ggcggattgc     360
tgcgcgaaac aggaaccgga acgcaacgaa tgctttctgc agcataaaga tgataacccg     420
aacctgccgc gcctggtgcg cccggaagtg atgtgatgt gcaccgcgtt tcatgataac     480
gaagaaacct ttctgaaaaa atatctgtat gaaattgcgc cgccatcc gtattttat     540
gcgccggaac tgctgttttt tgcgaaacgc tataaagcgg cgtttaccga atgctgccag     600
gcggcgata aagcggcgtg cctgctgccg aaactggatg aactgcgcga tgaaggcaaa     660
gcgagcagcg cgaaacagcg cctgaaatgc gcgagcctgc agaaatttgg cgaacgcgcg     720
tttaaagcgt gggcggtggc gcgcctgagc cagcgctttc gaaagcgga atttgcggaa     780
gtgagcaaac tggtgaccga tctgaccaaa gtgcataccg aatgctgcca tggcgatctg     840
ctggaatgcg cggatgatcg cgcggatctg gcgaaatata tttgcgaaaa ccaggatagc     900
attagcagca aactgaaaga tgctgcgaa aaaccgctgc tggaaaaag ccattgcatt     960
gcggaagtgg aaaacgatga atgccggcg gatctgccga gcctggcggc ggattttgtg    1020
gaaagcaaag atgtgtgcaa aaactatgcg gaagcgaaag atgtgtttct gggcatgttt    1080
ctgtatgaat atgcgcgccg ccatccggat atagcgtgg tgctgctgct cgcctggcg    1140
aaaacctatg aaaccaccct ggaaaaatgc tgcgcggcgg cggatccgca tgaatgctat    1200
gcgaaagtgt ttgatgaatt taaaccgctg gtggaagaac cgcagaacct gattaaacag    1260
aactgcgaac tgtttgaaca gctgggcgaa tataaatttc agaacgcgct gctggtgcgc    1320
tataccaaaa aagtgccgca ggtgagcacc ccgaccctgg tggaagtgag ccgcaacctg    1380
ggcaaagtgg gcagcaaatg ctgcaaacat ccggaagcga acgcatgcc gtgcgcggaa    1440
gattatctga gcgtggtgct gaaccagctg tgcgtgctgc atgaaaaaac cccggtgagc    1500
gatcgcgtga ccaaatgctg caccgaaagc ctggtgaacc gccgcccgtg ctttagcgcg    1560
ctggaagtgg atgaaaccta tgtgccgaaa gaatttaacg cggaaaccct taccttcat    1620
gcggatattt gcaccctgag cgaaaaagaa cgccagatta aaaacagac cgcgctggtg    1680
gaactggtga acataaaacc gaaagcgacc aagaacagc tgaaagcggt gatggatgat    1740
tttgcggcgt ttgtggaaaa atgctgcaaa cggatgata agaaacctg ctttgcggaa    1800
gaaggcaaaa aactggtggc ggcgagccag gcggcgctgg gcctg                   1845
```

<210> SEQ ID NO 78
<211> LENGTH: 1845
<212> TYPE: DNA
<213> ORGANISM: Artificial Sequence
<220> FEATURE:
<223> OTHER INFORMATION: Synthetic nucleotide

<400> SEQUENCE: 78

```
atgaaatggg tgacctttat tagcctgctg tttctgttta gcagcgcgta tagccgcggc      60
gtgtttcgcc gcgatgcgca taaaagcgaa gtggcgcatc gctttaaaga tctgggcgaa     120
gaaaacttta aagcgctggt gctgattgcg tttgcgcagt atctgcagca gtgcccgttt     180
gaagatcatg tgaaactggt gaacgaagtg accgaatttg cgaaaacctg cgtggcggat     240
gaaagcgcgg aaaactgcga taaaagcctg catacccctgt ttggcgataa actgtgcacc     300
gtggcgaccc tgcgcgaaac ctatggcgaa atggcggatt gctgcgcgaa acaggaaccg     360
gaacgcaacg aatgctttct gcagcataaa gatgataacc cgaacctgcc gcgcctggtg     420
cgcccggaag tggatgtgat gtgcaccgcg tttcatgata cgaagaaaac ctttctgaaa     480
aaatatctgt atgaaattgc gcgccgccat ccgtattttt atgcgccgga actgctgttt     540
tttgcgaaac gctataaagc ggcgtttacc gaatgctgcc aggcggcgga taaagcggcg     600
tgcctgctgc cgaaactgga tgaactgcgc gatgaaggca aagcgagcag cgcgaaacag     660
cgcctgaaat gcgcgagcct gcagaaattt ggcgaacgcg cgtttaaagc gtgggcggtg     720
gcgcgcctga ccagcgcctt tccgaaagcg gaatttgcgg aagtgagcaa actggtgacc     780
gatctgacca agtgcatac cgaatgctgc catggcgatc tgctgaaatg cgcggatgat     840
cgcgcggatc tggcgaaata tatttgcgaa aaccaggata gcattagcag caaactgaaa     900
gaatgctgcg aaaaaccgct gctggaaaaa agccattgca ttgcggaagt ggaaaacgat     960
gaaatgccgg cggatctgcc gagcctggcg gcggattttg tggaaagcaa agatgtgtgc    1020
aaaaactatg cggaagcgaa agatgtgttt ctgggcatgt ttctgtatga atatgcgcgc    1080
cgccatccgg attatagcgt ggtgctgctg ctgcgcctgg cgaaaaccta tgaaaccacc    1140
ctggaaaaat gctgcgcggc ggcggatccg catgaatgct atgcgaaagt gtttgatgaa    1200
tttaaaccgc tggtggaaga accgcagaac ctgattaaac agaactgcga actgtttgaa    1260
cagctgggcg aatataaatt tcagaacgcg ctgctggtgc gctataccaa aaaagtgccg    1320
caggtgagca ccccgaccct ggtggaagtg agccgcaacc tgggcaaagt gggcagcaaa    1380
tgctgcaaac atccggaagc gaaacgcatg ccgtgcgcgg aagattatct gagcgtggtg    1440
ctgaaccagc tgtgcgtgct gcatgaaaaa accccggtga cgatcgcgt gaccaaatgc    1500
tgcaccgaaa gcctggtgaa ccgccgcccg tgctttagcg cgctggaagt ggatgaaacc    1560
tatgtgccga agaatttaa cgcgaaaacc tttacctttc atgcggatat ttgcaccctg    1620
agcgaaaaag aacgccagat taaaaaacag accgcgctgg tggaactggt gaaacataaa    1680
ccgaaagcga ccaaagaaca gctgaaagcg tgatggatg attttgcggc gtttgtggaa    1740
aaatgctgca agcggatga taaagaaacc tgctttgcgg aagaaggcaa aaaactggtg    1800
gcggcgagcc aggcggcgct gggcctgctg tgcaccccga gccgc                    1845
```

<210> SEQ ID NO 79
<211> LENGTH: 1845
<212> TYPE: DNA
<213> ORGANISM: Artificial Sequence
<220> FEATURE:
<223> OTHER INFORMATION: Synthetic nucleotide

<400> SEQUENCE: 79

```
atgaaatggg tgacctttat tagcctgctg tttctgttta gcagcgcgta tagccgcggc      60
```

| | |
|---|---|
| gtgtttcgcc gcgatgcgca taaaagcgaa gtggcgcatc gctttaaaga tctgggcgaa | 120 |
| gaaaacttta agcgctggt gctgattgcg tttgcgcagt atctgcagca gtgcccgttt | 180 |
| gaagatcatg tgaaactggt gaacgaagtg accgaatttg cgaaaacctg cgtggcggat | 240 |
| gaaagcgcgg aaaactgcga taaaagcctg cataccctgt ttggcgataa actgtgcacc | 300 |
| gtggcgaccc tgcgcgaaac ctatggcgaa atggcggatt gctgcgcgaa acaggaaccg | 360 |
| gaacgcaacg aatgctttct gcagcataaa gatgataacc cgaacctgcc cgcctggtg | 420 |
| cgcccggaag tggatgtgat gtgcaccgcg tttcatgata cgaagaaac ctttctgaaa | 480 |
| aaatatctgt atgaaattgc cgccgccat ccgtattttt atgcgccgga actgctgttt | 540 |
| tttgcgaaac gctataaagc ggcgtttacc gaatgctgcc aggcggcgga taaagcggcg | 600 |
| tgcctgctgc cgaaactgga tgaactgcgc gatgaaggca agcgagcag cgcgaaacag | 660 |
| cgcctgaaat gcgcgagcct gcagaaattt ggcgaacgcg cgtttaaagc gtgggcggtg | 720 |
| gcgcgcctga ccagcgctt ccgaaagcg gaatttgcgg aagtgagcaa actggtgacc | 780 |
| gatctgacca aagtgcatac cgaatgctgc catggcgatc tgctggaatg cgcggatgat | 840 |
| cgcgcggatc tggcgaaata tatttgcgaa aaccaggata gcattagcag caaactgaaa | 900 |
| gaatgctgcg aaaaaccgct gctggaaaaa agccattgca ttgcggaagt ggaaaacgat | 960 |
| gaaatgccgg cgctgtgcac cccgagccgc gatctgccga gcctggcggc ggattttgtg | 1020 |
| gaaagcaaag atgtgtgcaa aaactatgcg gaagcgaaag atgtgtttct gggcatgttt | 1080 |
| ctgtatgaat atgcgcgccg ccatccggat tatagcgtgg tgctgctgct gcgcctggcg | 1140 |
| aaaacctatg aaaccaccct ggaaaaatgc tgcgcggcgg cggatccgca tgaatgctat | 1200 |
| gcgaaagtgt ttgatgaatt taaaccgctg gtggaagaac cgcagaaacct gattaaacag | 1260 |
| aactgcgaac tgtttgaaca gctgggcgaa tataaatttc agaacgcgct gctggtgcgc | 1320 |
| tataccaaaa aagtgccgca ggtgagcacc ccgaccctgg tggaagtgag ccgcaacctg | 1380 |
| ggcaaagtgg gcagcaaatg ctgcaaacat ccggaagcga aacgcatgcc gtgcgcggaa | 1440 |
| gattatctga gcgtggtgct gaaccagctg tgcgtgctgc atgaaaaaac cccggtgagc | 1500 |
| gatcgcgtga ccaaatgctg caccgaaagc ctggtgaacc gccgcccgtg ctttagcgcg | 1560 |
| ctggaagtgg atgaaaccta tgtgccgaaa gaatttaacg cggaaacctt tacctttcat | 1620 |
| gcggatattt gcaccctgag cgaaaaagaa cgccagatta aaaaacagac cgcgctggtg | 1680 |
| gaactggtga acataaaacc gaaagcgacc aaagaacagc tgaaagcggt gatggatgat | 1740 |
| tttgcggcgt ttgtggaaaa atgctgcaaa gcggatgata agaaacctg ctttgcggaa | 1800 |
| gaaggcaaaa aactggtggc ggcgagccag gcggcgctgg gcctg | 1845 |

<210> SEQ ID NO 80
<211> LENGTH: 1863
<212> TYPE: DNA
<213> ORGANISM: Artificial Sequence
<220> FEATURE:
<223> OTHER INFORMATION: Synthetic nucleotide

<400> SEQUENCE: 80

| | |
|---|---|
| atgaaatggg tgacctttat tagcctgctg tttctgtta gcagcgcgta tagccgcggc | 60 |
| gtgtttcgcc gcctgtgcac cccgagccgc gatgcgcata aaagcgaagt ggcgcatcgc | 120 |
| tttaaagatc tgggcgaaga aaactttaaa gcgctggtgc tgattgcgtt tgcgcagtat | 180 |
| ctgcagcagt gcccgtttga agatcatgtg aaactggtga cgaagtgac cgaatttgcg | 240 |
| aaacctgcg tggcggatga agcgcggaa aactgcgata aaagcctgca taccctgttt | 300 |

```
ggcgataaac tgtgcaccgt ggcgaccctg cgcgaaacct atggcgaaat ggcggattgc      360
tgcgcgaaac aggaaccgga acgcaacgaa tgctttctgc agcataaaga tgataacccg      420
aacctgccgc gcctggtgcg cccggaagtg atgtgatgt gcaccgcgtt tcatgataac       480
gaagaaacct ttctgaaaaa atatctgtat gaaattgcgc cgccgcatcc gtattttat      540 gcgccggaac tgctgttttt tgcgaaacgc tataaagcgg cgtttaccga atgctgccag      600
gcggcggata aagcggcgtg cctgctgccg aaactggatg aactgcgcga tgaaggcaaa      660
gcgagcagcg cgaaacagcg cctgaaatgc gcgagcctgc agaaatttgg cgaacgcgcg      720
tttaaagcgt gggcggtggc gcgcctgagc cagcgctttc gaaagcgga atttgcggaa      780 gtgagcaaac tggtgaccga tctgaccaaa gtgcataccg aatgctgcca tggcgatctg      840
ctggaatgcg cggatgatcg cgcggatctg gcgaaatata tttgcgaaaa ccaggatagc      900
attagcagca aactgaaaga atgctgcgaa aaaccgctgc tggaaaaaag ccattgcatt      960
gcggaagtgg aaaacgatga atgccggcg atctgccga cctggcggc ggattttgtg        1020 gaaagcaaag atgtgtgcaa aaactatgcg gaagcgaaag atgtgtttct gggcatgttt      1080
ctgtatgaat atgcgcgccg ccatccggat tatagcgtgg tgctgctgct cgcctggcg       1140 aaaacctatg aaaccacccct ggaaaaatgc tgcgcggcgg cggatccgca tgaatgctat      1200
gcgaaagtgt ttgatgaatt taaaccgctg gtggaagaac gcagaacct gattaaacag       1260 aactgcgaac tgtttgaaca gctgggcgaa tataaatttc agaacgcgct gctggtgcgc      1320
tataccaaaa aagtgccgca ggtgagcacc ccgaccctgg tggaagtgag ccgcaacctg      1380
ggcaaagtgg gcagcaaatg ctgcaaacat ccggaagcga acgcatgcc gtgcgcggaa       1440 gattatctga gcgtggtgct gaaccagctg tgcgtgctgc atgaaaaaac cccggtgagc      1500
gatcgcgtga ccaaatgctg caccgaaagc ctggtgaacc gccgcccgtg ctttagcgcg      1560
ctggaagtgg atgaaaccta tgtgccgaaa gaatttaacg cggaaacctt taccttttcat      1620 gcggatattt gcaccctgag cgaaaaagaa cgccagatta aaaacagac cgcgctggtg      1680 gaactggtga acataaaacc gaaagcgacc aaagaacagc tgaaagcggt gatggatgat      1740
tttgcggcgt ttgtggaaaa atgctgcaaa gcggatgata agaaaacctg ctttgcggaa      1800
gaaggcaaaa aactggtggc ggcgagccag gcggcgctgg gcctgctgtg cacccccgagc      1860 cgc                                                                    1863
```

<210> SEQ ID NO 81
<211> LENGTH: 1881
<212> TYPE: DNA
<213> ORGANISM: Artificial Sequence
<220> FEATURE:
<223> OTHER INFORMATION: Synthetic nucleotide

<400> SEQUENCE: 81

```
atgaaatggg tgacctttat tagcctgctg tttctgttta gcagcgcgta tagccgcggc       60
gtgtttcgcc gcctgtgcac cccgagccgc gatgcgcata aagcgaagt ggcgcatcgc      120 tttaaagatc tgggcgaaga aactttaaa gcgctggtgc tgattgcgtt tgcgcagtat       180
ctgcagcagt gcccgtttga agatcatgtg aaactggtga acgaagtgac cgaatttgcg      240
aaaacctgcg tggcggatga agcgcggaa aactgcgata aagcctgca taccctgttt       300 ggcgataaac tgtgcaccgt ggcgaccctg cgcgaaacct atggcgaaat ggcggattgc      360
tgcgcgaaac aggaaccgga acgcaacgaa tgctttctgc agcataaaga tgataacccg      420
```

```
aacctgccgc gcctggtgcg cccggaagtg gatgtgatgt gcaccgcgtt tcatgataac    480
gaagaaacct ttctgaaaaa atatctgtat gaaattgcgc cccgccatcc gtattttat    540
gcgccggaac tgctgttttt tgcgaaacgc tataaagcgg cgtttaccga atgctgccag    600
gcggcggata aagcggcgtg cctgctgccg aaactggatg aactgcgcga tgaaggcaaa    660
gcgagcagcg cgaaacagcg cctgaaatgc gcgagcctgc agaaatttgg cgaacgcgcg    720
tttaaagcgt gggcggtggc gcgcctgagc cagcgctttc cgaaagcgga atttgcggaa    780
gtgagcaaac tggtgaccga tctgaccaaa gtgcataccg aatgctgcca tggcgatctg    840
ctggaatgcg cggatgatcg cgcggatctg gcgaaatata tttgcgaaaa ccaggatagc    900
attagcagca aactgaaaga atgctgcgaa aaaccgctgc tggaaaaaag ccattgcatt    960
gcggaagtgg aaaacgatga atgccggcg ctgtgcaccc cgagccgcga tctgccgagc   1020
ctggcggcgg attttgtgga aagcaaagat gtgtgcaaaa actatgcgga agcgaaagat   1080
gtgtttctgg gcatgtttct gtatgaatat gcgcgccgcc atccggatta tagcgtggtg   1140
ctgctgctgc gcctggcgaa aacctatgaa accacccctgg aaaaatgctg cgcggcggcg   1200
gatccgcatg aatgctatgc gaaagtgttt gatgaattta aaccgctggt ggaagaaccg   1260
cagaacctga ttaaacagaa ctgcgaactg tttgaacagc tgggcgaata taaatttcag   1320
aacgcgctgc tggtgcgcta taccaaaaaa gtgccgcagg tgagcacccc gaccctggtg   1380
gaagtgagcc gcaaacctgg gcaaagtggc agcaaatgct gcaaacatcc ggaagcgaaa   1440
cgcatgccgt gcgcggaaga ttatctgagc gtggtgctga accagctgtg cgtgctgcat   1500
gaaaaaaccc cggtgagcga tcgcgtgacc aaatgctgca ccgaaagcct ggtgaaccgc   1560
cgcccgtgct ttagcgcgct ggaagtggat gaaacctatg tgccgaaaga atttaacgcg   1620
gaaaccttta cctttcatgc ggatatttgc accctgagcg aaaaagaacg ccagattaaa   1680
aaacagaccg cgctggtgga actggtgaaa cataaaccga aagcgaccaa agaacagctg   1740
aaagcggtga tggatgattt tgcggcgttt gtggaaaaat gctgcaaagc ggatgataaa   1800
gaaacctgct ttgcggaaga aggcaaaaaa ctggtggcgg cgagccaggc ggcgctgggc   1860
ctgctgtgca ccccgagccg c                                              1881
```

<210> SEQ ID NO 82
<211> LENGTH: 235
<212> TYPE: PRT
<213> ORGANISM: Artificial Sequence
<220> FEATURE:
<223> OTHER INFORMATION: Synthetic peptide

<400> SEQUENCE: 82

```
Leu Cys Thr Pro Ser Arg Arg Ser Pro Pro Leu Lys Glu Cys Pro Pro
 1               5                  10                  15

Cys Ala Ala Pro Asp Leu Leu Gly Gly Pro Ser Val Phe Ile Phe Pro
            20                  25                  30

Pro Lys Ile Lys Asp Val Leu Met Ile Ser Leu Ser Pro Met Val Thr
        35                  40                  45

Cys Val Val Val Asp Val Ser Glu Asp Asp Pro Asp Val Gln Ile Ser
    50                  55                  60

Trp Phe Val Asn Asn Val Glu Val His Thr Ala Gln Thr Gln Thr His
65                  70                  75                  80

Arg Glu Asp Tyr Asn Ser Thr Leu Arg Val Val Ser Ala Leu Pro Ile
                85                  90                  95

Gln His Gln Asp Trp Met Ser Gly Lys Glu Phe Lys Cys Lys Val Asn
```

```
                    100                 105                 110
Asn Arg Ala Leu Pro Ser Pro Ile Glu Lys Thr Ile Ser Lys Pro Arg
            115                 120                 125

Gly Pro Val Arg Ala Pro Gln Val Tyr Val Leu Pro Pro Pro Ala Glu
        130                 135                 140

Glu Met Thr Lys Lys Glu Phe Ser Leu Thr Cys Met Ile Thr Gly Phe
145                 150                 155                 160

Leu Pro Ala Glu Ile Ala Val Asp Trp Thr Ser Asn Gly Arg Thr Glu
                165                 170                 175

Gln Asn Tyr Lys Asn Thr Ala Thr Val Leu Asp Ser Asp Gly Ser Tyr
            180                 185                 190

Phe Met Tyr Ser Lys Leu Arg Val Gln Lys Ser Thr Trp Glu Arg Gly
        195                 200                 205

Ser Leu Phe Ala Cys Ser Val Val His Glu Gly Leu His Asn His Leu
    210                 215                 220

Thr Thr Lys Thr Ile Ser Arg Ser Leu Gly Lys
225                 230                 235

<210> SEQ ID NO 83
<211> LENGTH: 235
<212> TYPE: PRT
<213> ORGANISM: Artificial Sequence
<220> FEATURE:
<223> OTHER INFORMATION: Synthetic peptide

<400> SEQUENCE: 83

Arg Ser Pro Pro Leu Lys Glu Cys Pro Cys Ala Ala Pro Asp Leu
1               5                  10                  15

Leu Gly Gly Pro Ser Val Phe Ile Phe Pro Pro Lys Ile Lys Asp Val
            20                  25                  30

Leu Met Ile Ser Leu Ser Pro Met Val Thr Cys Val Val Asp Val
        35                  40                  45

Ser Glu Asp Asp Pro Asp Val Gln Ile Ser Trp Phe Val Asn Asn Val
    50                  55                  60

Glu Val His Thr Ala Gln Thr Gln Thr His Arg Glu Asp Tyr Asn Ser
65                  70                  75                  80

Thr Leu Arg Val Val Ser Ala Leu Pro Ile Gln His Gln Asp Trp Met
                85                  90                  95

Ser Gly Lys Glu Phe Lys Cys Lys Val Asn Asn Arg Ala Leu Pro Ser
            100                 105                 110

Pro Ile Glu Lys Thr Ile Ser Lys Pro Arg Gly Pro Val Arg Ala Pro
        115                 120                 125

Gln Val Tyr Val Leu Pro Pro Pro Ala Glu Glu Met Thr Lys Lys Glu
    130                 135                 140

Phe Ser Leu Thr Cys Met Ile Thr Gly Phe Leu Pro Ala Glu Ile Ala
145                 150                 155                 160

Val Asp Trp Thr Ser Asn Gly Arg Thr Glu Gln Asn Tyr Lys Asn Thr
                165                 170                 175

Ala Thr Val Leu Asp Ser Asp Gly Ser Tyr Phe Met Tyr Ser Lys Leu
            180                 185                 190

Arg Val Gln Lys Ser Thr Trp Glu Arg Gly Ser Leu Phe Ala Cys Ser
        195                 200                 205

Val Val His Glu Gly Leu His Asn His Leu Thr Thr Lys Thr Ile Ser
    210                 215                 220

Arg Ser Leu Gly Lys Leu Cys Thr Pro Ser Arg
```

```
                225                 230                 235

<210> SEQ ID NO 84
<211> LENGTH: 245
<212> TYPE: PRT
<213> ORGANISM: Artificial Sequence
<220> FEATURE:
<223> OTHER INFORMATION: Synthetic peptide

<400> SEQUENCE: 84

Arg Ser Pro Pro Leu Lys Glu Cys Pro Pro Cys Ala Ala Pro Asp Leu
 1               5                   10                  15

Leu Gly Gly Pro Ser Val Phe Ile Phe Pro Pro Lys Ile Lys Asp Val
            20                  25                  30

Leu Met Ile Ser Leu Ser Pro Met Val Thr Cys Val Val Val Asp Val
        35                  40                  45

Ser Glu Asp Asp Pro Asp Val Gln Ile Ser Trp Phe Val Asn Asn Val
    50                  55                  60

Glu Val His Thr Ala Gln Thr Gln Thr His Arg Glu Asp Tyr Asn Ser
 65                  70                  75                  80

Thr Leu Arg Val Val Ser Ala Leu Pro Ile Gln His Gln Asp Trp Met
                85                  90                  95

Ser Gly Lys Glu Phe Lys Cys Lys Val Asn Asn Arg Ala Leu Pro Ser
            100                 105                 110

Pro Ile Glu Lys Thr Ile Ser Lys Pro Arg Gly Pro Val Arg Ala Pro
        115                 120                 125

Gln Val Tyr Val Leu Pro Pro Pro Ala Glu Glu Met Thr Lys Lys Glu
    130                 135                 140

Phe Ser Leu Thr Cys Met Ile Thr Gly Phe Leu Pro Ala Glu Ile Ala
145                 150                 155                 160

Val Asp Trp Thr Ser Asn Gly Arg Thr Glu Gln Asn Tyr Lys Asn Thr
                165                 170                 175

Ala Thr Val Leu Asp Ser Asp Gly Ser Tyr Phe Met Tyr Ser Lys Leu
            180                 185                 190

Arg Val Gln Lys Ser Thr Trp Glu Arg Gly Ser Leu Phe Ala Cys Ser
        195                 200                 205

Val Val His Glu Gly Leu His Asn His Leu Thr Thr Lys Thr Ile Ser
    210                 215                 220

Arg Ser Leu Gly Lys Leu Cys Thr Pro Ser Arg Gly Gly Gly Gly Leu
225                 230                 235                 240

Cys Thr Pro Ser Arg
                245

<210> SEQ ID NO 85
<211> LENGTH: 241
<212> TYPE: PRT
<213> ORGANISM: Artificial Sequence
<220> FEATURE:
<223> OTHER INFORMATION: Synthetic peptide

<400> SEQUENCE: 85

Leu Cys Thr Pro Ser Arg Arg Ser Pro Pro Leu Lys Glu Cys Pro Pro
 1               5                   10                  15

Cys Ala Ala Pro Asp Leu Leu Gly Gly Pro Ser Val Phe Ile Phe Pro
            20                  25                  30

Pro Lys Ile Lys Asp Val Leu Met Ile Ser Leu Ser Pro Met Val Thr
        35                  40                  45
```

```
Cys Val Val Asp Val Ser Glu Asp Pro Asp Val Gln Ile Ser
    50              55                  60

Trp Phe Val Asn Asn Val Glu Val His Thr Ala Gln Thr Gln Thr His
65                  70                  75                  80

Arg Glu Asp Tyr Asn Ser Thr Leu Arg Val Val Ser Ala Leu Pro Ile
                85                  90                  95

Gln His Gln Asp Trp Met Ser Gly Lys Glu Phe Lys Cys Lys Val Asn
                100                 105                 110

Asn Arg Ala Leu Pro Ser Pro Ile Glu Lys Thr Ile Ser Lys Pro Arg
            115                 120                 125

Gly Pro Val Arg Ala Pro Gln Val Tyr Val Leu Pro Pro Ala Glu
130                 135                 140

Glu Met Thr Lys Lys Glu Phe Ser Leu Thr Cys Met Ile Thr Gly Phe
145                 150                 155                 160

Leu Pro Ala Glu Ile Ala Val Asp Trp Thr Ser Asn Gly Arg Thr Glu
                165                 170                 175

Gln Asn Tyr Lys Asn Thr Ala Thr Val Leu Asp Ser Asp Gly Ser Tyr
                180                 185                 190

Phe Met Tyr Ser Lys Leu Arg Val Gln Lys Ser Thr Trp Glu Arg Gly
            195                 200                 205

Ser Leu Phe Ala Cys Ser Val Val His Glu Gly Leu His Asn His Leu
210                 215                 220

Thr Thr Lys Thr Ile Ser Arg Ser Leu Gly Lys Leu Cys Thr Pro Ser
225                 230                 235                 240

Arg

<210> SEQ ID NO 86
<211> LENGTH: 233
<212> TYPE: PRT
<213> ORGANISM: Artificial Sequence
<220> FEATURE:
<223> OTHER INFORMATION: Synthetic peptide

<400> SEQUENCE: 86

Leu Cys Thr Pro Ser Arg Asp Lys Thr His Thr Cys Pro Pro Cys Pro
1               5                   10                  15

Ala Pro Glu Leu Leu Gly Gly Pro Ser Val Phe Leu Phe Pro Pro Lys
            20                  25                  30

Pro Lys Asp Thr Leu Met Ile Ser Arg Thr Pro Glu Val Thr Cys Val
            35                  40                  45

Val Val Asp Val Ser His Glu Asp Pro Glu Val Lys Phe Asn Trp Tyr
    50                  55                  60

Val Asp Gly Val Glu Val His Asn Ala Lys Thr Lys Pro Arg Glu Glu
65                  70                  75                  80

Gln Tyr Asn Ser Thr Tyr Arg Val Val Ser Val Leu Thr Val Leu His
                85                  90                  95

Gln Asp Trp Leu Asn Gly Lys Glu Tyr Lys Cys Lys Val Ser Asn Lys
            100                 105                 110

Ala Leu Pro Ala Pro Ile Glu Lys Thr Ile Ser Lys Ala Lys Gly Gln
            115                 120                 125

Pro Arg Glu Pro Gln Val Tyr Thr Leu Pro Pro Ser Arg Glu Glu Met
        130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
```

```
                165                 170                 175
Tyr Lys Thr Thr Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
            195                 200                 205

Phe Ser Cys Ser Val Met His Glu Gly Leu His Asn His Tyr Thr Gln
210                 215                 220

Lys Ser Leu Ser Leu Ser Pro Gly Lys
225                 230

<210> SEQ ID NO 87
<211> LENGTH: 233
<212> TYPE: PRT
<213> ORGANISM: Artificial Sequence
<220> FEATURE:
<223> OTHER INFORMATION: Synthetic peptide

<400> SEQUENCE: 87

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Gly Leu His Asn His Tyr Thr Gln Lys Ser Leu Ser Leu Ser
    210                 215                 220

Pro Gly Lys Leu Cys Thr Pro Ser Arg
225                 230

<210> SEQ ID NO 88
<211> LENGTH: 243
<212> TYPE: PRT
<213> ORGANISM: Artificial Sequence
<220> FEATURE:
<223> OTHER INFORMATION: Synthetic peptide

<400> SEQUENCE: 88
```

```
Asp Lys Thr His Thr Cys Pro Pro Cys Pro Ala Pro Glu Leu Leu Gly
  1               5                  10                  15
Gly Pro Ser Val Phe Leu Phe Pro Pro Lys Pro Lys Asp Thr Leu Met
             20                  25                  30
Ile Ser Arg Thr Pro Glu Val Thr Cys Val Val Val Asp Val Ser His
         35                  40                  45
Glu Asp Pro Glu Val Lys Phe Asn Trp Tyr Val Asp Gly Val Glu Val
 50                  55                  60
His Asn Ala Lys Thr Lys Pro Arg Glu Glu Gln Tyr Asn Ser Thr Tyr
 65                  70                  75                  80
Arg Val Val Ser Val Leu Thr Val Leu His Gln Asp Trp Leu Asn Gly
                 85                  90                  95
Lys Glu Tyr Lys Cys Lys Val Ser Asn Lys Ala Leu Pro Ala Pro Ile
             100                 105                 110
Glu Lys Thr Ile Ser Lys Ala Lys Gly Gln Pro Arg Glu Pro Gln Val
             115                 120                 125
Tyr Thr Leu Pro Pro Ser Arg Glu Glu Met Thr Lys Asn Gln Val Ser
         130                 135                 140
Leu Thr Cys Leu Val Lys Gly Phe Tyr Pro Ser Asp Ile Ala Val Glu
145                 150                 155                 160
Trp Glu Ser Asn Gly Gln Pro Glu Asn Asn Tyr Lys Thr Thr Pro Pro
                 165                 170                 175
Val Leu Asp Ser Asp Gly Ser Phe Phe Leu Tyr Ser Lys Leu Thr Val
             180                 185                 190
Asp Lys Ser Arg Trp Gln Gln Gly Asn Val Phe Ser Cys Ser Val Met
             195                 200                 205
His Glu Gly Leu His Asn His Tyr Thr Gln Lys Ser Leu Ser Leu Ser
         210                 215                 220
Pro Gly Lys Leu Cys Thr Pro Ser Arg Gly Gly Gly Leu Cys Thr
225                 230                 235                 240
Pro Ser Arg

<210> SEQ ID NO 89
<211> LENGTH: 239
<212> TYPE: PRT
<213> ORGANISM: Artificial Sequence
<220> FEATURE:
<223> OTHER INFORMATION: Synthetic peptide

<400> SEQUENCE: 89

Leu Cys Thr Pro Ser Arg Asp Lys Thr His Thr Cys Pro Pro Cys Pro
  1               5                  10                  15
Ala Pro Glu Leu Leu Gly Gly Pro Ser Val Phe Leu Phe Pro Pro Lys
             20                  25                  30
Pro Lys Asp Thr Leu Met Ile Ser Arg Thr Pro Glu Val Thr Cys Val
         35                  40                  45
Val Val Asp Val Ser His Glu Asp Pro Glu Val Lys Phe Asn Trp Tyr
 50                  55                  60
Val Asp Gly Val Glu Val His Asn Ala Lys Thr Lys Pro Arg Glu Glu
 65                  70                  75                  80
Gln Tyr Asn Ser Thr Tyr Arg Val Val Ser Val Leu Thr Val Leu His
                 85                  90                  95
Gln Asp Trp Leu Asn Gly Lys Glu Tyr Lys Cys Lys Val Ser Asn Lys
             100                 105                 110
Ala Leu Pro Ala Pro Ile Glu Lys Thr Ile Ser Lys Ala Lys Gly Gln
```

```
            115                 120                 125
Pro Arg Glu Pro Gln Val Tyr Thr Leu Pro Pro Ser Arg Glu Glu Met
    130                 135                 140

Thr Lys Asn Gln Val Ser Leu Thr Cys Leu Val Lys Gly Phe Tyr Pro
145                 150                 155                 160

Ser Asp Ile Ala Val Glu Trp Glu Ser Asn Gly Gln Pro Glu Asn Asn
                165                 170                 175

Tyr Lys Thr Thr Pro Pro Val Leu Asp Ser Asp Gly Ser Phe Phe Leu
            180                 185                 190

Tyr Ser Lys Leu Thr Val Asp Lys Ser Arg Trp Gln Gln Gly Asn Val
        195                 200                 205

Phe Ser Cys Ser Val Met His Glu Gly Leu His Asn His Tyr Thr Gln
    210                 215                 220

Lys Ser Leu Ser Leu Ser Pro Gly Lys Leu Cys Thr Pro Ser Arg
225                 230                 235

<210> SEQ ID NO 90
<211> LENGTH: 5
<212> TYPE: PRT
<213> ORGANISM: Artificial Sequence
<220> FEATURE:
<223> OTHER INFORMATION: Synthetic peptide

<400> SEQUENCE: 90

Gly Ser Gly Gly Ser
 1               5

<210> SEQ ID NO 91
<211> LENGTH: 4
<212> TYPE: PRT
<213> ORGANISM: Artificial Sequence
<220> FEATURE:
<223> OTHER INFORMATION: Synthetic peptide

<400> SEQUENCE: 91

Gly Gly Gly Ser
 1

<210> SEQ ID NO 92
<211> LENGTH: 5
<212> TYPE: PRT
<213> ORGANISM: Artificial Sequence
<220> FEATURE:
<223> OTHER INFORMATION: Synthetic peptide

<400> SEQUENCE: 92

Gly Gly Ser Gly Gly
 1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic peptide

<400> SEQUENCE: 93

Gly Ser Gly Ser Gly
 1               5

<210> SEQ ID NO 94
<211> LENGTH: 5
<212> TYPE: PRT
```

```
<213> ORGANISM: Artificial Sequence
<220> FEATURE:
<223> OTHER INFORMATION: Synthetic peptide

<400> SEQUENCE: 94

Gly Ser Gly Gly Gly
 1               5

<210> SEQ ID NO 95
<211> LENGTH: 5
<212> TYPE: PRT
<213> ORGANISM: Artificial Sequence
<220> FEATURE:
<223> OTHER INFORMATION: Synthetic peptide

<400> SEQUENCE: 95

Gly Gly Gly Ser Gly
 1               5

<210> SEQ ID NO 96
<211> LENGTH: 5
<212> TYPE: PRT
<213> ORGANISM: Artificial Sequence
<220> FEATURE:
<223> OTHER INFORMATION: Synthetic peptide

<400> SEQUENCE: 96

Gly Ser Ser Ser Gly
 1               5

<210> SEQ ID NO 97
<211> LENGTH: 16
<212> TYPE: PRT
<213> ORGANISM: Artificial Sequence
<220> FEATURE:
<223> OTHER INFORMATION: Synthetic peptide

<400> SEQUENCE: 97

Leu Cys Thr Pro Ser Arg Gly Gly Gly Gly Leu Cys Thr Pro Ser Arg
 1               5                  10                  15

<210> SEQ ID NO 98
<211> LENGTH: 34
<212> TYPE: DNA
<213> ORGANISM: Artificial Sequence
<220> FEATURE:
<223> OTHER INFORMATION: Synthetic primer

<400> SEQUENCE: 98
aatcccggga tgaagtgggt aacctttatt tccc                               34

<210> SEQ ID NO 99
<211> LENGTH: 35
<212> TYPE: DNA
<213> ORGANISM: Artificial Sequence
<220> FEATURE:
<223> OTHER INFORMATION: Synthetic primer

<400> SEQUENCE: 99
tgactcgagt tataagccta aggcagcttg acttg                              35

<210> SEQ ID NO 100
<211> LENGTH: 1843
<212> TYPE: DNA
<213> ORGANISM: Artificial Sequence
<220> FEATURE:
<223> OTHER INFORMATION: Synthetic nucleotide
```

<400> SEQUENCE: 100

```
aatcccggga tgaagtgggt aacctttatt tcccttcttt ttctctttag ctcggcttat    60
tccaggggtg tgtttcgtcg agatgcacac aagagtgagg ttgctcatcg gtttaaagat   120
ttgggagaag aaaatttcaa agccttggtg ttgattgcct ttgctcagta tcttcagcag   180
tgtccatttg aagatcatgt aaaattagtg aatgaagtaa ctgaatttgc aaaaacatgt   240
gttgctgatg agtcagctga aaattgtgac aaatcacttc atacccttttt tggagacaaa   300
ttatgcacag ttgcaactct tcgtgaaacc tatggtgaaa tggctgactg ctgtgcaaaa   360
caagaacctg agagaaatga atgcttcttg caacacaaag atgacaaccc aaacctcccc   420
cgattggtga gaccagaggt tgatgtgatg tgcactgctt tcatgacaa tgaagagaca    480
ttttgaaaaa aatacttata tgaaattgcc agaagacatc cttacttta tgccccggaa    540
ctccttttct ttgctaaaag gtataaagct gcttttacag aatgttgcca agctgctgat    600
aaagctgcct gcctgttgcc aaagctcgat gaacttcggg atgaagggaa ggcttcgtct   660
gccaaacaga gactcaagtg tgccagtctc caaaaatttg agaaagagc tttcaaagca    720
tgggcagtag ctcgcctgag ccagagattt cccaaagctg agtttgcaga gtttccaag    780
ttagtgacag atcttaccaa agtccacacg gaatgctgcc atggagatct gcttgaatgt   840
gctgatgaca gggcggacct tgccaagtat atctgtgaaa atcaagattc gatctccagt   900
aaactgaagg aatgctgtga aaaacctctg ttggaaaaat cccactgcat tgccgaagtg   960
gaaaatgatg agatgcctgc tgacttgcct tcattagctg ctgattttgt tgaaagtaag  1020
gatgtttgca aaactatgc tgaggcaaag gatgtcttcc tgggcatgtt tttgtatgaa  1080
tatgcaagaa ggcatcctga ttactctgtc gtgctgctgc tgagacttgc caagacatat  1140
gaaaccactc tagagaagtg ctgtgccgct gcagatcctc atgaatgcta tgccaaagtg  1200
ttcgatgaat ttaaacctct tgtggaagag cctcagaatt taatcaaaca aaattgtgag  1260
cttttttgagc agcttggaga gtacaaattc cagaatgcgc tattagttcg ttacaccaag  1320
aaagtacccc aagtgtcaac tccaactctt gtagaggtct caagaaacct aggaaaagtg  1380
ggcagcaaat gttgtaaaca tcctgaagca aaaagaatgc cctgtgcaga agactatcta  1440
tccgtggtcc tgaaccagtt atgtgtgttg catgagaaaa cgccagtaag tgacagagtc  1500
accaaatgct gcacagaatc cttggtgaac aggcgaccat gcttttcagc tctgaaagtc  1560
gatgaaacat acgttcccaa agagtttaat gctgaaacat tcaccttcca tgcagatata  1620
tgcacactt ctgagaagga gagacaaatc aagaaacaaa ctgcacttgt tgagctcgtg  1680
aaacacaagc ccaaggcaac aaaagagcaa ctgaaagctg ttatggatga tttcgcagct  1740
tttgtagaga agtgctgcaa ggctgacgat aaggagacct gctttgccga ggagggtaaa  1800
aaacttgttg ctgcaagtca agctgcctta ggcttaactc gag                    1843
```

<210> SEQ ID NO 101
<211> LENGTH: 614
<212> TYPE: PRT
<213> ORGANISM: Artificial Sequence
<220> FEATURE:
<223> OTHER INFORMATION: Synthetic peptide

<400> SEQUENCE: 101

```
Asn Pro Gly Met Lys Trp Val Thr Phe Ile Ser Leu Leu Phe Leu Phe
  1               5                  10                  15

Ser Ser Ala Tyr Ser Arg Gly Val Phe Arg Arg Asp Ala His Lys Ser
```

-continued

```
                20                  25                  30
Glu Val Ala His Arg Phe Lys Asp Leu Gly Glu Glu Asn Phe Lys Ala
            35                  40                  45
Leu Val Leu Ile Ala Phe Ala Gln Tyr Leu Gln Gln Cys Pro Phe Glu
        50                  55                  60
Asp His Val Lys Leu Val Asn Glu Val Thr Glu Phe Ala Lys Thr Cys
65                  70                  75                  80
Val Ala Asp Glu Ser Ala Glu Asn Cys Asp Lys Ser Leu His Thr Leu
                85                  90                  95
Phe Gly Asp Lys Leu Cys Thr Val Ala Thr Leu Arg Glu Thr Tyr Gly
            100                 105                 110
Glu Met Ala Asp Cys Cys Ala Lys Gln Glu Pro Glu Arg Asn Glu Cys
        115                 120                 125
Phe Leu Gln His Lys Asp Asp Asn Pro Asn Leu Pro Arg Leu Val Arg
        130                 135                 140
Pro Glu Val Asp Val Met Cys Thr Ala Phe His Asp Asn Glu Glu Thr
145                 150                 155                 160
Phe Leu Lys Lys Tyr Leu Tyr Glu Ile Ala Arg Arg His Pro Tyr Phe
            165                 170                 175
Tyr Ala Pro Glu Leu Leu Phe Phe Ala Lys Arg Tyr Lys Ala Ala Phe
            180                 185                 190
Thr Glu Cys Cys Gln Ala Ala Asp Lys Ala Ala Cys Leu Leu Pro Lys
        195                 200                 205
Leu Asp Glu Leu Arg Asp Glu Gly Lys Ala Ser Ser Ala Lys Gln Arg
        210                 215                 220
Leu Lys Cys Ala Ser Leu Gln Lys Phe Gly Glu Arg Ala Phe Lys Ala
225                 230                 235                 240
Trp Ala Val Ala Arg Leu Ser Gln Arg Phe Pro Lys Ala Glu Phe Ala
            245                 250                 255
Glu Val Ser Lys Leu Val Thr Asp Leu Thr Lys Val His Thr Glu Cys
            260                 265                 270
Cys His Gly Asp Leu Leu Glu Cys Ala Asp Asp Arg Ala Asp Leu Ala
        275                 280                 285
Lys Tyr Ile Cys Glu Asn Gln Asp Ser Ile Ser Ser Lys Leu Lys Glu
        290                 295                 300
Cys Cys Glu Lys Pro Leu Leu Glu Lys Ser His Cys Ile Ala Glu Val
305                 310                 315                 320
Glu Asn Asp Glu Met Pro Ala Asp Leu Pro Ser Leu Ala Ala Asp Phe
            325                 330                 335
Val Glu Ser Lys Asp Val Cys Lys Asn Tyr Ala Glu Ala Lys Asp Val
            340                 345                 350
Phe Leu Gly Met Phe Leu Tyr Glu Tyr Ala Arg Arg His Pro Asp Tyr
        355                 360                 365
Ser Val Val Leu Leu Leu Arg Leu Ala Lys Thr Tyr Glu Thr Thr Leu
        370                 375                 380
Glu Lys Cys Cys Ala Ala Ala Asp Pro His Glu Cys Tyr Ala Lys Val
385                 390                 395                 400
Phe Asp Glu Phe Lys Pro Leu Val Glu Glu Pro Gln Asn Leu Ile Lys
            405                 410                 415
Gln Asn Cys Glu Leu Phe Glu Gln Leu Gly Glu Tyr Lys Phe Gln Asn
            420                 425                 430
Ala Leu Leu Val Arg Tyr Thr Lys Lys Val Pro Gln Val Ser Thr Pro
        435                 440                 445
```

Thr Leu Val Glu Val Ser Arg Asn Leu Gly Lys Val Gly Ser Lys Cys
    450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
                500                 505                 510

Pro Cys Phe Ser Ala Leu Glu Val Asp Glu Thr Tyr Val Pro Lys Glu
            515                 520                 525

Phe Asn Ala Glu Thr Phe Thr Phe His Ala Asp Ile Cys Thr Leu Ser
        530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
                580                 585                 590

Thr Cys Phe Ala Glu Glu Gly Lys Lys Leu Val Ala Ala Ser Gln Ala
            595                 600                 605

Ala Leu Gly Leu Thr Arg
    610

<210> SEQ ID NO 102
<211> LENGTH: 50
<212> TYPE: DNA
<213> ORGANISM: Artificial Sequence
<220> FEATURE:
<223> OTHER INFORMATION: Synthetic primer

<400> SEQUENCE: 102
atactcgagt tagtcgactt caagctttaa gcctaaggca gcttgacttg           50

<210> SEQ ID NO 103
<211> LENGTH: 1863
<212> TYPE: DNA
<213> ORGANISM: Artificial Sequence
<220> FEATURE:
<223> OTHER INFORMATION: Synthetic nucleotide

<400> SEQUENCE: 103
aatcccggga tgaagtgggt aacctttatt tcccttcttt ttctctttag ctcggcttat    60 tccagggtg tgtttcgtcg agatgcacac aagagtgagg ttgctcatcg gtttaaagat    120 ttggagaag aaaatttcaa agccttggtg ttgattgcct tgctcagta tcttcagcag    180 tgtccatttg aagatcatgt aaaattagtg aatgaagtaa ctgaatttgc aaaaacatgt    240
gttgctgatg agtcagctga aaattgtgac aaatcacttc ataccctttt tggagacaaa    300
ttatgcacag ttgcaactct tcgtgaaacc atggtgaaa tggctgactg ctgtgcaaaa    360
caagaacctg agagaaatga atgcttcttg caacacaaag atgacaaccc aaacctcccc    420
cgattggtga ccagaggt tgatgtgatg tgcactgctt tcatgacaa tgaagagaca    480 tttttgaaaa atacttata tgaaattgcc agaagacatc cttacttta tgccccggaa    540 ctccttttct tgctaaaag gtataaagct gcttttacag aatgttgcca agctgctgat    600
aaagctgcct gcctgttgcc aaagctcgat gaacttcggg atgaagggaa ggcttcgtct    660
gccaaacaga gactcaagtg tgccagtctc caaaaatttg gagaaagagc tttcaaagca    720

```
tgggcagtag ctcgcctgag ccagagattt cccaaagctg agtttgcaga agtttccaag      780
ttagtgacag atcttaccaa agtccacacg gaatgctgcc atggagatct gcttgaatgt      840
gctgatgaca gggcggacct tgccaagtat atctgtgaaa atcaagattc gatctccagt      900
aaactgaagg aatgctgtga aaaacctctg ttggaaaaat cccactgcat tgccgaagtg      960
gaaaatgatg agatgcctgc tgacttgcct tcattagctg ctgattttgt tgaaagtaag     1020
gatgtttgca aaaactatgc tgaggcaaag gatgtcttcc tgggcatgtt tttgtatgaa     1080
tatgcaagaa ggcatcctga ttactctgtc gtgctgctgc tgagacttgc caagacatat     1140
gaaaccactc tagagaagtg ctgtgccgct gcagatcctc atgaatgcta tgccaaagtg     1200
ttcgatgaat ttaaacctct tgtggaagag cctcagaatt aatcaaaca aaattgtgag     1260 cttttttgagc agcttggaga gtacaaattc agaatgcgc tattagttcg ttacaccaag     1320
aaagtacccc aagtgtcaac tccaactctt gtagaggtct caagaaacct aggaaaagtg     1380
ggcagcaaat gttgtaaaca tcctgaagca aaagaatgc cctgtgcaga agactatcta     1440
tccgtggtcc tgaaccagtt atgtgtgttg catgagaaaa cgccagtaag tgacagagtc     1500
accaaatgct gcacagaatc cttggtgaac aggcgaccat gcttttcagc tctggaagtc     1560
gatgaaacat acgttcccaa agagtttaat gctgaaacat tcaccttcca tgcagatata     1620
tgcacacttt ctgagaagga gagacaaatc aagaaacaaa ctgcacttgt tgagctcgtg     1680
aaacacaagc ccaaggcaac aaaagagcaa ctgaaagctg ttatggatga tttcgcagct     1740
tttgtagaga agtgctgcaa ggctgacgat aaggagacct gctttgccga ggagggtaaa     1800
aaacttgttg ctgcaagtca agctgcctta ggcttaaagc ttgaagtcga ctaactcgag     1860
ata                                                                  1863
```

<210> SEQ ID NO 104
<211> LENGTH: 620
<212> TYPE: PRT
<213> ORGANISM: Artificial Sequence
<220> FEATURE:
<223> OTHER INFORMATION: Synthetic peptide

<400> SEQUENCE: 104

```
Asn Pro Gly Met Lys Trp Val Thr Phe Ile Ser Leu Leu Phe Leu Phe
 1               5                  10                  15

Ser Ser Ala Tyr Ser Arg Gly Val Phe Arg Arg Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
```

-continued

```
        145                 150                 155                 160
    Phe Leu Lys Lys Tyr Leu Tyr Glu Ile Ala Arg Arg His Pro Tyr Phe
                    165                 170                 175

Tyr Ala Pro Glu Leu Leu Phe Phe Ala Lys Arg Tyr Lys Ala Ala Phe
                    180                 185                 190

Thr Glu Cys Cys Gln Ala Ala Asp Lys Ala Ala Cys Leu Leu Pro Lys
                    195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
    225                 230                 235                 240

Trp Ala Val Ala Arg Leu Ser Gln Arg Phe Pro Lys Ala Glu Phe Ala
                    245                 250                 255

Glu Val Ser Lys Leu Val Thr Asp Leu Thr Lys Val His Thr Glu Cys
                    260                 265                 270

Cys His Gly Asp Leu Leu Glu Cys Ala Asp Asp Arg Ala Asp Leu Ala
                    275                 280                 285

Lys Tyr Ile Cys Glu Asn Gln Asp Ser Ile Ser Ser Lys Leu Lys Glu
                    290                 295                 300

Cys Cys Glu Lys Pro Leu Leu Glu Lys Ser His Cys Ile Ala Glu Val
    305                 310                 315                 320

Glu Asn Asp Glu Met Pro Ala Asp Leu Pro Ser Leu Ala Ala Asp Phe
                    325                 330                 335

Val Glu Ser Lys Asp Val Cys Lys Asn Tyr Ala Glu Ala Lys Asp Val
                    340                 345                 350

Phe Leu Gly Met Phe Leu Tyr Glu Tyr Ala Arg Arg His Pro Asp Tyr
                    355                 360                 365

Ser Val Val Leu Leu Arg Leu Ala Lys Thr Tyr Glu Thr Thr Leu
                    370                 375                 380

Glu Lys Cys Cys Ala Ala Ala Asp Pro His Glu Cys Tyr Ala Lys Val
    385                 390                 395                 400

Phe Asp Glu Phe Lys Pro Leu Val Glu Glu Pro Gln Asn Leu Ile Lys
                    405                 410                 415

Gln Asn Cys Glu Leu Phe Glu Gln Leu Gly Glu Tyr Lys Phe Gln Asn
                    420                 425                 430

Ala Leu Leu Val Arg Tyr Thr Lys Lys Val Pro Gln Val Ser Thr Pro
                    435                 440                 445

Thr Leu Val Glu Val Ser Arg Asn Leu Gly Lys Val Gly Ser Lys Cys
    450                 455                 460

Cys Lys His Pro Glu Ala Lys Arg Met Pro Cys Ala Glu Asp Tyr Leu
    465                 470                 475                 480

Ser Val Val Leu Asn Gln Leu Cys Val Leu His Glu Lys Thr Pro Val
                    485                 490                 495

Ser Asp Arg Val Thr Lys Cys Cys Thr Glu Ser Leu Val Asn Arg Arg
                    500                 505                 510

Pro Cys Phe Ser Ala Leu Glu Val Asp Glu Thr Tyr Val Pro Lys Glu
                    515                 520                 525

Phe Asn Ala Glu Thr Phe Thr Phe His Ala Asp Ile Cys Thr Leu Ser
                    530                 535                 540

Glu Lys Glu Arg Gln Ile Lys Lys Gln Thr Ala Leu Val Glu Leu Val
    545                 550                 555                 560

Lys His Lys Pro Lys Ala Thr Lys Glu Gln Leu Lys Ala Val Met Asp
                    565                 570                 575
```

```
Asp Phe Ala Ala Phe Val Glu Lys Cys Cys Lys Ala Asp Asp Lys Glu
        580                 585                 590

Thr Cys Phe Ala Glu Glu Gly Lys Lys Leu Val Ala Ala Ser Gln Ala
    595                 600                 605

Ala Leu Gly Leu Lys Leu Glu Val Asp Leu Glu Ile
    610                 615                 620

<210> SEQ ID NO 105
<211> LENGTH: 1839
<212> TYPE: DNA
<213> ORGANISM: Artificial Sequence
<220> FEATURE:
<223> OTHER INFORMATION: Synthetic nucleotide

<400> SEQUENCE: 105
```

| | | | |
|---|---|---|---|
| aacccgggca tgaaatgggt gacctttatt agcctgctgt tctgtttag cagcgcgtat | 60 |
| agccgcggcg tgtttcgccg cgatgcgcat aaaagcgaag tggcgcatcg ctttaaagat | 120 |
| ctgggcgaag aaaactttaa agcgctggtg ctgattgcgt tgcgcagta tctgcagcag | 180 |
| tgcccgtttg aagatcatgt gaaactggtg aacgaagtga ccgaatttgc gaaaacctgc | 240 |
| gtggcggatg aaagcgcgga aaactgcgat aaagcctgc ataccctgtt tggcgataaa | 300 |
| ctgtgcaccg tggcgaccct gcgcgaaacc tatggcgaaa tggcggattg ctgcgcgaaa | 360 |
| caggaaccgg aacgcaacga atgctttctg cagcataaag atgataaccc gaacctgccg | 420 |
| cgcctggtgc gcccggaagt ggatgtgatg tgcaccgcgt tcatgataa cgaagaaacc | 480 |
| tttctgaaaa aatatctgta tgaaattgcg cgccgccatc cgtatttta tgcgccggaa | 540 |
| ctgctgtttt ttgcgaaacg ctataaagcg gcgtttaccg aatgctgcca ggcggcggat | 600 |
| aaagcggcgt gcctgctgcc gaaactggat gaactgcgcg atgaaggcaa agcgagcagc | 660 |
| gcgaaacagc gcctgaaatg cgcgagcctg cagaaatttg gcgaacgcgc gtttaaagcg | 720 |
| tgggcggtgg cgcgcctgag ccagcgcttt ccgaaagcgg aatttgcgga agtgagcaaa | 780 |
| ctggtgaccg atctgaccaa agtgcatacc gaatgctgcc atggcgatct gctggaatgc | 840 |
| gcggatgatc gcgcggatct ggcgaaatat atttgcgaaa accaggatag cattagcagc | 900 |
| aaactgaaag aatgctgcga aaaaccgctg ctggaaaaaa gccattgcat tgcggaagtg | 960 |
| gaaaacgatg aaatgccggc ggatctgccg agcctggcgg cggattttgt ggaaagcaaa | 1020 |
| gatgtgtgca aaaactatgc ggaagcgaaa gatgtgtttc tgggcatgtt tctgtatgaa | 1080 |
| tatgcgcgcc gccatccgga ttatagcgtg gtgctgctgc tgcgcctggc gaaaacctat | 1140 |
| gaaaccaccc tggaaaaatg ctgcgcggcg gcggatccgc atgaatgcta tgcgaaagtg | 1200 |
| tttgatgaat taaaccgct ggtggaagaa ccgcagaacc tgattaaaca gaactgcgaa | 1260 |
| ctgtttgaac agctgggcga atataaattt cagaacgcgc tgctggtgcg ctataccaaa | 1320 |
| aaagtgccgc aggtgagcac cccgaccctg gtggaagtga ccgcaacct gggcaaagtg | 1380 |
| ggcagcaaat gctgcaaaca tccggaagcg aaacgcatgc cgtgcgcgga agattatctg | 1440 |
| agcgtggtgc tgaaccagct gtgcgtgctg catgaaaaaa ccccggtgag cgatcgcgtg | 1500 |
| accaaatgct gcaccgaaag cctggtgaac cgccgcccgt gctttagcgc gctggaagtg | 1560 |
| gatgaaacct atgtgccgaa agaatttaac gcggaaacct ttaccttta tgcggatatt | 1620 |
| tgcaccctga gcgaaaaaga acgccagatt aaaaaacaga ccgcgctggt ggaactggtg | 1680 |
| aaacataaac cgaaagcgac caagaacag ctgaaagcgg tgatggatga ttttgcggcg | 1740 |
| tttgtggaaa aatgctgcaa agcggatgat aaagaaacct gctttgcgga agaaggcaaa | 1800 | aaactgctgt gcaccccgag ccgcgtggat ctggaaatt           1839

<210> SEQ ID NO 106
<211> LENGTH: 613
<212> TYPE: PRT
<213> ORGANISM: Artificial Sequence
<220> FEATURE:
<223> OTHER INFORMATION: Synthetic peptide

<400> SEQUENCE: 106

```
Asn Pro Gly Met Lys Trp Val Thr Phe Ile Ser Leu Leu Phe Leu Phe
 1               5                  10                  15

Ser Ser Ala Tyr Ser Arg Gly Val Phe Arg Arg Asp Ala His Lys Ser
            20                  25                  30

Glu Val Ala His Arg Phe Lys Asp Leu Gly Glu Glu Asn Phe Lys Ala
        35                  40                  45

Leu Val Leu Ile Ala Phe Ala Gln Tyr Leu Gln Gln Cys Pro Phe Glu
    50                  55                  60

Asp His Val Lys Leu Val Asn Glu Val Thr Glu Phe Ala Lys Thr Cys
65                  70                  75                  80

Val Ala Asp Glu Ser Ala Glu Asn Cys Asp Lys Ser Leu His Thr Leu
                85                  90                  95

Phe Gly Asp Lys Leu Cys Thr Val Ala Thr Leu Arg Glu Thr Tyr Gly
            100                 105                 110

Glu Met Ala Asp Cys Cys Ala Lys Gln Glu Pro Glu Arg Asn Glu Cys
        115                 120                 125

Phe Leu Gln His Lys Asp Asp Asn Pro Asn Leu Pro Arg Leu Val Arg
    130                 135                 140

Pro Glu Val Asp Val Met Cys Thr Ala Phe His Asp Asn Glu Glu Thr
145                 150                 155                 160

Phe Leu Lys Lys Tyr Leu Tyr Glu Ile Ala Arg Arg His Pro Tyr Phe
                165                 170                 175

Tyr Ala Pro Glu Leu Leu Phe Phe Ala Lys Arg Tyr Lys Ala Ala Phe
            180                 185                 190

Thr Glu Cys Cys Gln Ala Ala Asp Lys Ala Ala Cys Leu Leu Pro Lys
        195                 200                 205

Leu Asp Glu Leu Arg Asp Glu Gly Lys Ala Ser Ser Ala Lys Gln Arg
    210                 215                 220

Leu Lys Cys Ala Ser Leu Gln Lys Phe Gly Glu Arg Ala Phe Lys Ala
225                 230                 235                 240

Trp Ala Val Ala Arg Leu Ser Gln Arg Phe Pro Lys Ala Glu Phe Ala
                245                 250                 255

Glu Val Ser Lys Leu Val Thr Asp Leu Thr Lys Val His Thr Glu Cys
            260                 265                 270

Cys His Gly Asp Leu Leu Glu Cys Ala Asp Asp Arg Ala Asp Leu Ala
        275                 280                 285

Lys Tyr Ile Cys Glu Asn Gln Asp Ser Ile Ser Ser Lys Leu Lys Glu
    290                 295                 300

Cys Cys Glu Lys Pro Leu Leu Glu Lys Ser His Cys Ile Ala Glu Val
305                 310                 315                 320

Glu Asn Asp Glu Met Pro Ala Asp Leu Pro Ser Leu Ala Ala Asp Phe
                325                 330                 335

Val Glu Ser Lys Asp Val Cys Lys Asn Tyr Ala Glu Ala Lys Asp Val
            340                 345                 350
```

```
Phe Leu Gly Met Phe Leu Tyr Glu Tyr Ala Arg Arg His Pro Asp Tyr
            355                 360                 365

Ser Val Val Leu Leu Arg Leu Ala Lys Thr Tyr Glu Thr Thr Leu
    370                 375                 380

Glu Lys Cys Cys Ala Ala Asp Pro His Glu Cys Tyr Ala Lys Val
385                 390                 395                 400

Phe Asp Glu Phe Lys Pro Leu Val Glu Glu Pro Gln Asn Leu Ile Lys
                405                 410                 415

Gln Asn Cys Glu Leu Phe Glu Gln Leu Gly Glu Tyr Lys Phe Gln Asn
                420                 425                 430

Ala Leu Leu Val Arg Tyr Thr Lys Lys Val Pro Gln Val Ser Thr Pro
            435                 440                 445

Thr Leu Val Glu Val Ser Arg Asn Leu Gly Lys Val Gly Ser Lys Cys
            450                 455                 460

Cys Lys His Pro Glu Ala Lys Arg Met Pro Cys Ala Glu Asp Tyr Leu
465                 470                 475                 480

Ser Val Val Leu Asn Gln Leu Cys Val Leu His Glu Lys Thr Pro Val
                485                 490                 495

Ser Asp Arg Val Thr Lys Cys Cys Thr Glu Ser Leu Val Asn Arg Arg
                500                 505                 510

Pro Cys Phe Ser Ala Leu Glu Val Asp Glu Thr Tyr Val Pro Lys Glu
            515                 520                 525

Phe Asn Ala Glu Thr Phe Thr Phe His Ala Asp Ile Cys Thr Leu Ser
            530                 535                 540

Glu Lys Glu Arg Gln Ile Lys Lys Gln Thr Ala Leu Val Glu Leu Val
545                 550                 555                 560

Lys His Lys Pro Lys Ala Thr Lys Glu Gln Leu Lys Ala Val Met Asp
                565                 570                 575

Asp Phe Ala Ala Phe Val Glu Lys Cys Cys Lys Ala Asp Asp Lys Glu
                580                 585                 590

Thr Cys Phe Ala Glu Glu Gly Lys Lys Leu Leu Cys Thr Pro Ser Arg
            595                 600                 605

Val Asp Leu Glu Ile
    610

<210> SEQ ID NO 107
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: UNSURE
<222> LOCATION: (12)...(13)
<223> OTHER INFORMATION: PstI ligation site

<400> SEQUENCE: 107

Leu Cys Thr Pro Ser Arg Leu Val Pro Arg Gly Ser His His His
 1               5                  10                  15

His His

<210> SEQ ID NO 108
<211> LENGTH: 66
<212> TYPE: DNA
<213> ORGANISM: Artificial Sequence
<220> FEATURE:
<223> OTHER INFORMATION: Synthetic primer

<400> SEQUENCE: 108
```
agcttctttg taccccctagc aggctggtgc cgcgcggcag cctgcagcat catcaccacc    60
atcacg    66

<210> SEQ ID NO 109
<211> LENGTH: 66
<212> TYPE: DNA
<213> ORGANISM: Artificial Sequence
<220> FEATURE:
<223> OTHER INFORMATION: Synthetic primer

<400> SEQUENCE: 109
agaaacatgg ggatcgtccg accacggcgc gccgtcggac gtcgtagtag tggtggtagt    60
gcagct    66

<210> SEQ ID NO 110
<211> LENGTH: 632
<212> TYPE: PRT
<213> ORGANISM: Artificial Sequence
<220> FEATURE:
<223> OTHER INFORMATION: Synthetic peptide

<400> SEQUENCE: 110

Met Lys Trp Thr Phe Ile Ser Leu Leu Phe Leu Phe Ser Ser Ala Tyr
1               5                   10                  15

Ser Arg Gly Val Phe Arg Arg Asp Ala His Lys Ser Glu Val Ala His
            20                  25                  30

Arg Phe Lys Asp Leu Gly Glu Glu Asn Phe Lys Ala Leu Val Leu Ile
        35                  40                  45

Ala Phe Ala Gln Tyr Leu Gln Gln Cys Pro Phe Glu Asp His Val Lys
    50                  55                  60

Leu Val Asn Glu Val Thr Glu Phe Ala Lys Thr Cys Val Ala Asp Glu
65                  70                  75                  80

Ser Ala Glu Asn Cys Asp Lys Ser Leu His Thr Leu Phe Gly Asp Lys
                85                  90                  95

Leu Cys Thr Val Ala Thr Leu Arg Glu Thr Tyr Gly Glu Met Ala Asp
            100                 105                 110

Cys Cys Ala Lys Gln Glu Pro Glu Arg Asn Glu Cys Phe Leu Gln His
        115                 120                 125

Lys Asp Asp Asn Pro Asn Leu Pro Arg Leu Val Arg Pro Glu Val Asp
    130                 135                 140

Val Met Cys Thr Ala Phe His Asp Asn Glu Glu Thr Phe Leu Lys Lys
145                 150                 155                 160

Tyr Leu Tyr Glu Ile Ala Arg Arg His Pro Tyr Phe Tyr Ala Pro Glu
                165                 170                 175

Leu Leu Phe Phe Ala Lys Arg Tyr Lys Ala Ala Phe Thr Glu Cys Cys
            180                 185                 190

Gln Ala Ala Asp Lys Ala Ala Cys Leu Leu Pro Lys Leu Asp Glu Leu
        195                 200                 205

Arg Asp Glu Gly Lys Ala Ser Ser Ala Lys Gln Arg Leu Lys Cys Ala
    210                 215                 220

Ser Leu Gln Lys Phe Gly Glu Arg Ala Phe Lys Ala Trp Ala Val Ala
225                 230                 235                 240

Arg Leu Ser Gln Arg Phe Pro Lys Ala Glu Phe Ala Glu Val Ser Lys
                245                 250                 255

Leu Val Thr Asp Leu Thr Lys Val His Thr Glu Cys Cys His Gly Asp
            260                 265                 270

Leu Leu Glu Cys Ala Asp Asp Arg Ala Asp Leu Ala Lys Tyr Ile Cys
        275                 280                 285

Glu Asn Gln Asp Ser Ile Ser Ser Lys Leu Lys Glu Cys Cys Glu Lys
    290                 295                 300

Pro Leu Glu Lys Ser His Cys Ile Ala Glu Val Glu Asn Asp Glu
305                 310                 315                 320

Met Pro Ala Asp Leu Pro Ser Leu Ala Ala Asp Phe Val Glu Ser Lys
                325                 330                 335

Asp Val Cys Lys Asn Tyr Ala Glu Ala Lys Asp Val Phe Leu Gly Met
            340                 345                 350

Phe Leu Tyr Glu Tyr Ala Arg Arg His Pro Asp Tyr Ser Val Val Leu
        355                 360                 365

Leu Leu Arg Leu Ala Lys Thr Tyr Glu Thr Thr Leu Glu Lys Cys Cys
    370                 375                 380

Ala Ala Ala Asp Pro His Glu Cys Tyr Ala Lys Val Phe Asp Glu Phe
385                 390                 395                 400

Lys Pro Leu Val Glu Glu Pro Gln Asn Leu Ile Lys Gln Asn Cys Glu
                405                 410                 415

Leu Phe Glu Gln Leu Gly Glu Tyr Lys Phe Gln Asn Ala Leu Leu Val
            420                 425                 430

Arg Tyr Thr Lys Lys Val Pro Gln Val Ser Thr Pro Thr Leu Val Glu
        435                 440                 445

Val Ser Arg Asn Leu Gly Lys Val Gly Ser Lys Cys Cys Lys His Pro
    450                 455                 460

Glu Ala Lys Arg Met Pro Cys Ala Glu Asp Tyr Leu Ser Val Val Leu
465                 470                 475                 480

Asn Gln Leu Cys Val Leu His Glu Lys Thr Pro Val Ser Asp Arg Val
                485                 490                 495

Thr Lys Cys Cys Thr Glu Ser Leu Val Asn Arg Arg Pro Cys Phe Ser
            500                 505                 510

Ala Leu Glu Val Asp Glu Thr Tyr Val Pro Lys Glu Phe Asn Ala Glu
        515                 520                 525

Thr Phe Thr Phe His Ala Asp Ile Cys Thr Leu Ser Glu Lys Glu Arg
    530                 535                 540

Gln Ile Lys Lys Gln Thr Ala Leu Val Glu Leu Val Lys His Lys Pro
545                 550                 555                 560

Lys Ala Thr Lys Glu Gln Leu Lys Ala Val Met Asp Asp Phe Ala Ala
                565                 570                 575

Phe Val Glu Lys Cys Cys Lys Ala Asp Asp Lys Glu Thr Cys Phe Ala
            580                 585                 590

Glu Glu Gly Lys Lys Leu Val Ala Ala Ser Gln Ala Ala Leu Gly Leu
        595                 600                 605

Lys Leu Leu Cys Thr Pro Ser Arg Leu Val Pro Arg Gly Ser Leu Gln
    610                 615                 620

His His His His His Val Asp
625                 630

<210> SEQ ID NO 111
<211> LENGTH: 69
<212> TYPE: DNA
<213> ORGANISM: Artificial Sequence
<220> FEATURE:
<223> OTHER INFORMATION: Synthetic nucleotide

<400> SEQUENCE: 111

```
aagtgggtaa cctttatttc ccttcttttt ctctttagct cggcttattc cagggtgtg      60 tttcgtcga                                                              69
```

<210> SEQ ID NO 112
<211> LENGTH: 21
<212> TYPE: DNA
<213> ORGANISM: Artificial Sequence
<220> FEATURE:
<223> OTHER INFORMATION: Synthetic nucleotide

<400> SEQUENCE: 112

```
caccatcatc accaccatca c                                                21
```

<210> SEQ ID NO 113
<211> LENGTH: 18
<212> TYPE: DNA
<213> ORGANISM: Artificial Sequence
<220> FEATURE:
<223> OTHER INFORMATION: Synthetic nucleotide

<400> SEQUENCE: 113

```
ctggtgccgc gcggcagc                                                    18
```

<210> SEQ ID NO 114
<211> LENGTH: 18
<212> TYPE: DNA
<213> ORGANISM: Artificial Sequence
<220> FEATURE:
<223> OTHER INFORMATION: Synthetic nucleotide

<400> SEQUENCE: 114

```
ctttgtaccc ctagcagg                                                    18
```

<210> SEQ ID NO 115
<211> LENGTH: 1951
<212> TYPE: DNA
<213> ORGANISM: Artificial Sequence
<220> FEATURE:
<223> OTHER INFORMATION: Synthetic nucleotide

<400> SEQUENCE: 115

```
aaataaagct tcccggggga tccaaacgat gaagtgggta acctttattt cccttcttt      60 tctctttagc tcggcttatt ccaggggtgt gtttcgtcga gatgcacaca agcaccatca    120
tcaccaccat cacctggtgc cgcgcggcag cctttgtacc cctagcaggg gaggcagtga    180
ggttgctcat cggtttaaag atttgggaga agaaaatttc aaagccttgg tgttgattgc    240
ctttgctcag tatcttcagc agtgtccatt tgaagatcat gtaaaattag tgaatgaagt    300
aactgaattt gcaaaaacat gtgttgctga tgagtcagct gaaaattgtg acaaatcact    360
tcatacccct tttggagaca aattatgcac agttgcaact cttcgtgaaa cctatggtga    420
aatggctgac tgctgtgcaa aacaagaacc tgagagaaat gaatgcttct gcaacacaa    480 agatgacaac ccaaacctcc cccgattggt gagaccagag gttgatgtga tgtgcactgc    540
ttttcatgac aatgaagaga catttttgaa aaatactta tatgaaattg ccagaagaca    600
tccttacttt tatgccccgg aactcctttt ctttgctaaa aggtataaag ctgcttttac    660
agaatgttgc caagctgctg ataaagctgc tgcctgttg ccaaagctcg atgaacttcg    720
ggatgaaggg aaggcttcgt ctgccaaaca gagactcaag tgtgccagtc tccaaaaatt    780
tggagaaaga gctttcaaag catgggcagt agctcgcctg agccagagat ttcccaaagc    840
```

-continued

```
tgagtttgca gaagtttcca agttagtgac agaccttacc aaagtccaca cggaatgctg      900
ccatggagac ctgcttgaat gtgctgatga cagggcggac cttgccaagt atatctgtga      960
aaatcaagat tcgatctcca gtaaactgaa ggaatgctgt gaaaaacctc tgttggaaaa     1020
atcccactgc attgccgaag tggaaaatga tgagatgcct gctgacttgc cttcattagc     1080
tgctgatttt gttgaaagta aggatgtttg caaaaactat gctgaggcaa aggatgtctt     1140
cctgggcatg ttttttgtatg aatatgcaag aaggcatcct gattactctg tcgtgctgct     1200
gctgagactt gccaagacat atgaaaccac tctagagaag tgctgtgccg ctgcagatcc     1260
tcatgaatgc tatgccaaag tgttcgatga atttaaacct cttgtggaag agcctcagaa     1320
tttaatcaaa caaaattgtg agcttttga gcagcttgga gagtacaaat tccagaatgc     1380
gctattagtt cgttacacca agaaagtacc ccaagtgtca actccaactc ttgtagaggt     1440
ctcaagaaac ctaggaaaag tgggcagcaa atgttgtaaa catcctgaag caaaagaat     1500 gccctgtgca aagactatc tatccgtggt cctgaaccag ttatgtgtgt tgcatgagaa     1560
aacgccagta agtgacagag tcaccaaatg ctgcacagaa tccttggtga acaggcgacc     1620
atgcttttca gctctggaag tcgatgaaac atacgttccc aaagagttta tgctgaaac      1680 attcaccttc catgcagata tatgcacact ttctgagaag gagagacaaa tcaagaaaca     1740
aactgcactt gttgagctcg tgaaacacaa gcccaaggca acaaaagagc aactgaaagc     1800
tgttatggat gatttcgcag cttttgtaga gaagtgctgc aaggctgacg ataaggagac     1860
ctgctttgcc gaggagggta aaaaacttgt tgctgcaagt caagctgcct taggcttata     1920
atgaattcgt cgacctcgag gatatcacaa g                                    1951
```

<210> SEQ ID NO 116
<211> LENGTH: 630
<212> TYPE: PRT
<213> ORGANISM: Artificial Sequence
<220> FEATURE:
<223> OTHER INFORMATION: Synthetic peptide

<400> SEQUENCE: 116

```
Met Lys Trp Val Thr Phe Ile Ser Leu Leu Phe Leu Phe Ser Ser Ala
  1               5                  10                  15

Tyr Ser Arg Gly Val Phe Arg Arg Asp Ala His Lys His His His His
                 20                  25                  30

His His His Leu Val Pro Arg Gly Ser Leu Cys Thr Pro Ser Arg Gly
             35                  40                  45

Gly Ser Glu Val Ala His Arg Phe Lys Asp Leu Gly Glu Glu Asn Phe
     50                  55                  60

Lys Ala Leu Val Leu Ile Ala Phe Ala Gln Tyr Leu Gln Gln Cys Pro
 65                  70                  75                  80

Phe Glu Asp His Val Lys Leu Val Asn Glu Val Thr Glu Phe Ala Lys
                 85                  90                  95

Thr Cys Val Ala Asp Glu Ser Ala Glu Asn Cys Asp Lys Ser Leu His
            100                 105                 110

Thr Leu Phe Gly Asp Lys Leu Cys Thr Val Ala Thr Leu Arg Glu Thr
        115                 120                 125

Tyr Gly Glu Met Ala Asp Cys Cys Ala Lys Gln Glu Pro Glu Arg Asn
    130                 135                 140

Glu Cys Phe Leu Gln His Lys Asp Asp Asn Pro Asn Leu Pro Arg Leu
145                 150                 155                 160

Val Arg Pro Glu Val Asp Val Met Cys Thr Ala Phe His Asp Asn Glu
```

```
                165                 170                 175
Glu Thr Phe Leu Lys Lys Tyr Leu Tyr Glu Ile Ala Arg Arg His Pro
            180                 185                 190
Tyr Phe Tyr Ala Pro Glu Leu Leu Phe Phe Ala Lys Arg Tyr Lys Ala
        195                 200                 205
Ala Phe Thr Glu Cys Cys Gln Ala Ala Asp Lys Ala Ala Cys Leu Leu
    210                 215                 220
Pro Lys Leu Asp Glu Leu Arg Asp Gly Lys Ala Ser Ser Ala Lys
225                 230                 235                 240
Gln Arg Leu Lys Cys Ala Ser Leu Gln Lys Phe Gly Glu Arg Ala Phe
                245                 250                 255
Lys Ala Trp Ala Val Ala Arg Leu Ser Gln Arg Phe Pro Lys Ala Glu
            260                 265                 270
Phe Ala Glu Val Ser Lys Leu Val Thr Asp Leu Thr Lys Val His Thr
        275                 280                 285
Glu Cys Cys His Gly Asp Leu Leu Glu Cys Ala Asp Asp Arg Ala Asp
    290                 295                 300
Leu Ala Lys Tyr Ile Cys Glu Asn Gln Asp Ser Ile Ser Ser Lys Leu
305                 310                 315                 320
Lys Glu Cys Cys Glu Lys Pro Leu Leu Glu Lys Ser His Cys Ile Ala
                325                 330                 335
Glu Val Glu Asn Asp Glu Met Pro Ala Asp Leu Pro Ser Leu Ala Ala
            340                 345                 350
Asp Phe Val Glu Ser Lys Asp Val Cys Lys Asn Tyr Ala Glu Ala Lys
        355                 360                 365
Asp Val Phe Leu Gly Met Phe Leu Tyr Glu Tyr Ala Arg Arg His Pro
    370                 375                 380
Asp Tyr Ser Val Val Leu Leu Leu Arg Leu Ala Lys Thr Tyr Glu Thr
385                 390                 395                 400
Thr Leu Glu Lys Cys Cys Ala Ala Ala Asp Pro His Glu Cys Tyr Ala
                405                 410                 415
Lys Val Phe Asp Glu Phe Lys Pro Leu Val Glu Glu Pro Gln Asn Leu
            420                 425                 430
Ile Lys Gln Asn Cys Glu Leu Phe Glu Gln Leu Gly Glu Tyr Lys Phe
        435                 440                 445
Gln Asn Ala Leu Leu Val Arg Tyr Thr Lys Lys Val Pro Gln Val Ser
    450                 455                 460
Thr Pro Thr Leu Val Glu Val Ser Arg Asn Leu Gly Lys Val Gly Ser
465                 470                 475                 480
Lys Cys Cys Lys His Pro Glu Ala Lys Arg Met Pro Cys Ala Glu Asp
                485                 490                 495
Tyr Leu Ser Val Val Leu Asn Gln Leu Cys Val Leu His Glu Lys Thr
            500                 505                 510
Pro Val Ser Asp Arg Val Thr Lys Cys Cys Thr Glu Ser Leu Val Asn
        515                 520                 525
Arg Arg Pro Cys Phe Ser Ala Leu Glu Val Asp Glu Thr Tyr Val Pro
    530                 535                 540
Lys Glu Phe Asn Ala Glu Thr Phe Thr Phe His Ala Asp Ile Cys Thr
545                 550                 555                 560
Leu Ser Glu Lys Glu Arg Gln Ile Lys Lys Gln Thr Ala Leu Val Glu
                565                 570                 575
Leu Val Lys His Lys Pro Lys Ala Thr Lys Glu Gln Leu Lys Ala Val
            580                 585                 590
```

Met Asp Asp Phe Ala Ala Phe Val Glu Lys Cys Cys Lys Ala Asp Asp
        595                 600                 605

Lys Glu Thr Cys Phe Ala Glu Glu Gly Lys Lys Leu Val Ala Ala Ser
        610                 615                 620

Gln Ala Ala Leu Gly Leu
625                 630

<210> SEQ ID NO 117
<211> LENGTH: 1923
<212> TYPE: DNA
<213> ORGANISM: Artificial Sequence
<220> FEATURE:
<223> OTHER INFORMATION: Synthetic nucleotide

<400> SEQUENCE: 117

| | | | | | |
|---|---|---|---|---|---|
| cgaaggatcc | aaacgatgaa | gtgggtaacc | tttatttccc | ttcttttcct | ctttagctcg | 60 |
| gcttattcca | ggggtgtgtt | tcgtcgagat | gcacacaaga | gtgaggttgc | tcatcggttt | 120 |
| aaagatttgg | gagaagaaaa | tttcaaagcc | ttggtgttga | ttgcctttgc | tcagtatctt | 180 |
| cagcagtgtc | catttgaaga | tcatgtaaaa | ttagtgaatg | aagtaactga | atttgcaaaa | 240 |
| acatgtgttg | ctgatgagtc | agctgaaaat | tgtgacaaat | cacttcatac | ccttttttgga | 300 |
| gacaaattat | gcacagttgc | aactcttcgt | gaaacctatg | gtgaaatggc | tgactgctgt | 360 |
| gcaaaacaag | aacctgagag | aaatgaatgc | ttcttgcaac | acaaagatga | caacccaaac | 420 |
| ctcccccgat | ggtgagacc | agaggttgat | gtgatgtgca | ctgcttttca | tgacaatgaa | 480 |
| gagacatttt | tgaaaaaata | cttatatgaa | attgccagaa | gacatcctta | cttttatgcc | 540 |
| ccggaactcc | ttttctttgc | taaaaggtat | aaagctgctt | ttacagaatg | ttgccaagct | 600 |
| gctgataaag | ctgcctgcct | gttgccaaag | ctcgatgaac | ttcgggatga | agggaaggct | 660 |
| tcgtctgcca | aacagagact | caagtgtgcc | agtctccaaa | aatttggaga | aagagctttc | 720 |
| aaagcatggg | cagtagctcg | cctgagccag | agatttccca | aggctgagtt | tgcagaagtt | 780 |
| tccaagttag | tgactgacct | taccaaagtc | cacacggaat | gctgtcacgg | agacctgctt | 840 |
| gaatgtgctg | atgacagggc | ggaccttgcc | aagtatatct | gtgaaaatca | agattcgatc | 900 |
| tccagtaaac | tgaaggaatg | ctgtgaaaaa | cctctgttgg | aaaaatccca | ctgcattgcc | 960 |
| gaagtggaaa | atgatgagat | gcctgctctc | gagccttcta | ctagtgctga | ttttgttgaa | 1020 |
| agtaaggatg | tttgcaaaaa | ctatgctgag | gcaaaggatg | tcttcctggg | catgtttttg | 1080 |
| tatgaatatg | caagaaggca | tcctgattac | tctgtcgtgc | tgctgctgag | acttgccaag | 1140 |
| acatatgaaa | ccacacttga | aagtgctgtg | ccgccgctg | atcctcatga | atgctatgcc | 1200 |
| aaagtgttcg | atgaatttaa | acctcttgtg | gaagagcctc | agaatttaat | caaacaaaat | 1260 |
| tgtgagcttt | ttgagcagct | tggagagtac | aaattccaga | atgcgctatt | agttcgttac | 1320 |
| accaagaaag | taccccaagt | gtcaactcca | actcttgtag | aggtctcaag | aaacctagga | 1380 |
| aaagtgggca | gcaaatgttg | taaacatcct | gaagcaaaaa | gaatgccctg | tgcagaagac | 1440 |
| tatctatccg | tggtcctgaa | ccagttatgt | gtgttgcatg | agaaaacgcc | agtaagtgac | 1500 |
| agagtcacca | aatgctgcac | agaatccttg | gtgaacaggc | gaccatgctt | ttcagctctg | 1560 |
| gaagtcgatg | aaacatacgt | tcccaaagag | tttaatgctg | aaacattcac | cttccatgca | 1620 |
| gatatatgca | cactttctga | aaggagaga | caaatcaaga | aacaaactgc | acttgttgag | 1680 |
| cttgtgaaac | acaagcccaa | ggcaacaaaa | gagcaactga | aagctgttat | ggatgatttc | 1740 |
| gcagcttttg | tagagaagtg | ctgcaaggct | gacgataagg | agacctgctt | tgccgaggag | 1800 |

```
ggtaaaaaac ttgttgctgc aagtcaagct gccttaggct tacccgggtc tactccgcgg    1860
ctggtgccgc gcggcagcct tcaacatcat caccaccatc acgtcgacta atggaattcc    1920
cta                                                                  1923
```

<210> SEQ ID NO 118
<211> LENGTH: 631
<212> TYPE: PRT
<213> ORGANISM: Artificial Sequence
<220> FEATURE:
<223> OTHER INFORMATION: Synthetic peptide

<400> SEQUENCE: 118

```
Met Lys Trp Val Thr Phe Ile Ser Leu Leu Phe Leu Phe Ser Ser Ala
 1               5                  10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
 50                  55                  60

Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Leu Glu Pro Ser Thr Ser Ala Asp Phe Val Glu Ser
                325                 330                 335
```

-continued

```
Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Pro Gln Asn Leu Ile Lys Gln Asn Cys
            405                 410                 415

Glu Leu Phe Glu Gln Leu Gly Glu Tyr Lys Phe Gln Asn Ala Leu Leu
        420                 425                 430

Val Arg Tyr Thr Lys Lys Val Pro Gln Val Ser Thr Pro Thr Leu Val
    435                 440                 445

Glu Val Ser Arg Asn Leu Gly Lys Val Gly Ser Lys Cys Cys Lys His
450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
            485                 490                 495

Val Thr Lys Cys Cys Thr Glu Ser Leu Val Asn Arg Arg Pro Cys Phe
        500                 505                 510

Ser Ala Leu Glu Val Asp Glu Thr Tyr Val Pro Lys Glu Phe Asn Ala
    515                 520                 525

Glu Thr Phe Thr Phe His Ala Asp Ile Cys Thr Leu Ser Glu Lys Glu
530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
            565                 570                 575

Ala Phe Val Glu Lys Cys Cys Lys Ala Asp Asp Lys Glu Thr Cys Phe
        580                 585                 590

Ala Glu Glu Gly Lys Lys Leu Val Ala Ala Ser Gln Ala Ala Leu Gly
    595                 600                 605

Leu Pro Gly Ser Thr Pro Arg Leu Val Pro Arg Gly Ser Leu Gln His
610                 615                 620

His His His His Val Asp
625                 630

<210> SEQ ID NO 119
<211> LENGTH: 24
<212> TYPE: DNA
<213> ORGANISM: Artificial Sequence
<220> FEATURE:
<223> OTHER INFORMATION: Synthetic primer

<400> SEQUENCE: 119
ctagcctttg taccectagc aggg                                          24

<210> SEQ ID NO 120
<211> LENGTH: 24
<212> TYPE: DNA
<213> ORGANISM: Artificial Sequence
<220> FEATURE:
<223> OTHER INFORMATION: Synthetic primer

<400> SEQUENCE: 120
```

```
ctagccctgc tagggtaca aaga                                         24
```

<210> SEQ ID NO 121
<211> LENGTH: 1398
<212> TYPE: DNA
<213> ORGANISM: Artificial Sequence
<220> FEATURE:
<223> OTHER INFORMATION: Synthetic nucleotide

<400> SEQUENCE: 121

```
ccggaactcc ttttctttgc taaaaggtat aaagctgctt ttacagaatg ttgccaagct    60
gctgataaag ctgcctgcct gttgccaaag ctcgatgaac ttcgggatga agggaaggct   120
tcgtctgcca aacagagact caagtgtgcc agtctccaaa aatttggaga aagagctttc   180
aaagcatggg cagtagctcg cctgagccag agatttccca aggctgagtt tgcagaagtt   240
tccaagttag tgactgacct taccaaagtc cacacggaat gctgtcacgg agacctgctt   300
gaatgtgctg atgacagggc ggaccttgcc aagtatatct gtgaaaatca agattcgatc   360
tccagtaaac tgaaggaatg ctgtgaaaaa cctctgttgg aaaaatccca ctgcattgcc   420
gaagtggaaa atgatgagat gcctgctctc gatctttgta ccctagcag ggctactagt   480
gctgattttg ttgaaagtaa ggatgtttgc aaaaactatg ctgaggcaaa ggatgtcttc   540
ctgggcatgt ttttgtatga atatgcaaga aggcatcctg attactctgt cgtgctgctg   600
ctgagacttg ccaagacata tgaaaccaca cttgagaagt gctgtgccgc cgctgatcct   660
catgaatgct atgccaaagt gttcgatgaa tttaaacctc ttgtggaaga gcctcagaat   720
ttaatcaaac aaaattgtga gcttttttgag cagcttggag agtacaaatt ccagaatgcg   780
ctattagttc gttacaccaa gaaagtaccc caagtgtcaa ctccaactct tgtagaggtc   840
tcaagaaacc taggaaaagt gggcagcaaa tgttgtaaac atcctgaagc aaaaagaatg   900
ccctgtgcag aagactatct atccgtggtc ctgaaccagt tatgtgtgtt gcatgagaaa   960
acgccagtaa gtgacagagt caccaaatgc tgcacagaat ccttggtgaa caggcgacca  1020
tgcttttcag ctctggaagt cgatgaaaca tacgttccca agagtttaa tgctgaaaca  1080
ttcaccttcc atgcagatat atgcacactt tctgagaagg agagacaaat caagaaacaa  1140
actgcacttg ttgagcttgt gaaacacaag cccaaggcaa caaaagagca actgaaagct  1200
gttatggatg atttcgcagc ttttgtagag aagtgctgca aggctgacga taaggagacc  1260
tgctttgccg aggagggtaa aaaacttgtt gctgcaagtc aagctgcctt aggcttaccc  1320
gggtctactc cgcggctggt gccgcgcggc agccttcaac atcatcacca ccatcacgtc  1380
gactaatgga attccta                                               1398
```

<210> SEQ ID NO 122
<211> LENGTH: 636
<212> TYPE: PRT
<213> ORGANISM: Artificial Sequence
<220> FEATURE:
<223> OTHER INFORMATION: Synthetic peptide

<400> SEQUENCE: 122

```
Met Lys Trp Val Thr Phe Ile Ser Leu Leu Phe Leu Phe Ser Ser Ala
  1               5                  10                  15

Tyr Ser Arg Gly Val Phe Arg Arg Asp Ala His Lys Ser Glu Val Ala
             20                  25                  30

His Arg Phe Lys Asp Leu Gly Glu Glu Asn Phe Lys Ala Leu Val Leu
         35                  40                  45
```

```
Ile Ala Phe Ala Gln Tyr Leu Gln Gln Cys Pro Phe Glu Asp His Val
 50                  55                  60

Lys Leu Val Asn Glu Val Thr Glu Phe Ala Lys Thr Cys Val Ala Asp
 65                  70                  75                  80

Glu Ser Ala Glu Asn Cys Asp Lys Ser Leu His Thr Leu Phe Gly Asp
                 85                  90                  95

Lys Leu Cys Thr Val Ala Thr Leu Arg Glu Thr Tyr Gly Glu Met Ala
             100                 105                 110

Asp Cys Cys Ala Lys Gln Glu Pro Glu Arg Asn Glu Cys Phe Leu Gln
         115                 120                 125

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                 165                 170                 175

Glu Leu Leu Phe Phe Ala Lys Arg Tyr Lys Ala Ala Phe Thr Glu Cys
             180                 185                 190

Cys Gln Ala Ala Asp Lys Ala Ala Cys Leu Leu Pro Lys Leu Asp Glu
         195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                 245                 250                 255

Lys Leu Val Thr Asp Leu Thr Lys Val His Thr Glu Cys Cys His Gly
             260                 265                 270

Asp Leu Leu Glu Cys Ala Asp Asp Arg Ala Asp Leu Ala Lys Tyr Ile
         275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Leu Asp Leu Cys Thr Pro Ser Arg Ala Thr Ser Ala
                 325                 330                 335

Asp Phe Val Glu Ser Lys Asp Val Cys Lys Asn Tyr Ala Glu Ala Lys
             340                 345                 350

Asp Val Phe Leu Gly Met Phe Leu Tyr Glu Tyr Ala Arg Arg His Pro
         355                 360                 365

Asp Tyr Ser Val Val Leu Leu Leu Arg Leu Ala Lys Thr Tyr Glu Thr
    370                 375                 380

Thr Leu Glu Lys Cys Cys Ala Ala Ala Asp Pro His Glu Cys Tyr Ala
385                 390                 395                 400

Lys Val Phe Asp Glu Phe Lys Pro Leu Val Glu Glu Pro Gln Asn Leu
                 405                 410                 415

Ile Lys Gln Asn Cys Glu Leu Phe Glu Gln Leu Gly Glu Tyr Lys Phe
             420                 425                 430

Gln Asn Ala Leu Leu Val Arg Tyr Thr Lys Lys Val Pro Gln Val Ser
         435                 440                 445

Thr Pro Thr Leu Val Glu Val Ser Arg Asn Leu Gly Lys Val Gly Ser
    450                 455                 460
```

| | | | | | | | | | | | | |
|---|---|---|---|---|---|---|---|---|---|---|---|---|
|Lys|Cys|Cys|Lys|His|Pro|Glu|Ala|Lys|Arg|Met|Pro|Cys|Ala|Glu|Asp|
|465| | | |470| | | |475| | | |480| | | |

Lys Cys Cys Lys His Pro Glu Ala Lys Arg Met Pro Cys Ala Glu Asp
465                 470                 475                 480

Tyr Leu Ser Val Val Leu Asn Gln Leu Cys Val Leu His Glu Lys Thr
                485                 490                 495

Pro Val Ser Asp Arg Val Thr Lys Cys Cys Thr Glu Ser Leu Val Asn
            500                 505                 510

Arg Arg Pro Cys Phe Ser Ala Leu Glu Val Asp Glu Thr Tyr Val Pro
        515                 520                 525

Lys Glu Phe Asn Ala Glu Thr Phe Thr Phe His Ala Asp Ile Cys Thr
    530                 535                 540

Leu Ser Glu Lys Glu Arg Gln Ile Lys Lys Gln Thr Ala Leu Val Glu
545                 550                 555                 560

Leu Val Lys His Lys Pro Lys Ala Thr Lys Glu Gln Leu Lys Ala Val
                565                 570                 575

Met Asp Asp Phe Ala Ala Phe Val Glu Lys Cys Cys Lys Ala Asp Asp
            580                 585                 590

Lys Glu Thr Cys Phe Ala Glu Glu Gly Lys Lys Leu Val Ala Ala Ser
        595                 600                 605

Gln Ala Ala Leu Gly Leu Pro Gly Ser Thr Pro Arg Leu Val Pro Arg
    610                 615                 620

Gly Ser Leu Gln His His His His His His Val Asp
625                 630                 635

<210> SEQ ID NO 123
<211> LENGTH: 27
<212> TYPE: DNA
<213> ORGANISM: Artificial Sequence
<220> FEATURE:
<223> OTHER INFORMATION: Synthetic primer

<400> SEQUENCE: 123
ccggactttg taccectagc aggggge                                          27

<210> SEQ ID NO 124
<211> LENGTH: 21
<212> TYPE: DNA
<213> ORGANISM: Artificial Sequence
<220> FEATURE:
<223> OTHER INFORMATION: Synthetic primer

<400> SEQUENCE: 124
cccctgctag gggtacaaag t                                                21

<210> SEQ ID NO 125
<211> LENGTH: 1470
<212> TYPE: DNA
<213> ORGANISM: Artificial Sequence
<220> FEATURE:
<223> OTHER INFORMATION: Synthetic nucleotide

<400> SEQUENCE: 125
gagacatttt tgaaaaaata cttatatgaa attgccagaa gacatcctta ctttttatgcc      60 ccggaactcc ttttctttgc taaaaggtat aaagctgctt ttacagaatg ttgccaagct     120
gctgataaag ctgcctgcct gttgccaaag ctcgatgaac ttcgggatga agggaaggct     180
tcgtctgcca aacagagact caagtgtgcc agtctccaaa aatttggaga aagagctttc     240
aaagcatggg cagtagctcg cctgagccag agatttccca aggctgagtt tgcagaagtt     300
tccaagttag tgactgacct taccaaagtc cacacggaat gctgtcacgg agacctgctt     360

-continued

```
gaatgtgctg atgacagggc ggaccttgcc aagtatatct gtgaaaatca agattcgatc    420
tccagtaaac tgaaggaatg ctgtgaaaaa cctctgttgg aaaaatccca ctgcattgcc    480
gaagtggaaa atgatgagat gcctgctctc gatctttgta cccctagcag ggctactagt    540
gctgattttg ttgaaagtaa ggatgtttgc aaaaactatg ctgaggcaaa ggatgtcttc    600
ctgggcatgt ttttgtatga atatgcaaga aggcatcctg attactctgt cgtgctgctg    660
ctgagacttg ccaagacata tgaaaccaca cttgagaagt gctgtgccgc cgctgatcct    720
catgaatgct atgccaaagt gttcgatgaa tttaaacctc ttgtggaaga gcctcagaat    780
ttaatcaaac aaaattgtga gcttttcgag cagcttggag agtacaaatt ccagaatgcg    840
ctattagttc gttacaccaa gaaagtaccc caagtgtcaa ctccaactct tgtagaggtc    900
tcaagaaacc taggaaaagt gggcagcaaa tgttgtaaac atcctgaagc aaaaagaatg    960
ccctgtgcag aagactatct atccgtggtc ctgaaccagt atgtgtgtt gcatgagaaa    1020 acgccagtaa gtgacagagt caccaaatgc tgcacagaat ccttggtgaa caggcgacca    1080
tgcttttcag ctctggaagt cgatgaaaca tacgttccca aagagtttaa tgctgaaaca    1140
ttcaccttcc atgcagatat atgcacactt tctgagaagg agagacaaat caagaaacaa    1200
actgcacttg ttgagcttgt gaaacacaag cccaaggcaa caaaagagca actgaaagct    1260
gttatggatg atttcgcagc ttttgtagag aagtgctgca aggctgacga taaggagacc    1320
tgctttgccg aggagggtaa aaaacttgtt gctgcaagtc aagctgcctt aggcttaccc    1380
ggactttgta cccctagcag ggggcggctg gtgccgcgcg cagccttca acatcatcac    1440 caccatcacg tcgactaatg gaattcccta                                    1470
```

<210> SEQ ID NO 126
<211> LENGTH: 640
<212> TYPE: PRT
<213> ORGANISM: Artificial Sequence
<220> FEATURE:
<223> OTHER INFORMATION: Synthetic peptide

<400> SEQUENCE: 126

```
Met Lys Trp Val Thr Phe Ile Ser Leu Leu Phe Leu Phe Ser Ser Ala
 1               5                  10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125
```

His Lys Asp Asp Asn Pro Asn Leu Pro Arg Leu Val Arg Pro Glu Val
130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
            165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
290                 295                 300

Lys Pro Leu Leu Glu Lys Ser His Cys Ile Ala Glu Val Glu Asn Asp
305                 310                 315                 320

Glu Met Pro Ala Leu Asp Leu Cys Thr Pro Ser Arg Ala Thr Ser Ala
                325                 330                 335

Asp Phe Val Glu Ser Lys Asp Val Cys Lys Asn Tyr Ala Glu Ala Lys
            340                 345                 350

Asp Val Phe Leu Gly Met Phe Leu Tyr Glu Tyr Ala Arg Arg His Pro
        355                 360                 365

Asp Tyr Ser Val Val Leu Leu Leu Arg Leu Ala Lys Thr Tyr Glu Thr
    370                 375                 380

Thr Leu Glu Lys Cys Cys Ala Ala Ala Asp Pro His Glu Cys Tyr Ala
385                 390                 395                 400

Lys Val Phe Asp Glu Phe Lys Pro Leu Val Glu Glu Pro Gln Asn Leu
                405                 410                 415

Ile Lys Gln Asn Cys Glu Leu Phe Glu Gln Leu Gly Glu Tyr Lys Phe
            420                 425                 430

Gln Asn Ala Leu Leu Val Arg Tyr Thr Lys Lys Val Pro Gln Val Ser
        435                 440                 445

Thr Pro Thr Leu Val Glu Val Ser Arg Asn Leu Gly Lys Val Gly Ser
450                 455                 460

Lys Cys Cys Lys His Pro Glu Ala Lys Arg Met Pro Cys Ala Glu Asp
465                 470                 475                 480

Tyr Leu Ser Val Val Leu Asn Gln Leu Cys Val Leu His Glu Lys Thr
                485                 490                 495

Pro Val Ser Asp Arg Val Thr Lys Cys Cys Thr Glu Ser Leu Val Asn
            500                 505                 510

Arg Arg Pro Cys Phe Ser Ala Leu Glu Val Asp Glu Thr Tyr Val Pro
        515                 520                 525

Lys Glu Phe Asn Ala Glu Thr Phe Thr Phe His Ala Asp Ile Cys Thr
    530                 535                 540

Leu Ser Glu Lys Glu Arg Gln Ile Lys Lys Gln Thr Ala Leu Val Glu

```
                545             550             555             560
Leu Val Lys His Lys Pro Lys Ala Thr Lys Glu Gln Leu Lys Ala Val
                565                     570             575

Met Asp Asp Phe Ala Ala Phe Val Glu Lys Cys Cys Lys Ala Asp Asp
                580                     585             590

Lys Glu Thr Cys Phe Ala Glu Glu Gly Lys Lys Leu Val Ala Ala Ser
        595                     600             605

Gln Ala Ala Leu Gly Leu Pro Gly Leu Cys Thr Pro Ser Arg Gly Arg
        610             615             620

Leu Val Pro Arg Gly Ser Leu Gln His His His His His His Val Asp
625                 630             635             640

<210> SEQ ID NO 127
<211> LENGTH: 12
<212> TYPE: PRT
<213> ORGANISM: Artificial Sequence
<220> FEATURE:
<223> OTHER INFORMATION: Synthetic peptide

<400> SEQUENCE: 127

His His His His His His Leu Cys Thr Pro Ser Arg
1               5                   10
```

ALDEHYDE-TAGGED PROTEIN-BASED DRUG CARRIERS AND METHODS OF USE

CROSS-REFERENCE TO RELATED APPLICATIONS

This application is a continuation of U.S. application Ser. No. 12/706,679 filed Feb. 16, 2010, now U.S. Pat. No. 9,238,878, which claims priority benefit of U.S. provisional application Ser. No. 61/153,162, filed Feb. 17, 2009, which applications are incorporated herein by reference in their entirety.

INTRODUCTION

The field of protein and small molecule therapeutics has advanced greatly, providing a number of clinically beneficial drugs and promising to provide more with the years to come. Protein therapeutics can provide several advantages in therapies, due to, for example, exquisite specificity, multiplicity of functions and relatively low off-target activity, resulting in fewer side effects. With the development of sophisticated screening methods, small molecule drugs have also advanced in specificity of action.

Often, though, such therapeutics can be further improved by providing for enhanced activity following administration. For example, it is often desirable to increase the serum half-life of the therapeutic (e.g., in order to reduce the overall dose and/or the number of administrations required over a dosage period). Alternatively or in addition, therapeutics could benefit from improving their bioavailability. For example, some drugs may benefit from improving solubility in the relevant physiological environment and/or to facilitation formulation (e.g., to increase shelf-life). Moreover, conjugation of a drug to a carrier protein can be difficult to control, resulting in a heterogeneous mixture of conjugates that differ in the number of drug molecules attached. This can make controlling the amount administered to a patient difficult.

There is a need for methods and compositions that provide drug conjugates.

SUMMARY

The disclosure provides aldehyde-tagged protein carriers that can be covalently and site-specifically bound to drug to provide a drug-containing scaffold. The disclosure also provides methods of production of such drug-containing scaffolds and intermediates, as well as methods of use.

Accordingly, the present disclosure provides carrier protein-drug conjugates composed of a carrier protein and a covalently bound drug, wherein the carrier protein comprises a modified sulfatase motif of the formula:

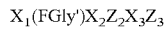

where FGly' is of the formula:

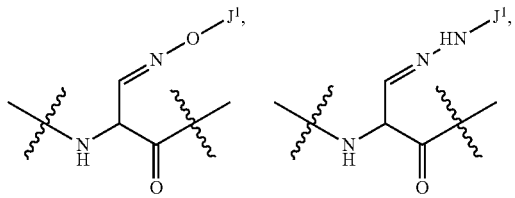

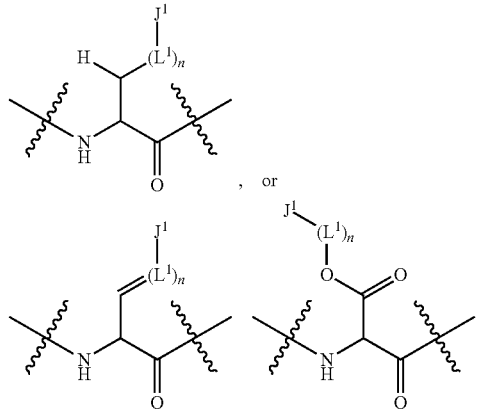

wherein $J^1$ is the covalently bound drug;

each $L^1$ is a divalent moiety independently selected from alkylene, substituted alkylene, alkenylene, substituted alkenylene, alkynylene, alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;

n is a number selected from zero to 40;

$Z_2$ is a proline or alanine residue;

$X_1$ is present or absent and, when present, is any amino acid, with the proviso that when the sulfatase motif is at an N-terminus of the polypeptide, $X_1$ is present;

$X_2$ and $X_3$ are each independently any amino acid; and $Z_3$ is a basic amino acid, and wherein the carrier protein presents the covalently bound drug on a solvent-accessible surface when in a folded state.

In some embodiments, the carrier protein-drug conjugate contains two or more modified sulfatase motifs, and can contain three or more modified sulfatase motifs.

In further embodiments the modified sulfatase motifs of the carrier protein-drug conjugate are positioned in the carrier protein-drug conjugate at at least one of an N-terminus of the carrier protein, a C-terminus of the carrier protein, and a solvent-accessible loop of the carrier protein.

The modified sulfatase motifs of the carrier protein-drug conjugate can be provided as a concatamer composed of modified sulfatase motifs separated by a flexible linker.

In one exemplar, the carrier protein of the carrier protein-drug conjugate is albumin. The covalently bound drug can be a peptide drug, such as glucagon-like peptide 1 (GLP-1) or a biologically active variant thereof, or calcitonin or a biologically active variant thereof. The covalently bound drug of the carrier protein-drug conjugate can be a small molecule drug (e.g., doxorubicin).

Exemplary carrier protein-drug conjugates include those where $Z_3$ is arginine (R). In exemplary embodiments, $X_1$, when present, $X_2$, and $X_3$ are each independently an aliphatic amino acid, a sulfur-containing amino acid, or a polar, uncharged amino acid. In specific examples, $X_1$, when present, is L, M, V, S or T. In specific examples, $X_2$ and $X_3$ are each independently S, T, A, V, G, or C.

The disclosure also provides aldehyde-tagged carrier proteins having an amino acid sequence of:

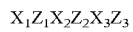

where
$Z_1$ is a cysteine, a serine, or a 2-formylglycine residue;
$Z_2$ is a proline or alanine residue;
$X_1$ is present or absent and, when present, is any amino acid, with the proviso that when the heterologous sulfatase motif is at an N-terminus of the aldehyde tagged polypeptide, $X_1$ is present; and
$X_2$ and $X_3$ are each independently any amino acid; and
$Z_3$ is a basic amino acid;
wherein the carrier protein presents the covalently bound drug on a solvent-accessible surface when in a folded state.

In some examples the aldehyde-tagged carrier protein contains two or more modified sulfatase motifs, and can contain three or more modified sulfatase motifs. In some examples, the modified sulfatase motifs are positioned in the aldehyde-tagged carrier protein at at least one of an N-terminus of the carrier protein, a C-terminus of the carrier protein, and a solvent-accessible loop of the carrier protein. In one example, the carrier protein is albumin Exemplary aldehyde-tagged carrier proteins include those in which $Z_3$ is arginine (R). Exemplary aldehyde-tagged carrier proteins include those in which $X_1$, when present, $X_2$, and $X_3$ are each independently an aliphatic amino acid, a sulfur-containing amino acid, or a polar, uncharged amino acid. In specific examples of aldehyde-tagged carrier protein, $X_1$, when present, is L, M, V, S or T. In specific examples of aldehyde-tagged carrier protein, $X_2$ and $X_3$ are each independently S, T, A, V, G, or C.

The disclosure also provides libraries of modified carrier proteins containing a population of aldehyde-tagged carrier proteins according to the present disclosure, or nucleic acid constructs encoding the aldehyde-tagged carrier proteins, where $Z_1$ is a cysteine or serine residue, wherein the population comprises members having differently aldehyde-tagged carrier proteins. In some examples, the population of the library includes aldehyde-tagged carrier proteins having two or more aldehyde tags. In some examples, the wherein the population of the library includes aldehyde-tagged carrier proteins having at least one aldehyde tag at one or more of the N-terminus, the C-terminus, or an interior loop and the carrier protein. In some embodiments, the library is provided as a population of recombinant cells genetically modified to express the nucleic acid constructs.

The disclosure also provides methods of producing a carrier protein-drug conjugate by combining in a reaction mixture an aldehyde-tagged carrier protein having a 2-formyl-glycine residue (FGly' at $Z_1$) and a drug for conjugation to the carrier protein, wherein the drug has an aminooxy or hydrazide reactive group. The drug is provided in the reaction mixture in an amount sufficient to provide for a desired ratio of drug to carrier protein, said combining being under conditions suitable to promote reaction between an aldehyde of the carrier protein and reactive group of the drug to generate a carrier protein-drug conjugate. The carrier protein-drug conjugate is then isolated from the reaction mixture. In specific embodiments, the aldehyde-tagged carrier protein is folded prior to said combining.

The disclosure also provides formulations containing a carrier protein-drug conjugate of the present disclosure and a pharmaceutically acceptable excipient.

The disclosure also provides methods of treating a subject having or at risk of having condition amenable to treatment with glucagon-like peptide 1 (GLP-1) by administering to a subject in of treatment a carrier protein-drug conjugate of the present disclosure in which the covalently bound drug is glucagon-like peptide 1 (GLP-1) or a biologically active variant thereof, where administration is effective to treat the condition in the subject. The disclosure also provides methods of treating a subject having or at risk of having condition amenable to treatment with calcitonin by administering to a subject in of treatment a carrier protein-drug conjugate of the present disclosure in which the covalently bound drug is calcitonin or a biologically active variant thereof, where administration is effective to treat the condition in the subject.

The disclosure also provides recombinant nucleic acids having nucleic acid encoding an aldehyde-tagged carrier protein of the present disclosure in which $Z_1$ is a cysteine residue or a serine residue.

Other features are provided below, and will be readily apparent to the ordinarily skilled artisan upon reading the present disclosure.

BRIEF DESCRIPTION OF THE DRAWINGS

It is emphasized that, according to common practice, the various features of the drawings may not be to-scale. On the contrary, the dimensions of the various features are arbitrarily expanded or reduced for clarity. Included in the drawings are the following figures:

FIG. 4 is a schematic providing amino acid sequences of exemplary ald-tagged HSA proteins (SEQ ID NO:72-76). The prepro leader sequence is indicated by a single underline. The sulfatase motif is indicated by a double underline.

FIGS. 5-9 are schematics providing the nucleic acid sequences (SEQ ID NO:77-81) of the exemplary ald-tagged HSA proteins of FIG. 4.

FIG. 11 provides amino acid sequences (SEQ ID NO:82-89) of exemplary ald-tagged Fc proteins. The sulfatase motif is indicated by double-underlined text.

DETAILED DESCRIPTION OF EXEMPLARY EMBODIMENTS

Figure 1A:
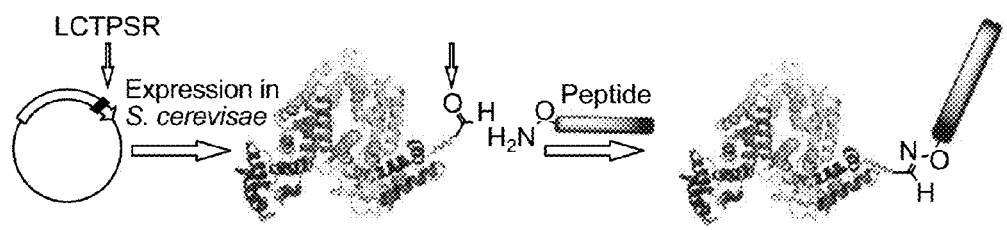
FIG. 1A is a schematic illustrating production of an ald-tagged carrier protein containing a 2-formylglycine (FGly), which is reacted with an aminooxy-containing peptide to form a drug-conjugate of the present disclosure. The aldehyde tag is exemplified in FIG. 1A by LCTPSR (SEQ ID NO:1).

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and exemplary methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "an aldehyde tag" includes a plurality of such tags and reference to "the polypeptide" includes reference to one or more polypeptides and equivalents thereof known to those skilled in the art, and so forth.

It is further noted that the claims may be drafted to exclude any element which may be optional. As such, this statement is intended to serve as antecedent basis for use of such exclusive terminology as "solely", "only" and the like in connection with the recitation of claim elements, or the use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The terms "polypeptide", "peptide" and "protein" are used interchangeably herein to refer to a polymeric form of amino acids of any length. Unless specifically indicated otherwise, "polypeptide", "peptide" and "protein" can include genetically coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, proteins which contain at least one N-terminal methionine residue (e.g., to facilitate production in a recombinant bacterial host cell); immunologically tagged proteins; and the like.

"Native amino acid sequence" or "parent amino acid sequence" are used interchangeably herein in the context of a carrier protein to refer to the amino acid sequence of the carrier protein prior to modification to include a heterologous aldehyde tag.

By "aldehyde tag" or "ald-tag" is meant an amino acid sequence that contains an amino acid sequence derived from a sulfatase motif which is capable of being converted, or which has been converted, by action of a formylglycine generating enzyme (FGE) to contain a 2-formylglycine residue (referred to herein as "FGly"). Although this is technically incorrect, the FGly residue generated by an FGE is often referred to in the literature as a "formylglycine". Stated differently, the term "aldehyde tag" is used herein to refer to an amino acid sequence comprising an "unconverted" sulfatase motif (i.e., a sulfatase motif in which the cysteine or serine residues has not been converted to FGly by an FGE, but is capable of being converted) as well as to an amino acid sequence comprising a "converted" sulfatase motif (i.e., a sulfatase motif in which the cysteine or serine residues has been converted to FGly by action of an FGE).

By "conversion" as used in the context of action of a formylglycine generating enzyme (FGE) on a sulfatase motif refers to biochemical modification of a cysteine or serine residue in a sulfatase motif to a formylglycine (FGly) residue (e.g., Cys to FGly, or Ser to FGly).

"Modification" encompasses addition, removal, or alteration of a moiety. As used in the context of a polypeptide having a converted sulfatase motif, "modification" is meant to refer to chemical or biochemical modification of an FGly residue of an aldehyde tag of a polypeptide through reaction of the FGly aldehyde moiety with a reactive partner. As discussed above, the term "conversion" refers to a type of biochemical modification of an FGly residue of an aldehyde tag mediated by an FGE. An aldehyde tag that is modified by reaction of an FGly with a reactive partner as described herein is sometimes referred to as a "modified ald tag" or an aldehyde tag containing "FGly'".

By "genetically-encodable" as used in reference to an amino acid sequence of polypeptide, peptide or protein means that the amino acid sequence is composed of amino acid residues that are capable of production by transcription and translation of a nucleic acid encoding the amino acid sequence, where transcription and/or translation may occur in a cell or in a cell-free in vitro transcription/translation system.

The term "control sequences" refers to DNA sequences to facilitate expression of an operably linked coding sequence in a particular expression system, e.g. mammalian cell, bacterial cell, cell-free synthesis, etc. The control sequences that are suitable for prokaryote systems, for example, include a promoter, optionally an operator sequence, and a ribosome binding site. Eukaryotic cell systems may utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate the initiation of translation. Generally, "operably linked" means that the DNA sequences being linked are contiguous, and, in the case of a secretory leader, contiguous and in reading frame. Linking is accomplished by ligation or through amplification reactions. Synthetic oligonucleotide adaptors or linkers may be used for linking sequences in accordance with conventional practice.

The term "expression cassette" as used herein refers to a segment of nucleic acid, usually DNA, that can be inserted into a nucleic acid (e.g., by use of restriction sites compatible with ligation into a construct of interest or by homologous recombination into a construct of interest or into a host cell genome). In general, the nucleic acid segment comprises a polynucleotide that encodes a polypeptide of interest (e.g., an aldehyde tagged-carrier protein), and the cassette and restriction sites are designed to facilitate insertion of the cassette in the proper reading frame for transcription and translation. Expression cassettes can also comprise elements that facilitate expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially purified" refers to a compound that is removed from its natural environment and is at least 60% free, usually 75% free, and most usually 90% free from other components with which it is naturally associated.

The term "physiological conditions" is meant to encompass those conditions compatible with living cells, e.g., predominantly aqueous conditions of a temperature, pH, salinity, etc. that are compatible with living cells.

By "heterologous" is meant that a first entity and second entity are provided in an association that is not normally found in nature. For example, a protein containing a "heterologous" sulfatase motif or "heterologous" ald-tag is a protein that does not normally contain a sulfatase motif at that position within its amino acid sequence (e.g., proteins which have a single, native sulfatase motif can contain a second sulfatase motif that is "heterologous"; further proteins which contain a sulfatase motif can be modified so as to reposition the sulfatase motif, rendering the re-positioned sulfatase motif "heterologous" to the protein). In some embodiments, a heterologous sulfatase motif is present in a polypeptide which contains no native sulfatase motif.

By "reactive partner" is meant a molecule or molecular moiety that specifically reacts with another reactive partner to produce a reaction product. Exemplary reactive partners include an cysteine or serine of sulfatase motif and a formylglycine generating enzyme (FGE), which react to form a reaction product of a converted aldehyde tag containing a FGly in lieu of cysteine or serine in the motif. Other exemplary reactive partners include an aldehyde of a formylglycine (FGly) residue of a converted aldehyde tag and a reactive partner reagent comprising a moiety of interest, which react to form a reaction product of a modified aldehyde tagged polypeptide having the moiety of interest conjugated to the aldehyde tagged polypeptide at the FGly residue.

"N-terminus" refers to the terminal amino acid residue of a polypeptide having a free amine group, which amine group in non-N-terminus amino acid residues normally forms part of the covalent backbone of the polypeptide.

"C-terminus" refers to the terminal amino acid residue of a polypeptide having a free carboxyl group, which carboxyl group in non-C-terminus amino acid residues normally forms part of the covalent backbone of the polypeptide.

By "N-terminal" is meant the region of a polypeptide that is closer to the N-terminus than to the C-terminus.

By "C-terminal" is meant the region of a polypeptide that is closer to the C-terminus than to the N-terminus.

By "internal site" as used in referenced to a polypeptide or an amino acid sequence of a polypeptide means a region of the polypeptide that is not at the N-terminus or at the C-terminus, and includes both N-terminal and C-terminal regions of the polypeptide.

Introduction

The present disclosure provides aldehyde-tagged protein carriers that can be covalently and site-specifically bound to drug to provide a drug-containing scaffold, as well as methods of production of such drug-containing scaffolds and intermediates, as well as methods of use. Aldehyde-tagged carrier proteins may also be referred to herein as "ald-tagged carrier proteins", "ald-tagged protein scaffolds" or "ald-tagged scaffolds". Such Ald-tagged scaffolds can be site-specifically decorated with a covalently bound molecule of interest, such as a drug (e.g., a peptide, a small molecule drug, and the like). Such drug-scaffold conjugates can provide for enhanced serum half-life of the drug.

The compositions and methods of the present disclosure exploit a naturally-occurring, genetically-encodable sulfatase motif for use as a tag, referred to herein as an "aldehyde tag" or "ald tag", to direct site-specific modification of the carrier protein. The sulfatase motif of the aldehyde tag, which is based on a motif found in active sites of sulfatases, contains a serine or cysteine residue that is capable of being converted (oxidized) to a 2-formylglycine (FGly) residue by action of a formylglycine generating enzyme (FGE) either in vivo (e.g., at the time of translation of an ald tag-containing protein in a cell) or in vitro (e.g., by contacting an ald tag-containing protein with an FGE in a cell-free system). The aldehyde moiety of the resulting FGly residue can be used as a "chemical handle" to facilitate site-specific chemical modification of the protein, and thus site-specific attachment of a drug of interest. For example, a peptide modified to contain an α-nucleophile-containing moiety (e.g., an aminooxy or hydrazide moiety) can be reacted with the FGly-containing carrier protein to yield a conjugate in which the carrier protein and peptide are linked by a hydrazone or oxime bond, respectively. The reactivity of the aldehyde thus allows for bioorthongonal and chemoselective modification of the carrier protein, and thus provides a site-specific means for chemical modification that in turn can be exploited to provide for site-specific attachment of a moiety of interest in the final conjugate.

Figure 1B:
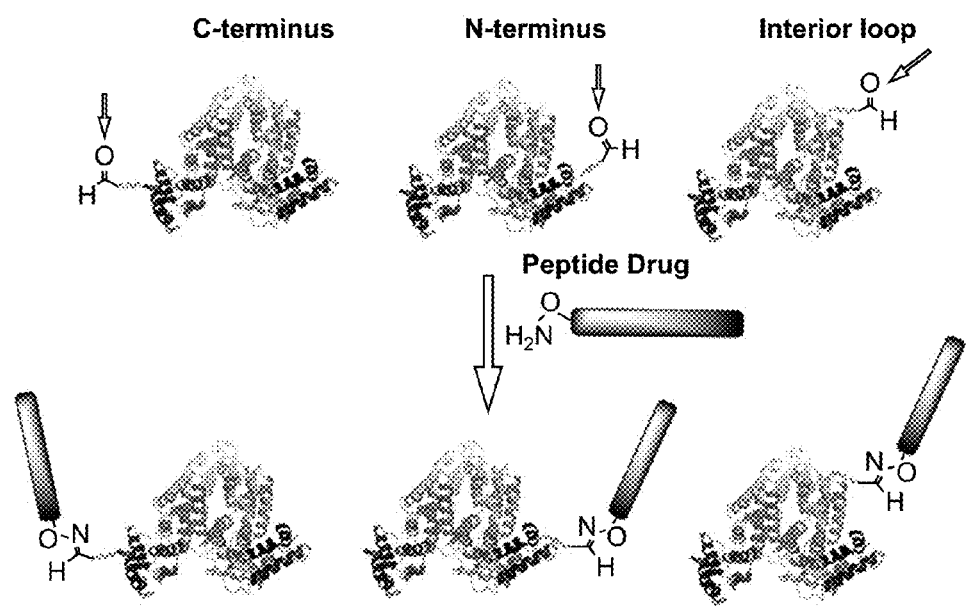
FIG. 1B is a schematic illustrating a library of ald-tagged carrier proteins, exemplified by an ald-tagged human serum albumin (HSA) (top panel), and ald-tagged HSA-drug conjugates (bottom panel) conjugated to a drug. By changing the location of the aldehyde tag, the spatial display of the peptide relative to the surface of the rHSA can be altered.

For illustrative purposes, a schematic of production of an ald-tagged carrier protein is provided in FIG. 1A. In this example, a construct encoding a carrier protein having an ald tag (exemplified by LCTPSR (SEQ ID NO:1)) is expressed in a host cell (exemplified by the yeast S. cerevisae) which is genetically modified to contain an FGE of M. tuberculosis. Expressing the recombinant protein in yeast not modified with FGE is produced without the cysteine being converted to FGly. The carrier protein can be purified and added to recombinant, purified FGE generating the aldehyde tag on the carrier protein. The resulting carrier protein contains an FGly having an aldehyde moiety (arrow). The ald-tagged carrier protein is then reacted with a peptide having a reactive aminoooxy moiety. The reaction product is a drug-carrier protein conjugate having the peptide bound to the carrier protein through an oxime bond. FIG. 1B illustrates how the ald-tag can be placed at various positions on the carrier protein, thus providing for drug-carrier protein conjugates having bound drug (exemplified by a peptide drug) at different positions on the carrier protein.

Exemplary methods and compositions for practice of the invention will now be described in more detail.

Aldehyde Tags

In general, an aldehyde tag ("ald tag") can be based on any amino acid sequence derived from a sulfatase motif (also referred to as a "sulfatase domain"), which is capable of being converted by action of a formylglycine generating enzyme (FGE) to contain a formylglycine (FGly). Action of FGE is directed in a sequence-specific manner in that the FGE acts at a sulfatase motif, but this sulfatase motif can be positioned within any region of carrier protein. Thus, FGE-mediated conversion of a sulfatase motif is site-specific (i.e., in that FGE acts at the amino acid sequence of a sulfatase motif) but the ability of FGE to act upon the sulfatase motif is sequence context-independent (i.e., the ability of the FGE to convert a cysteine/serine of a sulfatase motif is independent of the sequence context in which the sulfatase motif is presented in the carrier protein).

Exemplary Aldehyde Tags

A minimal sulfatase motif of an aldehyde tag is usually about 5 or 6 amino acid residues in length, usually no more than 6 amino acid residues in length. In general, it is normally desirable to minimize the extent of modification of the native amino acid sequence of the carrier protein, so as to minimize the number of amino acid residues that are inserted, deleted, substituted (replaced), or added (e.g., to the N- or C-terminus). Minimizing the extent of amino acid sequence modification of the carrier protein is usually desirable so as to minimize the impact such modifications may have upon carrier protein structure and/or immunogenicity. Thus, aldehyde tags of particular interest include those that require modification (insertion, addition, deletion, substitution/replacement) of less than 16, 15, 14, 13, 12, 11, 10, 9, 8, or 7 amino acid residues of the amino acid sequence of the carrier protein (e.g., the carrier polypeptide).

It should be noted that while aldehyde tags of particular interest are those based on a minimal sulfatase motif, it will be readily appreciated that longer aldehyde tags are both contemplated and encompassed by the present disclosure and can find use in the compositions and methods of the invention. Aldehyde tags can thus comprise a minimal sulfatase motif of 5 or 6 residues, or can be longer and comprise a minimal sulfatase motif which can be flanked at the N- and/or C-terminal sides of the motif by additional amino acid residues. Aldehyde tags of, for example, 5 or 6 amino acid residues are contemplated, as well as longer amino acid sequences of more than 5, 6, 7, 8, 9, 10, 11, 12, 13, 14, 15, 16, 17, 18, 19, 20 or more amino acid residues.

In general, sulfatase motifs useful in aldehyde tags as described herein are of the formula:

$$X_1Z_1X_2Z_2X_3Z_3 \quad (I)$$

or, in an exemplary embodiment

$$X_1Z_1X_2Z_2X_3R \quad (Ia)$$

where $Z_1$ is cysteine or serine (which can also be represented by (C/S));

$Z_2$ is either a proline or alanine residue (which can also be represented by (P/A));

$Z_3$ is a basic amino acid, and may be arginine (R), lysine (K) or histidine (H), usually lysine), or an aliphatic amino acid (alanine (A), glycine (G), leucine (L), valine (V), isoleucine (I), or proline (P), usually A, G, L, V, or I (in Formula (Ia) $Z_3$ is arginine (R));

$X_1$ is present or absent and, when present, can be any amino acid, though usually an aliphatic amino acid, a sulfur-containing amino acid, or a polar, uncharged amino acid, (i.e., other than a aromatic amino acid or a charged amino acid), usually L, M, V, S or T, more usually L, M, S or V, with the proviso that when the sulfatase motif is at the N-terminus of the carrier protein, $X_1$ is present; and $X_2$ and $X_3$ independently can be any amino acid, though usually an aliphatic amino acid, a polar, uncharged amino acid, or a sulfur containing amino acid (i.e., other than a aromatic amino acid or a charged amino acid), usually S, T, A, V, G or C, more usually S, T, A, V or G.

It should be noted that, following action of an FGE on the sulfatase motif, $Z_1$ is oxidized to generate a 2-formylglycine (FGly) residue. Furthermore, following both FGE-mediated conversion and reaction with a reactive partner of a drug of interest, FGly position at $Z_1$ in the formula above is covalently bound to the drug (e.g., a peptide drug, etc). The reactive partner generally is an α-nucleophile, such as an aminooxy or hydrazide group, and provides for linkage of the carrier protein to the drug through an oxime or hydrazone linkage. Thus the carrier protein and drug are not linked through an amide bond, as may be found in other drug conjugates based on recombinant fusion protein technology.

Where the aldehyde tag is present at a location other than the N-terminus of the carrier protein, $X_1$ of the formula above can be provided by an amino acid residue of the native amino acid sequence of the carrier protein. Therefore, in some embodiments, and when present at a location other than the N-terminus of a carrier protein, sulfatase motifs are of the formula:

$$(C/S)X_1(P/A)X_2Z_3 \quad (II)$$

or, in an exemplary embodiment $$(C/S)X_1(P/A)X_2R \quad (IIa)$$

where $X_1$ and $X_2$ independently can be any amino acid, though usually an aliphatic amino acid, a polar, uncharged amino acid, or a sulfur-containing amino acid (i.e., other than an aromatic amino acid or a charged amino acid), usually S, T, A, V, or C, more usually S, T, A, or V. $Z_3$ in Formula II is defined as above.

As noted above, the sulfatase motif can contain additional residues at one or both of the N- and C-terminus of the sequence, e.g., such that the aldehyde tag includes both a sulfatase motif and an "auxiliary motif". In one embodiment, the sulfatase motif includes an auxiliary motif at the C-terminus (i.e., following the arginine residue in the formula above) 1, 2, 3, 4, 5, 6, or all 7 of the contiguous residues of an amino acid sequence of AALLTGR (SEQ ID NO:46), SQLLTGR (SEQ ID NO:47), AAFMTGR (SEQ ID NO:48), AAFLTGR (SEQ ID NO:49), SAFLTGR (SEQ ID NO:50), ASILTGK (SEQ ID NO:51), VSFLTGR (SEQ ID NO:52), ASLLTGL (SEQ ID NO:53), ASILITG (SEQ ID NO:54), VSFLTGR (SEQ ID NO:55), SAIMTGR (SEQ ID NO:56), SAIVTGR (SEQ ID NO:57), TNLWRG (SEQ ID NO:58), TNLWRGQ (SEQ ID NO:59), TNLCAAS (SEQ ID NO:60), VSLWTGK (SEQ ID NO:61), SMLLTG (SEQ ID NO:62), SMLLTGN (SEQ ID NO:63), SMLLTGT (SEQ ID NO:64), ASFMAGQ (SEQ ID NO:65), or ASLLTGL (SEQ ID NO:66), (see, e.g., Dierks et al. (1999) EMBO J 18(8): 2084-2091), or of GSLFTGR (SEQ ID NO:67). Additional C-terminal amino acid residues are not required for FGE-mediated conversion of the sulfatase motif of the aldehyde tag, and thus are only optional and may be specifically excluded from the aldehyde tags described herein. In some embodiments the aldehyde tag does not contain an amino acid sequence CGPSR(M/A)S (SEQ ID NO:68) or CGPSR(M/A) (SEQ ID NO:69), which may be present as a native amino acid sequence in phosphonate monoester hydrolases.

The sulfatase motif of the aldehyde tag is generally selected so as to be capable of conversion by a selected FGE, e.g., an FGE present in a host cell in which the aldehyde tagged polypeptide is expressed or an FGE which is to be contacted with the aldehyde tagged polypeptide in a cell-free in vitro method.

Selection of aldehyde tags and an FGE that provide for suitable reactive partners to provide for generation of an FGly in the aldehyde tagged carrier protein can be readily accomplished in light of information available in the art. In general, sulfatase motifs susceptible to conversion by a eukaryotic FGE contain a cysteine and a proline (i.e., a cysteine and proline at $Z_1$ and $Z_2$, respectively, in Formula I above (e.g., $X_1CX_2PX_3R$); $CX_1PX_2R$ in Formula II above) and are modified by the "SUMF1-type" FGE (Cosma et al. Cell 2003, 113, (4), 445-56; Dierks et al. Cell 2003, 113, (4), 435-44). Sulfatase motifs susceptible to conversion by a prokaryotic FGE contain either a cysteine or a serine, and a proline in the sulfatase motif (i.e., a cysteine or serine at $Z_1$, and a proline at $Z_2$, respectively, in Formula I above (e.g., $X_1(C/S)X_2PX_3R$); $(C/S)X_1PX_2R$ in Formula II above) are modified either by the "SUMF1-type" FGE or the "AtsB-type" FGE, respectively (Szameit et al. J Biol Chem 1999, 274, (22), 15375-81). Other sulfatase motifs susceptible to conversion by a prokaryotic FGE contain either a cysteine or a serine, and either a proline or an alanine in the sulfatase motif (i.e., a cysteine or serine at $Z_1$, and a proline or alanine at $Z_2$, respectively, e.g., $SX_1AX_2R$; $X_1CX_2PX_3Z_3$; $X_1SX_2PX_2Z_3$; $X_1CX_2AX_3Z_3$; $X_1SX_2AX_3Z_3$; $CX_1PX_2Z_3$; $SX_1PX_2Z_3$; $CX_1AX_2Z_3$; $SX_1AX_2Z_3$ (in Formula I above); $CX_1PX_2Z_3$ (in Formula II above); $X_1CX_2PX_3R$; $X_1SX_2PX_2R$; $X_1CX_2AX_3R$; $X_1SX_2AX_3R$ (in Formula Ia above); $CX_1PX_2R$; $SX_1PX_2R$; $CX_1AX_2R$; $SX_1AX_2R$ (in Formula IIa above), and are susceptible to modification by, for example, can be modified by an FGE of a Firmicutes (e.g., *Clostridium perfringens*) (see Berteau et al. *J. Biol. Chem.* 2006; 281:22464-22470).

Therefore, for example, where the FGE is a eukaryotic FGE (e.g., a mammalian FGE, including a human FGE), the sulfatase motif is usually of the formula:

$$X_1CX_2PX_3Z_3 \quad (III)$$

or, in an exemplary embodiment $$X_1CX_2PX_3R \quad (IIIa)$$

where $X_1$ may be present or absent and, when present, can be any amino acid, though usually an aliphatic amino acid, a sulfur-containing amino acid, or a polar, uncharged amino acid, (i.e., other than an aromatic amino acid or a charged amino acid), usually L, M, S or V, with the proviso that when the sulfatase motif is at the N-terminus of the carrier protein, $X_1$ is present;

$X_2$ and $X_3$ independently can be any amino acid, though usually an aliphatic amino acid, a sulfur-containing amino acid, or a polar, uncharged amino acid, (i.e., other than a aromatic amino acid or a charged amino acid), usually S, T, A, V, G, or C, more usually S, T, A, V or G; and $Z_3$ is a basic amino acid (which may be other than arginine (R), and may be lysine (K) or histidine (H), usually lysine), or an aliphatic amino acid (alanine (A), glycine (G), leucine (L), valine (V), isoleucine (I), or proline (P), usually A, G, L, V, or I, where $Z_3$ is arginine (R) in Formula IIIa.

Specific examples of sulfatase motifs include LCTPSR (SEQ ID NO:1), MCTPSR (SEQ ID NO:2), VCTPSR(SEQ ID NO:3), LCSPSR (SEQ ID NO:4), LCAPSR (SEQ ID NO:5) LCVPSR (SEQ ID NO:6), LCGPSR(SEQ ID NO:7), ICTPAR(SEQ ID NO:8), LCTPSK (SEQ ID NO:9), MCTPSK (SEQ ID NO:10), VCTPSK (SEQ ID NO:11), LCSPSK (SEQ ID NO:12), LCAPSK (SEQ ID NO:13), LCVPSK(SEQ ID NO:14), LCGPSK(SEQ ID NO:15), LCTPSA (SEQ ID NO:16), ICTPAA (SEQ ID NO:17), MCTPSA (SEQ ID NO:18), VCTPSA (SEQ ID NO:19), LCSPSA (SEQ ID NO:20), LCAPSA (SEQ ID NO:21), LCVPSA (SEQ ID NO:22), and LCGPSA (SEQ ID NO:23). Other specific sulfatase motifs are readily apparent from the disclosure provided herein.

As described in more detail below, a converted aldehyde tagged polypeptide is reacted with a reactive partner of a moiety of interest to provide for conjugation between the moiety of interest to the FGly residue of the converted aldehyde tagged polypeptide, and production of a modified polypeptide (e.g., a conjugate of the ald-tagged carrier protein and a peptide drug). Modified polypeptides having a modified aldehyde tag are generally described by comprising a modified sulfatase motif of the formula:

$$X_1(FGly')X_2Z_2X_3Z_3 \quad (I')$$

or, in an exemplary embodiment $$X_1(FGly')X_2Z_2X_3R \quad (Ia')$$

where

FGly' is a formylglycine residue having a covalently attached moiety (e.g., a peptide drug);

$Z_2$ is either a proline or alanine residue (which can also be represented by (P/A));

$Z_3$ in Formula I' is a basic amino acid, and may be arginine (R) (as in Formula Ia'), lysine (K) or histidine (H), usually lysine), or an aliphatic amino acid (alanine (A), glycine (G), leucine (L), valine (V), isoleucine (I), or proline (P), usually A, G, L, V, or I;

$X_1$ may be present or absent and, when present, can be any amino acid, though usually an aliphatic amino acid, a sulfur-containing amino acid, or a polar, uncharged amino acid, (i.e., other than a aromatic amino acid or a charged amino acid), usually L, M, V, S or T, more usually L, M or V, with the proviso that when the sulfatase motif is at the N-terminus of the carrier protein, $X_1$ is present; and $X_2$ and $X_3$ independently can be any amino acid, though usually an aliphatic amino acid, a sulfur-containing amino acid, or a polar, uncharged amino acid, (i.e., other than a aromatic amino acid or a charged amino acid), usually S, T, A, V, G or C, more usually S, T, A, V or G.

Specific examples of converted sulfatase motifs include L(FGly)TPSR (SEQ ID NO:24), M(FGly)TPSR (SEQ ID NO:25), V(FGly)TPSR (SEQ ID NO:26), L(FGly)SPSR (SEQ ID NO:27), L(FGly)APSR (SEQ ID NO:28), L(FGly) VPSR (SEQ ID NO:29), L(FGly)GPSR (SEQ ID NO:30), I(FGly)TPAR (SEQ ID NO:31), L(FGly)TPSK (SEQ ID NO:32), M(FGly)TPSK (SEQ ID NO:33), V(FGly)TPSK (SEQ ID NO:34), L(FGly)SPSK (SEQ ID NO:35), L(FGly) APSK (SEQ ID NO:36), L(FGly)VPSK (SEQ ID NO:37), L(FGly)GPSK (SEQ ID NO:38), L(FGly)TPSA (SEQ ID NO:39), M(FGly)TPSA (SEQ ID NO:40), V(FGly)TPSA (SEQ ID NO:41), L(FGly)SPSA (SEQ ID NO:42), L(FGly) APSA (SEQ ID NO:43), L(FGly)VPSA (SEQ ID NO:44), and L(FGly)GPSA (SEQ ID NO:45). It will be appreciated that exemplary carrier proteins that are covalently bound to drug through reaction with the aldehyde of the FGly residue include those having the amino acid sequences described above, but the modified FGly (represented above by FGly') in lieu of the unmodified FGly.

Carrier Proteins

In general a "carrier protein" is a protein that is biologically inert, is susceptible to modification by use of the ald tag technology as disclosed herein, and which can provide for solvent-accessible presentation of drug conjugated to the carrier protein through a modified ald-tag positioned in the carrier protein (e.g., through an oxime or hydrazone bond within the converted sulfatase motif of the ald tagged carrier protein) in a physiological environment. "Biologically inert" is meant to indicate the carrier protein exhibits clinically insignificant or no detectable biological activity when administered to the appropriate subject, particularly when administered to a human subject. Thus, carrier proteins are biologically inert in that they, for example, are of low immunogenicity, do not exhibit significant or detectable targeting properties (e.g., do not exhibit significant or detectable activity in binding to a specific receptor), and exhibit little or no detectable biological activity that may interfere with activity of a drug to be conjugated to the ald-tagged carrier protein. By "low immunogenicity" is meant that the carrier protein elicits little or no detectable immune response upon administration to a subject, especially a mammalian subject, more especially a human subject. Carrier proteins can be provided in monomeric or multimeric (e.g., dimeric) forms.

Carrier proteins having a three-dimensional structure when folded that provides for multiple different solvent-accessible sites that are amenable to ald-tag modification (and thus conjugation to a drug) are of particular interest. In general, carrier proteins of interest are those that are of a size and three-dimensional folded structure so as to provide for presentation of conjugated drug on solvent accessible surfaces in a manner that is sufficient spatially separated so as to provide for activity and bioavailability of the conjugated drug molecules are of particular interest. The carrier protein will be selected according to a variety of factors including, but not limited to, the drug to be conjugated to the carrier.

Accordingly, any of a wide variety of polypeptides can be suitable for use as ald-tagged carrier proteins for use in the drug-carrier proteins conjugates of the present disclosure. Such carrier proteins can include those having a naturally-occurring amino acid sequence, a native amino acid sequence having an N-terminal methionine, fragments of naturally-occurring polypeptides, and non-naturally occurring polypeptides and fragments thereof.

Exemplary carrier proteins include, but are not necessarily limited to, albumin and fragments thereof (e.g., human serum albumin, bovine serum albumin, and the like), transferrin and fragments thereof (e.g. human transferrin), and Fc fragments having reduced binding to a mammalian Fc receptor, particularly a human Fc receptor (e.g., a modified Fc fragment of an antibody (e.g., IgG), particularly a mammalian antibody, e.g., a human antibody). Exemplary modified Fc fragments having reduced Fc receptor binding are exemplified by the Fc fragments of Herceptin (trastuzumab) and Rituxan (Rituximab), which contain point mutations that provide for reduced Fc receptor binding (see, e.g., Clynes et al Nature Medicine 2000, 6, 443-446). Alternatively or in addition, the isotype of the Fc fragment can be selected according to a desired level of Fc receptor binding (e.g., use of an Fc fragment of an IgG4 isotype human heavy chain constant region rather than from IgG1 or IgG3. (see, e.g, Fridman FASEB J 1991 September; 5 (12): 2684-90) In general, carrier proteins can be at least about 4 kDa (e.g., about 50 amino acid residues in length), usually at least about 25 kDa, and can be larger in size (e.g., transferrin has a molecular weight of 90 kDa while Fc fragments can have molecular weights of 30 kDa to 50 kDa).

Modification of Carrier Proteins to Contain an Aldehyde Tag

An aldehyde tag can be provided in a carrier protein by insertion (e.g., so as to provide a 5 or 6 amino acid residue insertion within the native amino acid sequence) and/or by addition (e.g., at an N- or C-terminus of the carrier protein). An aldehyde tag can also be provided by complete or partial substitution of native amino acid residues of the carrier protein with the contiguous amino acid sequence of an aldehyde tag. For example, a heterologous aldehyde tag of 5 (or 6) amino acid residues can be provided in a carrier protein by replacing 1, 2, 3, 4, or 5 (or 1, 2, 3, 4, 5, or 6) amino acid residues of the native amino acid sequence with the corresponding amino acid residues of the aldehyde tag.

Modification of a carrier protein to include one or more aldehyde tags can be accomplished using recombinant molecular genetic techniques, so as produce nucleic acid encoding the desired aldehyde tagged carrier protein. Such methods are well known in the art, and include cloning methods, site-specific mutation methods, and the like (see, e.g., Sambrook et al., In "Molecular Cloning: A Laboratory Manual" (Cold Spring Harbor Laboratory Press 1989); "Current Protocols in Molecular Biology" (eds., Ausubel et al.; Greene Publishing Associates, Inc., and John Wiley & Sons, Inc. 1990 and supplements). Alternatively, an aldehyde tag can be added using non-recombinant techniques, e.g., using native chemical ligation or pseudo-native chemical ligation, e.g., to add an aldehyde tag to a C-terminus of the carrier protein (see, e.g., U.S. Pat. Nos. 6,184,344; 6,307,018; 6,451,543; 6,570,040; US 2006/0173159; US 2006/0149039). See also Rush et al. (Jan. 5, 2006) Org Lett. 8(1):131-4.

Aldehyde tags can be positioned at any suitable location within a carrier protein, with the proviso that the site of the aldehyde tag is accessible for conversion by an FGE and subsequent modification at the FGly, or can be rendered accessible (e.g., by denaturing the protein). The carrier protein can include one or more aldehyde tags. The number of aldehyde tags that can be present in a carrier protein will vary with the carrier protein selected, and may include 1, 2, 3, 4, 5, or more aldehyde tags.

Carrier Proteins Containing Multiple Ald Tags

Multiple ald tags can be positioned in the ald-tagged carrier protein so as to distribute the tags over the surface of the folded carrier protein. Where the carrier protein is modified to contain multiple ald tags, the ald tags can be spaced apart in the carrier protein by amino acid residues native to the carrier protein. Alternatively or in addition, the carrier protein can include ald tags spaced apart by a linker, where the linker has an amino acid sequence heterologous to the carrier protein.

Alternatively or in addition, the ald tags can be provided in the ald-tagged carrier protein as a concatameric construct of 2, 3, 4 more ald tags, where the expression construct thus encodes for 2, 3, 4 or more sulfatase motifs in a contiguous sequence of the modified carrier protein, wherein the sulfatase motifs are separated by a linker] The linkers of the concatemeric constructs may be designed so as to facilitate presentation of drug conjugated to the ald tag in the final carrier protein-drug conjugate. For example, the linker can be selected so as to provide flexibility between the ald tags, thus allowing for rotation of covalently-bound drug molecules so as to enhance presentation of biologically active drug on the carrier protein-drug conjugate surface. Such linkers can also be used in where the ald tags are not provided as a concatamer, e.g., where an ald tag is positioned at a C- or N-terminus of a carrier protein. Ald tags, including those provided as concatamers, can be positioned at or near the C-terminus of the carrier protein, at or near the N-terminus of the carrier protein, and/or in one or more solvent-accessible loops of the carrier protein.

Linkers will be selected according to a variety of factors (e.g., the ald tag used, the number of ald tags in the concatamer, the degree of flexibility desired), and will be variable length, such as from about 3 amino acids to about 25 amino acids, including about 4 amino acids to about 23 amino acids, about 5 amino acids to about 20 amino acids, about 6 amino acids to about 18 amino acids, about 7 amino acids to about 16 amino acids, about 8 amino acids to about 14 amino acids, and about 9 amino acids to about 12 amino acids. Exemplary flexible linkers include glycine polymers $(G)_n$, glycine-serine polymers (including, for example, $(GS)_n$, $(GSGGS)_n$ (SEQ ID NO:90) and $(GGGS)_n$ (SEQ ID NO:91), where n is an integer of at least one), glycine-alanine polymers, alanine-serine polymers, and other flexible linkers such as the tether for the shaker potassium channel, and a large variety of other flexible linkers, as will be appreciated by those in the art. Glycine and glycine-serine polymers are of interest since both of these amino acids are relatively unstructured, and therefore may be able to serve as a neutral tether between components. Glycine polymers are of particular interests glycine accesses significantly more phi-psi space than even alanine, and is much less restricted tan residues with longer side chains (see Scheraga, Rev. Computational Chem. 11173-142 (1992)). Exemplary flexible linkers include, but are not limited Gly-Gly-Ser-Gly-Gly (SEQ ID NO:92), Gly-Ser-Gly-Ser-Gly (SEQ ID NO:93), Gly-Ser-Gly-Gly-Gly (SEQ ID NO:94), Gly-Gly-Gly-Ser-Gly (SEQ ID NO:95), Gly-Ser-Ser-Ser-Gly (SEQ ID NO:96), and the like.

Concatameric ald tag constructs containing a linker can be described by the general formula:

where $T_1$ and $T_2$ are the same or different ald tags as described herein (see, e.g., formulae I, Ia, I', Ia', II, IIa, III, and IIIa), L is a linker peptide, and n is an integer of 1 or more, and may be 2, 3, 4, 5, 6, 7, 8 or more. An exemplary amino acid sequence of a concatameric ald tag containing a linker is LCTPSR GGGG LCTPSR (SEQ ID NO:97), where the cysteine (C) is modified to an FGly by action of an FGE, and can be reacted with a reactive partner-containing drug to provide for covalently bound drug as described herein.

The aldehyde tag(s) can be positioned in the carrier protein so as to take into account its structure when folded (e.g., in a cell-free environment, usually a cell-free physiological environment), e.g., so as to provide the aldehyde tag at a solvent accessible site in the folded carrier protein. The solvent accessible aldehyde tag can thus be accessed in the folded, unconverted ald-tagged carrier protein so as to be accessible to an FGE for conversion of the serine or cysteine to an FGly and/or to a reactive partner reagent for conjugation to a drug of interest. Where an aldehyde tag is positioned at a solvent accessible site, in vitro FGE-mediated conversion and modification with a moiety by reaction with a reactive partner can be performed without the need to denature the protein. Solvent accessible sites can also include carrier protein regions that are exposed at an extracellular or intracellular cell surface when expressed in a host cell.

Accordingly, or more aldehyde tags can be provided at sites independently selected from, for example, a solvent accessible N-terminus, a solvent accessible N-terminal region, a solvent accessible C-terminus, a solvent accessible C-terminal region, and/or a loop structure. In some embodiments, the aldehyde tag is positioned at a site other than the C-terminus of the polypeptide. In other embodiments, the polypeptide in which the aldehyde tag is positioned is a full-length polypeptide.

In other embodiments, an aldehyde tag site is positioned at a site which is post-translationally modified in the parent carrier protein (e.g., a naturally-occurring site). For example, an aldehyde tag can be introduced at a site of glycosylation (e.g., N-glycosylation, O-glycosylation), phosphorylation, sulftation, ubiquitination, acylation, methylation, prenylation, hydroxylation, carboxylation, and the like in the native carrier protein. In addition or alternatively the site of post-translational modification can be one that has been engineered (e.g., through recombinant techniques) and does not occur naturally in the carrier protein.

Figure 3:
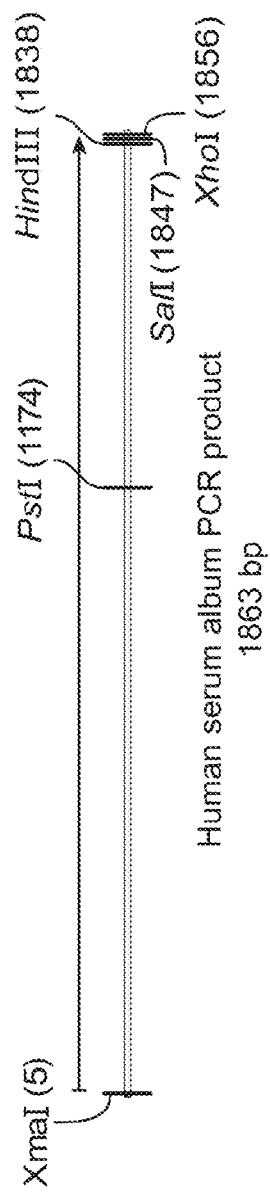
FIG. 3 is a schematic providing an amino acid sequence (SEQ ID NO:70) and nucleic acid sequence (SEQ ID NO:71) of human serum albumin (HSA).

Nucleic and amino acid sequences of polypeptides suitable for use as ald-tagged carrier proteins as described herein are available in the art. For example, FIG. 3 provides the amino acid sequence and encoding nucleic acid sequence for human serum albumin (HSA). Once provided the guidance of the present disclosure, the ordinarily skilled artisan can readily generate ald-tagged HSA useful in the methods and compositions disclosed herein. Exemplary ald-tagged HSA amino acid and encoding nucleic acid sequences are provided in FIG. 4. Exemplary ald-tagged HSA amino acid sequences are provided in FIG. 4, with the corresponding encoding nucleic acid sequences provided in FIGS. 5-9. The three-dimensional structure of HSA is provided in the top panel of FIG. 10.

Further exemplary ald-tagged carrier proteins include ald-tagged Fc fragment. FIG. 11 provides the amino acid sequences of exemplary ald-tagged mouse IgG1 Fc fragments having single and multiple ald tags, including exemplary ald-tagged Fc fragments containing an ald tag concatmer with two ald tags separated by a linker.

Ald-tagged Carrier Protein Libraries

As exemplified in the schematic of FIG. 1B, the carrier protein can be modified to contain an ald tag at different positions to provide a library composed of differently ald-tagged carrier proteins, e.g., ald-tagged carrier proteins having an ald-tag at one or more of the N-terminus, the C-terminus, an interior loop and the like. The members of the ald-tagged carrier protein library can contain 1, 2, 3, 4, 5, or more ald-tags. The library can be provided as a population of expression constructs encoding such ald-tagged carrier proteins for introduction into host cells for expression, e.g., a host cell that expresses an compatible FGE to provide for production of FGly-containing carrier proteins. Alternatively or in addition, the library can be provided as a population or recombinant host cells that are genetically modified to express the ald-tagged carrier protein and which, optionally, express a compatible FGE.

Such libraries can serve as a "plug and play" system for reaction of the produced ald-tagged carrier proteins with a candidate drug having a reactive partner (e.g., an aminooxy or hydrazide moiety). The reaction productions of drug-carrier protein conjugates can then be screened for desired characteristics (e.g., biological activity of the drug, low immunogenicity of the conjugate, and the like).

Formylglycine Generating Enzymes (FGEs)

A formylglycine generating enzyme (FGE) is an enzyme that oxidizes cysteine or serine in a sulfatase motif to FGly. It should be noted that in general, the literature refers to FGly-generating enzymes that convert a cysteine (C to FGly in a sulfatase motif as FGEs, and refers to enzymes that convert serine (S) to FGly in a sulfatase motif as Ats-B-like. However, for purposes of the present disclosure "FGE" is used generically to refer to both types of FGly-generating enzymes, with the understanding that an appropriate FGE will be selected according to the sulfatase motif (i.e., C-containing or S-containing) present in the modified carrier protein.

In general, the FGE used to facilitate conversion of cysteine or serine to FGly in a sulfatase motif of an aldehyde tag of a carrier protein is selected according to the sulfatase motif present in the aldehyde tag. The FGE can be native to the host cell in which the aldehyde tagged carrier protein is expressed, or the host cell can be genetically modified to express an appropriate FGE. Eukaryotic sulfatases generally contain a cysteine in their sulfatase motif and are modified by the "SUMF1-type" FGE (Cosma et al. Cell 2003, 113, (4), 445-56; Dierks et al. Cell 2003, 113, (4), 435-44). Prokaryotic sulfatases generally contain either a cysteine or a serine in their sulfatase motif and are modified either by the "SUMF1-type" FGE or the "AtsB-type" FGE, respectively (Szameit et al. J Biol Chem 1999, 274, (22), 15375-81). An FGE has been described in *Mycobacterium tuberculosis* (see, e.e.g GenBank Acc. No. NP_215226 (gi: 15607852) and WO 2008/036350). FGEs have also been described in deuterostomia, including vertebrates and echinodermata (see, e.g., Pepe et al. (2003) Cell 113, 445-456, Dierks et al. (2003) Cell 113, 435-444; Cosma et al. (2004) *Hum. Mutat.* 23, 576-581). In some embodiments it may be desired to use a sulfatase motif compatible with a human FGE (e.g., the SUMF1-type FGE, see, e.g., Cosma et al. Cell 113, 445-56 (2003); Dierks et al. Cell 113, 435-44 (2003)), and express the aldehyde tagged protein in a human cell that expresses the FGE or in a host cell, usually a mammalian cell, genetically modified to express a human FGE.

In general, an FGE for use in the methods disclosed herein can be obtained from naturally occurring sources or synthetically produced. For example, an appropriate FGE can be derived from biological sources which naturally produce an FGE or which are genetically modified to express a recombinant gene encoding an FGE. Nucleic acids encoding a number of FGEs are known in the art and readily available (see, e.g., Preusser et al. 2005 J. Biol. Chem. 280(15):14900-10 (Epub 2005 Jan. 18); Fang et al. 2004 J Biol Chem. 79(15):14570-8 (Epub 2004 Jan. 28); Landgrebe et al. Gene. 2003 Oct. 16; 316:47-56; Dierks et al. 1998 FEBS Lett. 423(1):61-5; Dierks et al. Cell. 2003 May 16; 113(4):435-44; Cosma et al. (2003 May 16) Cell 113(4):445-56; Baenziger (2003 May 16) Cell 113(4):421-2 (review); Dierks et al. Cell. 2005 May 20; 121(4):541-52; Roeser et al. (2006 Jan. 3)Proc Natl Acad Sci USA 103(1):81-6; Sardiello et al. (2005 Nov. 1) Hum Mol Genet. 14(21):3203-17; WO 2004/072275; GenBank Accession No. NM_182760; and WO 2008/036350). Accordingly, the disclosure here provides for recombinant host cells genetically modified to express an FGE that is compatible for use with an aldehyde tag of a tagged carrier protein.

Where a cell-free method is used to convert a sulfatase motif-containing carrier protein, an isolated FGE can be used. Any convenient protein purification procedures may be used to isolate an FGE, see, e.g., Guide to Protein Purification, (Deuthser ed.) (Academic Press, 1990). For example, a lysate may prepared from a cell the produces a desired FGE, and purified using HPLC, exclusion chromatography, gel electrophoresis, affinity chromatography, and the like.

Expression Vectors and Host Cells for Production of Aldehyde Tagged-Carrier Polypeptides The present disclosure provides nucleic acid encoding ald-tagged carrier polypeptides, as well as constructs and host cells containing nucleic acid. Such nucleic acids comprise a sequence of DNA having an open reading frame that encodes an aldehyde tagged carrier protein and, in most embodiments, is capable, under appropriate conditions, of being expressed. "Nucleic acid" encompasses DNA, cDNA, mRNA, and vectors comprising such nucleic acids.

Nucleic acids contemplated herein can be provided as part of a vector (also referred to as a construct), a wide variety of which are known in the art and need not be elaborated upon herein. Exemplary vectors include, but are not limited to, plasmids; cosmids; viral vectors (e.g., retroviral vectors); non-viral vectors; artificial chromosomes (YAC's, BAC's, etc.); mini-chromosomes; and the like. The choice of vector will depend upon a variety of factors such as the type of cell in which propagation is desired and the purpose of propagation.

Vectors can provide for extrachromosomal maintenance in a host cell or can provide for integration into the host cell genome. Vectors are amply described in numerous publications well known to those in the art, including, e.g., Short Protocols in Molecular Biology, (1999) F. Ausubel, et al., eds., Wiley & Sons. Vectors may provide for expression of the nucleic acids encoding a polypeptide of interest (e.g., an aldehyde tagged polypeptide, an FGE, etc.), may provide for propagating the subject nucleic acids, or both.

Exemplary vectors that may be used include but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include λgt10, λgt11, λgt18-23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors. Alternatively, recombinant virus vectors may be engineered, including but not limited to those derived from viruses such as herpes virus, retroviruses, vaccinia virus, poxviruses, adenoviruses, adeno-associated viruses or bovine papilloma virus.

For expression of a polypeptide of interest, an expression cassette may be employed. Thus, the present invention provides a recombinant expression vector comprising a subject nucleic acid. The expression vector provides a transcriptional and translational regulatory sequence, and may provide for inducible or constitutive expression, where the coding region is operably linked under the transcriptional control of the transcriptional initiation region, and a transcriptional and translational termination region. These control regions may be native to the gene encoding the polypeptide (e.g., the carrier protein or the FGE), or may be derived from exogenous sources. In general, the transcriptional and translational regulatory sequences may include, but are not limited to, promoter sequences, ribosomal binding sites, transcriptional start and stop sequences, translational start and stop sequences, and enhancer or activator sequences. In addition to constitutive and inducible promoters, strong promoters (e.g., T7, CMV, and the like) find use in the constructs described herein, particularly where high expression levels are desired in an in vivo (cell-based) or in an in vitro expression system. Further exemplary promoters include mouse mammary tumor virus (MMTV) promoters, Rous sarcoma virus (RSV) promoters, adenovirus promoters, the promoter from the immediate early gene of human CMV (Boshart et al., *Cell* 41:521-530, 1985), and the promoter from the long terminal repeat (LTR) of RSV (Gorman et al., *Proc. Natl. Acad. Sci. USA* 79:6777-6781, 1982). The promoter can also be provided by, for example, a 5'UTR of a retrovirus.

Expression vectors generally have convenient restriction sites located near the promoter sequence to provide for the insertion of nucleic acid sequences encoding proteins of interest. A selectable marker operative in the expression host may be present to facilitate selection of cells containing the vector. In addition, the expression construct may include additional elements. For example, the expression vector may have one or two replication systems, thus allowing it to be maintained in organisms, for example in mammalian or insect cells for expression and in a prokaryotic host for cloning and amplification. In addition the expression construct may contain a selectable marker gene to allow the selection of transformed host cells. Selection genes are well known in the art and will vary with the host cell used.

Expression constructs encoding aldehyde tagged carrier proteins can also be generated using amplification methods (e.g., polymerase chain reaction (PCR)), where at least one amplification primer (i.e., at least one of a forward or reverse primer) includes a nucleic acid sequence encoding an aldehyde tag. For example, an amplification primer having an aldehyde tag-encoding sequence is designed to provide for amplification of a nucleic acid encoding a carrier protein of interest. The extension product that results from polymerase-mediated synthesis from the aldehyde tag-containing forward primer produces a nucleic acid amplification product encoding a fusion protein composed of an aldehyde tagged-carrier protein. The amplification product is then inserted into an expression construct of choice to provide an aldehyde tagged polypeptide expression construct.

Host Cells

Any of a number of suitable host cells can be used in the production of an aldehyde tagged carrier protein. The host cell used for production of an aldehyde tagged-carrier protein can optionally provide for FGE-mediated conversion, so that the polypeptide produced contains an FGly-containing aldehyde tag following expression and post-translational modification by FGE. Alternatively the host cell can provide for production of an unconverted aldehyde tagged carrier protein (e.g., due to lack of expression of an FGE that facilitates conversion of the aldehyde tag).

In general, the polypeptides described herein may be expressed in prokaryotes or eukaryotes in accordance with conventional ways, depending upon the purpose for expression. Thus, the present invention further provides a host cell, e.g., a genetically modified host cell that comprises a nucleic acid encoding an aldehyde tagged polypeptide. The host cell can further optionally comprise a recombinant FGE, which may be endogenous or heterologous to the host cell.

Host cells for production (including large scale production) of an unconverted or (where the host cell expresses a suitable FGE) converted aldehyde tagged carrier protein, or for production of an FGE (e.g., for use in a cell-free method) can be selected from any of a variety of available host cells. Exemplary host cells include those of a prokaryotic or eukaryotic unicellular organism, such as bacteria (e.g., *Escherichia coli* strains, *Bacillus* spp. (e.g., *B. subtilis*), and the like) yeast or fungi (e.g., *S. cerevisiae*, *Pichia* spp., and the like), and other such host cells can be used. Exemplary host cells originally derived from a higher organism such as insects, vertebrates, particularly mammals, (e.g. CHO, HEK, and the like), may be used as the expression host cells.

Specific expression systems of interest include bacterial, yeast, insect cell and mammalian cell derived expression systems. Representative systems from each of these categories are provided below.

The product can be recovered by any appropriate means known in the art. Further, any convenient protein purification procedures may be employed, where suitable protein purification methodologies are described in Guide to Protein Purification, (Deuthser ed.) (Academic Press, 1990). For example, a lysate may prepared from a cell comprising the expression vector expressing the ald-tagged carrier protein, and purified using HPLC, exclusion chromatography, gel electrophoresis, affinity chromatography, and the like.

Methods for Conversion and Modification of an Aldehyde Tag

Conversion of an aldehyde tag present in an aldehyde tagged carrier protein can be accomplished by cell-based (in vivo) or cell-free methods (in vitro). Similarly, modification of a converted aldehyde tag of an aldehyde tagged polypeptide can be accomplished by cell-based (in vivo) or cell-free methods (in vitro). These are described in more detail below.

"In Vivo" Host Cells Conversion and Modification

Conversion of an aldehyde tag of an aldehyde tagged polypeptide can be accomplished by expression of the aldehyde tagged polypeptide in a cell that contains a suitable FGE. In this embodiment, conversion of the cysteine or serine of the aldehyde tag is occurs during or following translation in the host cell. The FGE of the host cell can be endogenous to the host cell, or the host cell can be recombinant for a suitable FGE that is heterologous to the host cell. FGE expression can be provided by an expression system endogenous to the FGE gene (e.g., expression is provided by a promoter and other control elements present in the native FGE gene of the host cell), or can be provided by from a recombinant expression system in which the FGE coding sequence is operably linked to a heterologous promoter to provide for constitutive or inducible expression.

Conditions suitable for use to accomplish conjugation of a reactive partner moiety to an aldehyde tagged polypeptide are similar to those described in Mahal et al. (1997 May 16) Science 276(5315):1125-8.

"In Vitro" (Cell-Free) Conversion and Modification

In vitro (cell-free) conversion of an aldehyde tag of an aldehyde tagged carrier protein can be accomplished by contacting an aldehyde tagged polypeptide with an FGE under conditions suitable for conversion of a cysteine or serine of a sulfatase motif of the aldehyde tag to a FGly. For example, nucleic acid encoding an aldehyde tagged polypeptide can be expressed in an in vitro transcription/translation system in the presence of a suitable FGE to provide for production of converted aldehyde tagged polypeptides.

Alternatively, isolated, unconverted aldehyde tagged carrier protein can be isolated following recombinant production in a host cell lacking a suitable FGE or by synthetic production. The isolated aldehyde tagged carrier protein is then contacted with a suitable FGE under conditions to provide for aldehyde tag conversion. The aldehyde tagged carrier protein can be unfolded by methods known in the art (e.g., using heat, adjustment of pH, chaotropic agents, (e.g., urea, and the like), organic solvents (e.g., hydrocarbons: octane, benzene, chloroform), etc.) and the denatured protein contacted with a suitable FGE. The ald-tagged carrier protein can then be refolded under suitable conditions.

With respect to modification of converted aldehyde tagged, modification is normally carried out in vitro. Converted aldehyde tagged carrier protein is isolated from a production source (e.g., recombinant host cell production, synthetic production), and contacted with a reactive partner-containing drug under conditions suitable to provide for conjugation of a moiety of the reactive partner to the FGly of the aldehyde tag.

Drugs for Conjugation to Ald-Tagged Carrier Proteins

Any of a number of drugs are suitable for use, or can be modified to be rendered suitable for use, as a reactive partner to conjugate to an ald tagged-carrier protein. Exemplary drugs include small molecule drugs and peptide drugs.

"Small molecule drug" as used herein refers to compound, usually an organic compound, which exhibits a pharmaceutical activity of interest and which is generally of a molecular weight of no greater than about 800 Da, and usually no greater than 2000 Da, but can encompass molecules of up to 5 kDa and can be as large as about 10 kDa. A small inorganic molecule refers to a molecule containing no carbon atoms, while a small organic molecules refers to a compound containing at least one carbon atom.

"Peptide drug" as used herein refers to amino-acid containing polymeric compounds, and is meant to encompass naturally-occurring and non-naturally-occurring peptides, oligopeptides, cyclic peptides, polypeptides, and proteins, as well as peptide mimetics. The peptide drugs may be obtained by chemical synthesis or be produced from a genetically encoded source (e.g., recombinant source). Peptide drugs can range in molecular weight, and can be from 200 Da to 10 kDa or greater in molecular weight.

Glucagon-like peptide 1 (GLP-1), calcitonin, and biologically active fragments and variants thereof are exemplary peptide drugs. By "variant" is meant a polypeptide that has an amino acid sequence that is not found in nature, and includes polypeptides having one or more amino acid substitutions, insertions and/or deletions relative to a naturally-occurring parent polypeptide. "Variant" polypeptides thus encompass a polypeptide having an N- or C-terminal truncation relative to a parent polypeptide. A "fragment" of a polypeptide is one that shares an amino acid sequence of a naturally-occurring polypeptide, but that is truncated at the N-terminus, C-terminus or both relative to a naturally-occurring parent polypeptide.

GLP-1 is one of several naturally occurring incretin compounds that possess biologic activity when released from the gut during digestion. GLP-1 naturally works on several deficient organs to lower blood sugar levels. It is able to significantly delay the progression of Type 2 diabetes, and is useful in treatment of hyperglycemis. Currently, GLP-1 is less useful as a drug because it is broken down within minutes by the enzyme DPP-4, which is present throughout the human body. Coupling of GLP1 to an ald-tagged carrier protein can provide for increased serum half-lifeGLP-1 and biologically active fragments and variants thereof represent an exemplary peptide drug of interest for conjugation to a ald-tagged carrier protein of the present disclosure. Exemplary fragments and variants of GLP-1 include, but are not necessarily limited to, those described in Green et al. 2007 Best Pract Res Clin Endocrinol Metab 21:497-516; Brubaker et al. 2007 Trends Endocrinol Metab 18:240-245; Boyle et al. 2007 J Am Osteopath Assoc 107(Suppl):S10-S16; and Drucker et al. 2006 The incretin system: glucagon-like peptide-1 receptor agonists and dipeptidyl peptidase-4 inhibitors in type 2 diabetes. Lancet 368:1696-1705 32. Exemplary biologically active GLP-1 variants include those having, for example, an amino acid substitution at amino acid residues His(7), Ala(8), or Glu(9) of the native GLP-1 amino acid sequence. Specific examples include (D-His7) GLP-1, (D-Ala8)GLP-1, (Gly8)GLP-1, (Ser8)GLP-1, (Aha8)GLP-1, (Thr8)GLP-1, (Aib8)GLP-1, (Abu8)GLP-1, (Va18)GLP-1, (Asp9)GLP-1, (Ala9)GLP-1, (Pro9)GLP-1, (Phe9)GLP-1, and (Lys9)GLP-1. Specific exemplary biologically active GLP-1 variants are known as Exenatide, LY548806, CJC-1131, and Lirglutide.

Calcitonin and biologically active variants thereof represent an exemplary peptide drug of interest for conjugation to an ald-tagged carrier protein of the present disclosure.

Calcitonin is a 32 amino-acid linear polypeptide hormone that is produced in humans primarily by the parafollicular (also known as C-cells) of the thyroid. Calcitonin has short absorption and elimination half-lives of 10-15 minutes and 50-80 minutes, respectively and can be used therapeutically for the treatment of hypercalcaemia or osteoporosis. Conjugation of calcintonin to an ald-tagged carrier protein as disclosed herein can provide for enhanced serum half-life, and thus provide for a therapeutic that can be administered much less frequently then the peptide alone. Exemplary biologically active calcitonin variants include, but are not necessarily limited to, those described in Fowler et al. Proc Natl Acad Sci USA. 2005 Jul. 19; 102(29):10105-10.

The biological activity of drug conjugated to an ald-tagged carrier protein as disclosed herein can be assayed according to methods known in the art. Such conjugated drugs that retain at least one desired pharmacologic activity of the corresponding parent compound are of interest.

Figure 2:
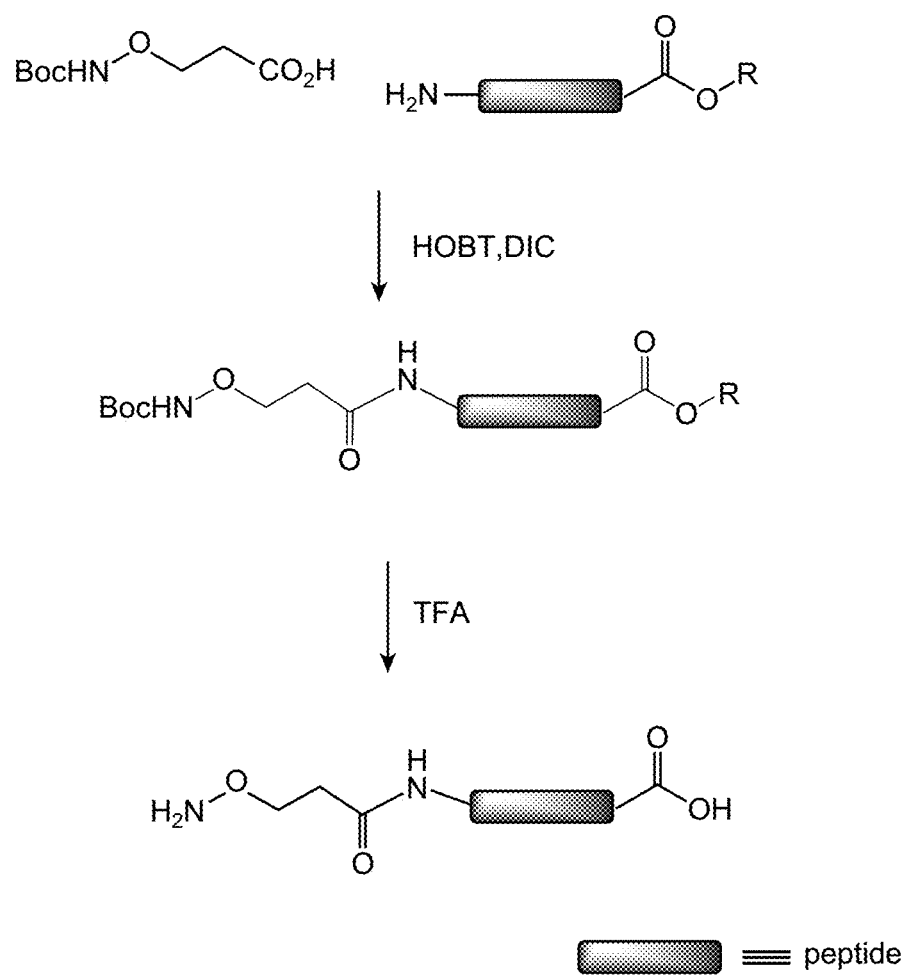
FIG. 2 is schematic illustrating an exemplary synthesis of peptides to contain a reactive partner for reaction with an aldehyde group of an ald-tagged carrier protein.

Methods for Modification of Drugs to Contain Reactive Partner for Reaction with 2-formylglycine Peptide drugs to be conjugated to an ald-tagged carrier protein are modified to incorporate a reactive partner for reaction with an aldehyde of the FGly residue of the ald-tagged carrier protein. Since the methods of ald-tagged polypeptide modification are compatible with conventional chemical processes, any of a wide variety of commercially available reagents can be used to accomplish conjugation. For example, aminooxy, hydrazide, hydrazine, or thiosemicarbazide derivatives of a number of moieties of interest are suitable reactive partners, and are readily available or can be generated using standard chemical methods.

Where the drug is a peptide drug, the reactive moiety (e.g., aminooxy or hydrazide can be positioned at an N-terminal region, the N-terminus, a C-terminal region, the C-terminus, or at a position internal to the peptide. FIG. 2 provides a schematic of an exemplary method for synthesizing a peptide drug having an aminooxy group. In this example, the peptide is synthesized from a Boc-protected precursor. An amino group of a peptide can react with a compound comprising a carboxylic acid group and oxy-N-Boc group. As shown in FIG. 2 for example, the amino group of the peptide reacts with 3-(2,5-dioxopyrrolidin-1-yloxy)propanoic acid. Other variations on the compound comprising a carboxylic acid group and oxy-N-protecting group can include different number of carbons in the alkylene linker and substituents on the alkylene linker. The reaction between the amino group of the peptide and the compound comprising a carboxylic acid group and oxy-N-protecting group occurs through standard peptide coupling chemistry. Examples of peptide coupling reagents that can be used include, but not limited to, DCC (dicyclohexylcarbodiimide), DIC (diisopropylcarbodiimide), di-p-toluoyl-carbodiimide, BDP (1-benzotriazole diethylphosphate-1-cyclohexyl-3-(2-morpholinylethyl)carbodiimide), EDC (1-(3-dimethylaminopropyl-3-ethyl-carbodiimide hydrochloride), cyanuric fluoride, cyanuric chloride, TFFH (tetramethyl fluoroformamidinium hexafluorophosphosphate), DPPA (diphenylphosphorazidate), BOP (benzotriazol-1-yloxytris(dimethylamino)phosphonium hexafluorophosphate), HBTU (O-benzotriazol-1-yl-N,N,N',N-tetramethyluronium hexafluorophosphate), TBTU (O-benzotriazol-1-yl-N,N,N', N'-tetramethyluronium tetrafluoroborate), TSTU (O-(N-succinimidyl)-N,N,N',N'-tetramethyluronium tetrafluoroborate), HATU (N-[(dimethylamino)-1-H-1,2,3-triazolo[4,5,6]-pyridin-1-ylmethylene]-N-methylmethanaminium hexafluorophosphate N-oxide), BOP-Cl (bis(2-oxo-3-oxazolidinyl)phosphinic chloride), PyBOP ((1-H-1,2,3-benzo-triazol-1-yloxy)-tris(pyrrolidino)phosphonium tetrafluorophopsphate), BrOP (bromotris(dimethylamino) phosphonium hexafluorophosphate), DEPBT (3-(diethoxyphosphoryloxy)-1,2,3-benzotriazin-4(3H)-one) PyBrOP (bromotris(pyrrolidino)phosphonium hexafluorophosphate). In FIG. 2, HOBt and DIC are used as peptide coupling reagents.

Deprotection to expose the amino-oxy functionality is performed on the peptide comprising an N-protecting group. Deprotection of the N-oxysuccinimide group, for example, occurs according to standard deprotection conditions for a cyclic amide group. Deprotecting conditions can be found in Greene and Wuts, Protective Groups in Organic Chemistry, 3rd Ed., 1999, John Wiley & Sons, NY and Harrison et al. Certain deprotection conditions include a hydrazine reagent, amino reagent, or sodium borohydride. In FIG. 2, the deprotection of the Boc protecting group occurs with TFA. Other reagents for deprotection include, but are not limited to, hydrazine, methylhydrazine, phenylhydrazine, sodium borohydride, and methylamine. The product and intermediates can be purified by conventional means, such as HPLC purification.

The ordinarily skilled artisan will appreciate that factors such as pH and steric hindrance (i.e., the accessibility of the aldehyde tag to reaction with a reactive partner of interest) are of importance, Modifying reaction conditions to provide for optimal conjugation conditions is well within the skill of the ordinary artisan, and is routine in the art. In general, it is normally desirable to conduction conjugation reactions at a pH below 7, with a pH of about 5.5, about 6, about 6.5, usually about 5.5 being optimal. Where conjugation is conducted with an aldehyde tagged polypeptide present in or on a living cell, the conditions are selected so as to be physiologically compatible. For example, the pH can be dropped temporarily for a time sufficient to allow for the reaction to occur but within a period tolerated by the cell having an aldehyde tag (e.g., from about 30 min to 1 hour). Physiological conditions for conducting modification of aldehyde tagged polypeptides on a cell surface can be similar to those used in a ketone-azide reaction in modification of cells bearing cell-surface azides (see, e.g., U.S. Pat. No. 6,570,040).

Small molecule compounds containing, or modified to contain, an α-nucleophilic group that serves as a reactive partner with an aldehyde of an FGly of an ald tag are also contemplated for use as drugs in the carrier protein-drug conjugates of the present disclosure. General methods are known in the art for chemical synthetic schemes and conditions useful for synthesizing a compound of interest (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Figure 12:
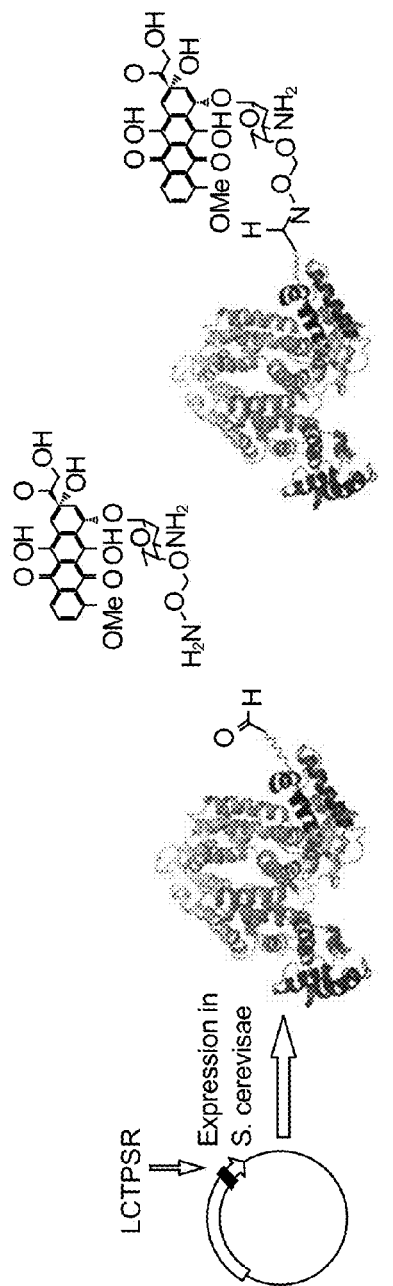
FIG. 12 is a schematic of an exemplary ald-tagged carrier protein modified by conjugation to a small molecule drug. The N-terminal end of the protein is on the right side of the schematic; the C-terminal end of the protein is on the left side of the schematic. The aldehyde tag is exemplified in FIG. 12 by LCTPSR (SEQ ID NO:1).

Thus small molecules having an aminooxy or hydrazone group for reaction with an aldehyde of an FGly of an ald-tagged carrier protein group are available or can be readily synthesized. An aminooxy or hydrazone group can be installed onto a small molecule using standard synthetic chemistry techniques. FIG. 12 provides a schematic of an exemplary ald-tagged carrier protein (represented by HSA) modified by conjugation to a small molecule drug (represented by doxorubicin).

Peptide Drug—Carrier Protein Conjugates

The conjugates of the present disclosure are site-specifically decorated with covalently bound drug. The site-specificity of reaction of a reactive partner-containing drug with an aldehyde tag of the carrier protein allows for production of carrier proteins having multiple sites for chemical conjugation, thus providing a scaffold for production of carrier protein-drug conjugates have a desired drug payload per protein ratio. Moreover, the relative position of the ald tags in the ald-tagged carrier protein can be designed so as to provide for a desired presentation of covalently bound drug molecules on the surface of the final carrier protein-drug conjugate, thus allowing for control of spatial orientation of the displayed drug payload.

Further, the site-specific nature of chemical modification of ald tags to attach drug to the carrier protein can be exploited to provide for a composition composed of a substantially homogenous population carrier protein-drug conjugates. Such carrier protein-drug conjugates can provide for control of the stoichiometry of drug delivery.

Carrier protein-drug conjugates of the present disclosure are composed of a carrier protein and one or more covalently bound drug molecules, where the carrier protein comprises a modified sulfatase motif of the formula:

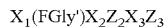

where FGly' is of the formula:

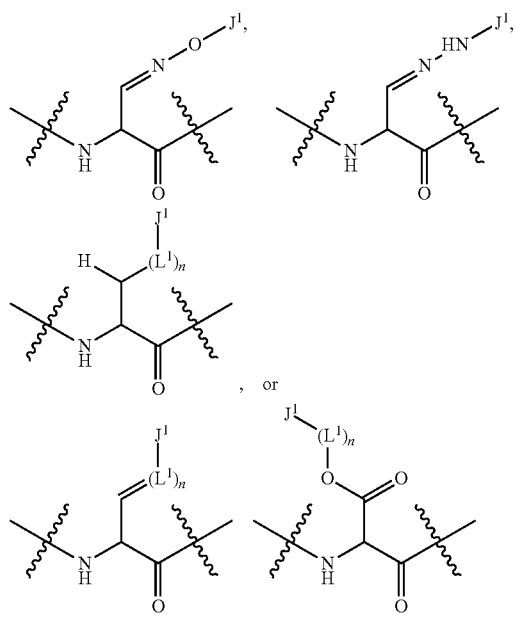

wherein $J^1$ is the covalently bound drug;

each $L^1$ is a divalent moiety independently selected from alkylene, substituted alkylene, alkenylene, substituted alkenylene, alkynylene, alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, —O—, —S—, —NH—, and substituted amine;

n is a number selected from zero to 40;

$Z_2$ is a proline or alanine residue;

$X_1$ is present or absent and, when present, is any amino acid, with the proviso that when the sulfatase motif is at an N-terminus of the polypeptide, $X_1$ is present;

$X_2$ and $X_3$ are each independently any amino acid; and $Z_3$ is a basic amino acid, and wherein the carrier protein presents the covalently bound drug on a solvent-accessible surface when in a folded state. The $X_1$, $X_2$, $Z_2$, $X_3$, and $Z_3$ can be further defined as discussed above.

As noted above, the ald-tagged carrier protein can be designed so as to provide for multiple sites for chemical conjugation, thus providing a scaffold for production of carrier protein-drug conjugates have a desired drug payload per protein ratio. The carrier protein-drug conjugates contemplated by the present disclosure generally include at least 2 modified sulfatase motifs having covalently bound drug molecules, and usually include 3 or more modified sulfatase motifs having covalently bound drug molecules. The carrier protein-drug conjugates of the present disclosure can provide for a 4 or more, 5 or more, or 6 or more covalently bound drug molecules in the carrier protein-drug conjugate. Carrier protein-drug conjugates of the present disclosure thus include those having a drug payload to protein carrier ratio of at least 2:1, at least 3:1, at least 4:1, at least 5:1 and, depending upon, for example, the size of the drug molecule relative to the size of the carrier protein and/or the available sites for insertion of an ald tag on the solvent-accessible surface area of the folded carrier protein.

As noted above, the relative position of the ald tags in the ald-tagged carrier protein can be designed so as to provide for a desired presentation of covalently bound drug molecules on the surface of the final carrier protein-drug conjugate. This feature allows for control of spatial orientation of the displayed drug payload on the surface of the final carrier protein-drug conjugate. Carrier protein-drug conjugates containing multiple ald tags, which may include concatameric ald tags separated by flexible linkers as described herein, can provide for greater drug payload:carrier protein ratios and enhanced presentation of drug to a physiological environment in which the carrier protein-drug conjugate is present. As such, the carrier protein-drug conjugates can be described as a modified carrier protein "decorated" with drug covalently bound to the carrier protein through an oxime or hydrazone linkage to the peptide backbone of the carrier protein.

For example, the ald tags of the carrier protein-drug conjugate can be positioned in the carrier protein-drug conjugate at at least one of an N-terminus of the carrier protein, a C-terminus of the carrier protein, and a solvent-accessible loop of the carrier protein. The ald tags can optionally be provided in connection with a linker, e.g., a flexible linker, as described above. The multiple ald tags can be localized to a particular region(s) of the carrier protein (e.g., provided in one or more of a solvent-accessible loop, N-terminal region (including N-terminus), C-terminal region (including C-terminus)), or can be distributed over the solvent-accessible surface area of the folded modified carrier protein.

Figure 10:
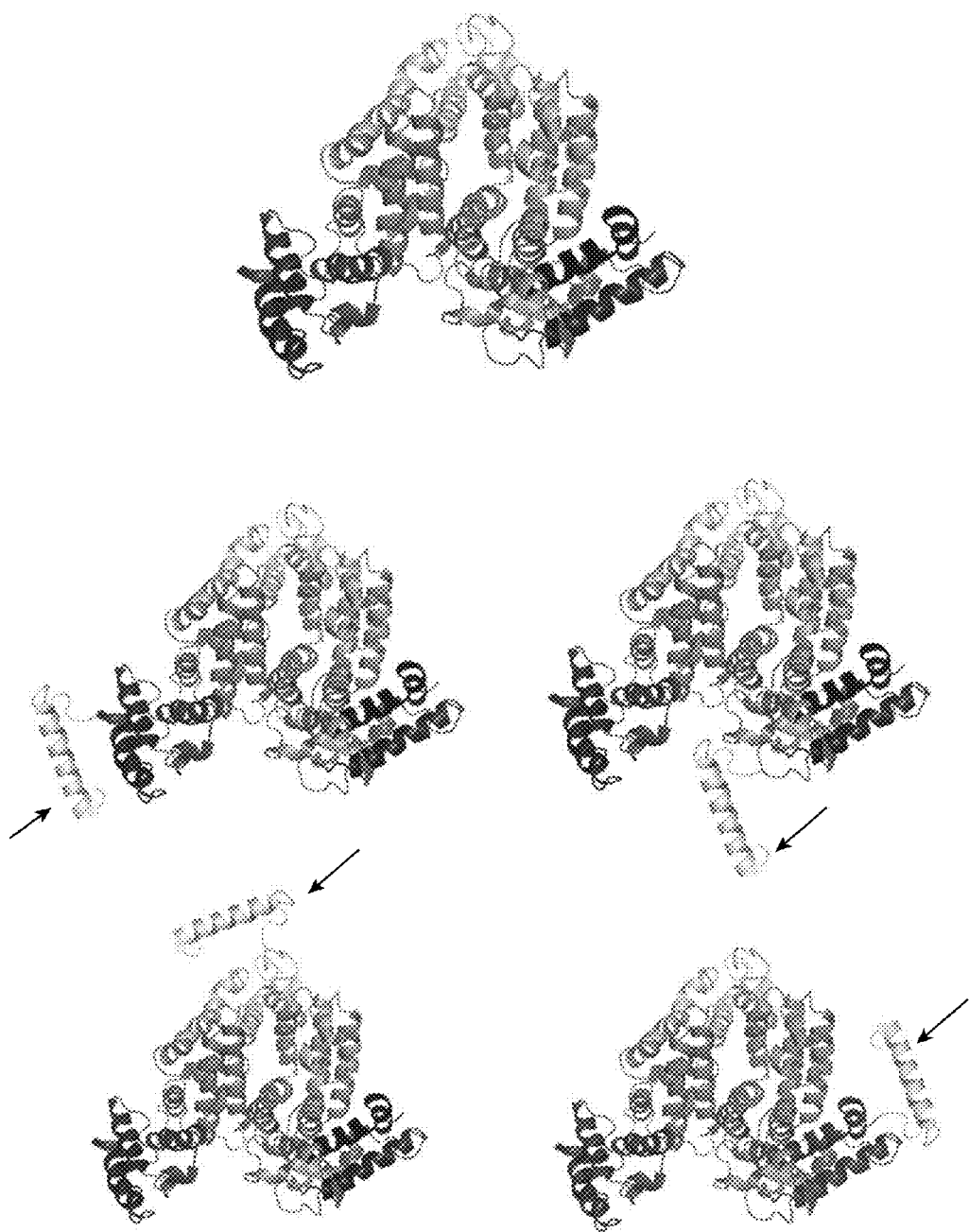
FIG. 10 is a schematic illustrating (top panel) the crystal structure of a recombinant HSA and (bottom panel) a carrier protein-drug conjugate of an ald-tagged recombinant HSA and GLP-1, with the GLP-1 peptide shown in the same scale as the HSA carrier protein. In each panel, the N-terminal end of the protein is on the right side of the schematic; the C-terminal end of the protein is on the left side of the schematic.

In general, it may be desirable to space the ald tags of the ald-tagged carrier protein so that the final carrier protein-drug conjugate has covalently bound drug spaced apart at a distance sufficient to avoid interaction between the covalently bound drug molecules, e.g., so that drug molecules do not contact one another or otherwise interfere with their respective biological activities. The spatial orientation and positioning within the carrier protein will vary according to a variety of factors including the relative sizes of the drug to be conjugated and the carrier protein. FIG. 10, bottom panel, provides a schematic of the three-dimensional structure exemplifying an ald-tagged recombination HSA having a covalently bound GLP-1 peptide at its N-terminus.

As noted above, the site-specific nature of chemical modification of ald tags to attach drug to the carrier protein can be exploited to provide for a composition composed of a substantially homogenous population carrier protein-drug conjugates. Such carrier protein-drug conjugates can provide for control of the stoichiometry of drug delivery. Such homogenous populations of carrier protein-drug conjugates include those in which at least 60%, at least 70%, at least 80% at least 90% or more of the carrier protein-drug conjugates of the population have the same drug payload to carrier protein ratio.

Methods of Making Carrier Protein-drug Conjugates

Methods of conjugation of an FGly-containing ald-tagged carrier protein with a reactive-partner containing-drug to provide a carrier protein-drug conjugate having a desired drug payload:carrier protein ratio are contemplated by the present disclosure. In general, such methods involve combining an FGly-containing, ald-tagged carrier protein with a reactive partner-containing drug (e.g., an aminooxy- or hydrazide-containing drug) in a reaction mixture under conditions suitable to promote reaction between the aldehyde(s) for the FGly(s) of the ald-tagged carrier protein with the reactive partner of the drug molecule(s), thereby producing a reaction product of a carrier protein-drug conjugate having drug covalently bound to the peptide backbone of the carrier protein through an oxime bond, hydrazide bond, or other aldehyde specific chemistries such as reductive aminations, or Wittig reactions.

After production of the ald-tagged carrier protein, it is isolated using any of a variety of techniques available in the art (e.g., chromatography, e.g., HPLC, FPLC, immunoaffinity purification, and the like). In some embodiments, the carrier protein of the carrier protein-drug conjugate contains an immunotag (e.g., His tag, FLAG tag), usually positioned at an N- or C-terminus to facilitate isolation and purification prior to conjugation with drug. The FGly-containing ald-tagged carrier protein for use in a conjugation reaction with drug can be provided in denatured form or can be folder prior to combining in the reaction mixture. Usually, the FGly-containing ald-tagged carrier protein is provided in folded form in the conjugation reaction mixture. Where obtained from cells expressing the ald-tagged carrier protein and a compatible FGE, the FGly-containing ald-tagged carrier protein can be isolated in folded form from cells or, where secreted, from culture supernatant. Where needed, methods for folding of proteins are available in the art, and can be readily applied to the methods here.

In general, the ald-tagged carrier protein having FGly residues is isolated, and usually is purified. The carrier protein-drug conjugate is combined in a reaction mixture in buffered solution with a reactive partner-containing drug. The buffered solution can be at a physiological or near physiological pH, e.g., a pH of about 5 to 7, usually a pH of about 6.5. The reactive partner-containing drug is provided in the reaction mixture in excess to the aldehyde moieties of the FGly-containing ald-tagged carrier protein, usually at least 2 fold, 3 fold, 4 fold, 5 fold or more excess, in order drive the reaction to completion. After addition of reactive partner-containing drug to the reaction mixture, the mixture is stirred under suitable conditions of time and temperature (e.g., at room temperature for about 2 h). The resulting carrier protein-drug conjugate is isolated from the reaction mixture and can be further purified using standard techniques (e.g., chromatography, e.g., HPLC, FPLC).

Assessment of Carrier Protein-drug Conjugate Activity

Following isolation of a carrier protein-drug conjugate from a reaction mixture, the carrier protein-drug conjugate can be screened for activity in one or more assays. Such assays can be for one or more biological activities of the drug conjugated to the carrier protein-drug conjugate and/or for one or more characteristics of the carrier protein-drug conjugate (e.g., immunogenicity).

Methods for assessing immunogenicity are available in the art and can be adapted for use in assessing carrier protein-drug conjugates of the present disclosure. For example, the carrier protein-drug conjugate can be administered to a non-human animal (e.g., an animal that can serve as a model for a human immune response), and the immune response to the carrier protein-drug conjugate assessed. Carrier protein-drug conjugates can be assessed for their activity in eliciting a humoral and/or cellular immune response in a non-human animal. Of particular interest is the production of anti-carrier protein-drug conjugate antibodies by the immunized host. Methods for assessing antibody production in a host are well known in the art.

Methods for assessing activity of the drug conjugated to the carrier protein-drug conjugate are selected according to the drug bound to the carrier protein-drug conjugate and are available in the art. Such assays can be in vitro cell-free assays, in vitro cell-based assays, or in vivo assays (e.g., in an animal model). Usually the assay is a cell-based in vitro functional assay or an in vivo assay using a non-human animal model (e.g, an animal model of human disease).

For example, activity of a carrier protein-GLP-1 conjugate of the present disclosure can be assayed in a cellular receptor activity assay, as exemplified in the Example below. Activity of a carrier protein-calicitonin conjugate of the present disclosure can be assayed in a bone cell culture system to assess bone resorption of calcium.

Formulations

The carrier protein-drug conjugates of the present disclosure can be formulated in a variety of different ways. In general, the carrier protein-drug conjugate is formulated in a manner compatible with the drug conjugated to the carrier protein-drug conjugate, the condition to be treated, and the route of administration to be used.

The carrier protein-drug conjugate can be provided in any suitable form, e.g., in the form of a pharmaceutically acceptable salt, and can be formulated for any suitable route of administration, e.g., oral, topical or parenteral administration. Where the carrier protein-drug conjugate is provided as a liquid injectable (such as in those embodiments where they are administered intravenously or directly into a tissue), the carrier protein-drug conjugate can be provided as a ready-to-use dosage form, or as a reconstitutable storage-stable powder or liquid composed of pharmaceutically acceptable carriers and excipients.

Methods for formulating carrier protein-drug conjugates can be adapted from those available in the art. For example, carrier protein-drug conjugates can be provided in a pharmaceutical composition comprising an effective amount of a carrier protein-drug conjugate and a pharmaceutically acceptable carrier (e.g., saline). The pharmaceutical composition may optionally include other additives (e.g., buffers, stabilizers, preservatives, and the like). Of particular interest are formulations that are suitable for administration to a mammal, particularly those that are suitable for administration to a human.

Methods of Treatment

The carrier protein-drug conjugates of the present disclosure find use in treatment of a condition or disease in a subject that is amenable to treatment by administration of the parent drug (i.e., the drug prior to conjugation to the carrier protein. By "treatment" is meant that at least an amelioration of the symptoms associated with the condition afflicting the host is achieved, where amelioration is used in a broad sense to refer to at least a reduction in the magnitude of a parameter, e.g. symptom, associated with the condition being treated. As such, treatment also includes situations where the pathological condition, or at least symptoms associated therewith, are completely inhibited, e.g., prevented from happening, or stopped, e.g. terminated, such that the host no longer suffers from the condition, or at least the symptoms that characterize the condition. Thus treatment includes: (i) prevention, that is, reducing the risk of development of clinical symptoms, including causing the clinical symptoms not to develop, e.g., preventing disease progression to a harmful state; (ii) inhibition, that is, arresting the development or further development of clinical symptoms, e.g., mitigating or completely inhibiting an active disease; and/or (iii) relief, that is, causing the regression of clinical symptoms.

The subject to be treated can be one that is in need of therapy, where the host to be treated is one amenable to treatment using the parent drug. Accordingly, a variety of subjects may be amenable to treatment using the carrier protein-drug conjugates disclosed herein. Generally such subjects are "mammals", with humans being of particular interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as other primates (e.g., chimpanzees, and monkeys.

The amount of carrier protein-drug conjugate administered can be initially determined based on guidance of a dose and/or dosage regimen of the parent drug. In general, the carrier protein-drug conjugates can provide for enhanced blood serum half-life of the bound drug, thus providing for at least one of reduced dose or reduced administrations in a dosage regimen. Thus the carrier protein-drug conjugates can provide for reduced dose and/or reduced administration in a dosage regimen relative to the parent drug prior to conjugated in a carrier protein-drug conjugate of the present disclosure.

Furthermore, as noted above, because the carrier protein-drug conjugates can provide for controlled stoichiometry of drug delivery, dosages of carrier protein-drug conjugates can be calculated based on the number of drug molecules provided on a per carrier protein-drug conjugate basis.

Accordingly, the carrier protein-drug conjugates of the present disclosure where in the drug is GLP-1, or a biologically active variant thereof, can be used in treatment of conditions amenable to therapy by administration of GLP-1. Such conditions include Type II diabetes and hyperglycemia. Such methods involve administration of an effective amount of a carrier protein-GLP-1 conjugate (or a carrier protein-drug conjugate having a covalently bound variant of GLP-1) to a subject in need to treatment (e.g., a subject having or at risk of Type II diabetes and/or hyperglycemia, wherein administration of the carrier protein-drug conjugate is effect to treat the condition.

Where the drug of the carrier protein-drug conjugates of the present disclosure is Calcitonin, or a biologically active variant thereof, can be used in treatment of conditions amenable to therapy by administration of Calcitonin Such conditions include osteoporosis and hypercalcaemia. Such methods involve administration of an effective amount of a carrier protein-Calcitonin conjugate (or a carrier protein-drug conjugate having a covalently bound variant of Calcitonin) to a subject in need to treatment (e.g., a subject having or at risk of osteoporosis or hypercalcaemia, wherein administration of the carrier protein-drug conjugate is effect to treat the condition.

Kits and Systems

Kits and systems are provided to facilitate and, where desired, standardize the compositions of the invention and the uses thereof. Kits contemplated herein can include one or more of a construct encoding an aldehyde tagged carrier protein (and may encompass a library composed of constructs encoding a population of differently ald-tagged carrier proteins) for expression in a host cell; a host cell that produces an FGE compatible with an aldehyde tag of the kit, where the FGE may be endogenous, recombinant, or heterologous; a host cell genetically modified to express an aldehyde tagged carrier protein (and may encompass a library composed of recombinant host cells containing constructs encoding a population of differently ald-tagged carrier proteins), which host cell can further express an endogenous, recombinant, or heterologous FGE compatible for conversion of the aldehyde tag of the tagged polypeptide; reagents to provide for production of a reactive partner-containing drug; and reagents to promote a reaction between an ald-tagged carrier protein and a reactive partner-containing drug.

In addition, the kit can contain instructions for using the components of the kit, particularly the compositions of the invention that are contained in the kit.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Production of Panel of HSA Carrier Proteins

The ald-tag technology is used to provide for high-efficiency modification of secreted carrier proteins in mammalian cell culture system. An FGE and sulfatase motifs are used to install aldehyde tags in a recombinant human serum albumin (rHSA) in a yeast expression system, e.g., *Saccharomyces cerevisiae*. The FGly-containing ald tag will be exploited to conjugate drugs (e.g., small molecule drugs) to the HSA carrier protein. HSA is trafficked through the secretory pathway, similar to native sulfatases and the previously studied secreted Fc proteins, and are therefore will be readily be recognized as substrates by ER-resident FGE when expressed in mammalian cells. When expressed in yeast, the recombinant HSA containing the aldehyde tag motif is purified and reacted with purified recombinant FGE to convert the cysteine to formylglycine ex vivo, the addition of purified FGE to a purified recombinant protein to give the enzymatic transformation. The converted aldehyde tagged HSA were chemically modified with small molecules to afford a final conjugated protein construct.

C-terminal Modified HSA as a Model Protein

The vector construction utilized the native (human) HSA leader sequence. Modifications to the sequence were made after initial cloning of HSA into a plasmid. A strong promoter was used (for example, Galactose inducible GAL or constitutively-active GPD promoter with -LEU2. For example, the vector p425-GAL1 or the vector p425GalL have a galactose-inducible strong promoter in place with a MCS that can receive the HSA sequence.

Yeast cell lines containing the HSA-Ald$_6$ tag construct were generated using standard molecular biology techniques. After establishing and confirming transformed colonies by PCR, the expression of the Ald$_6$ tagged-HSA was induced and production assayed by immunoblotting. In order to probe directly the aldehyde-modified protein, rHSA was reacted with aminooxy-FLAG peptide and analyzed by Western blot with an anti-FLAG antibody as well as an anti-HSA antibody. The percent conversion of Cys to FGly was quantified by isolation of the protein followed by tryptic digestion and mass spectrometry analysis.

Example 2

Production of Carrier Proteins Having Multiple Ald Tags

Carrier proteins conjugated with multiple peptide drugs or small molecules can greatly enhance the efficacy of the biotherapeutic of interest. Thus multiple aldehyde tags will be installed into a single HSA carrier protein. An HSA carrier protein having Ald$_6$ tags (LCTPSR, (SEQ ID NO:1)) placed in different locations along the peptide backbone of the carrier protein will be generated.

Three different Ald$_6$ tag sequences were appended to the recombinant HSA carrier protein. These constructs, containing Ald$_6$ sequences, are shown in FIG. 6 (depicting three uniquely tagged proteins). The constructs were expressed in S. cerevisae, purified and reacted along with purified M. tuberculosis FGE. Reaction conditions were optimized to maximize the conversion of the cysteine to FGly. The converted protein was purified and analyzed for the presence of FGly by reaction with aminooxy-biotin or aminooxy FLAG peptide followed by Western blot. A CHO expression system was developed for the production of HSA and E. coli expression systems can also be developed for production of ald-tagged rHSAs. The percent conversion of Cys to FGly for each individual tag in the series of multi-ald-tagged rHSAs is assessed by isolation of the protein followed by tryptic digestion and mass spectrometry analysis.

A panel of ald-tagged rHSA carrier proteins was generated, with differently ald-tagged rHSA carrier proteins having aldehydes placed strategically throughout the scaffold. The panel thus serves as a library of differently ald-tagged rHSAs, where the members of the library differ in the number and/or position of ald tags in the scaffold. For example, as exemplified in FIG. 1B, one simple panel was generated where the members include an ald-tagged rHSA having an ald-tag position at the N-terminus, an ald-tagged rHSA having an ald-tag position at the C-terminus, an ald-tagged rHSA having an ald-tag positioned within a loop of the protein. Another library includes these members, as well as ald-tagged rHSAs having ald tags at both the N- and C-termini, at the N-termini and a solvent-accessible loop, at the C-termini and a solvent-accessible loop, and at each of the N-termini, the C-termini and a solvent-accessible loop. FIG. 10 provides the three-dimensional structure of HSA, which can be used for guidance in selecting sites for ald-tag insertion. Exemplary carrier protein-drug conjugates of HSA having a peptide drug positioned at exemplary solvent-accessible sites on HSA are provided in the bottom portion of FIG. 10.

Example 3

Conjugation of Peptides to the Protein Scaffold

Short serum half-life has been a challenge in the development peptide therapeutics. Peptides are typically cleared from the bloodstream within minutes to hours after administration, and thus may not be sufficiently exposed in the target tissue for a desired clinical effect. Aldehyde tagged carrier proteins, such as ald tagged HSA can be used as a carrier protein to increase the serum half-life of the peptides.

Two carrier protein-drug conjugates are generated—one a conjugate with Calcitonin and one a conjugate with GLP-1. As mentioned previously, by coupling the peptides to the HSA carrier protein the absorption and elimination half-lives will be increased.

The peptides were synthesized via standard Fmoc-based solid phase peptide synthesis protocols. The final residue added at the N terminus was (t-Boc-aminooxy)acetic acid followed by cleavage under standard conditions. Deprotection to expose the amino-oxy functionality is followed by HPLC purification. Purified ald-tagged HSA is added to a buffered solution of peptide that has been functionalized with an N-terminus amino-oxy functionality. Upon coupling to the ald-tagged HSA, the final protein-peptide complex is purified using FPLC.

Example 4

Assessment of HSA-GLP-1 Conjugates

The HSA-GLP-1 conjugate is assayed for activity as compared to native GLP-1. GLP-1, released from intestinal L-cells, is known for its potent stimulation of insulin biosynthesis and release from pancreatic β-cells. For the identification of GLP-1 receptor agonist, a cellular receptor activation assay based on the formation of cAMP occurring due to receptor activation is used. Receptor activation studies are performed by incubating RINm5F cells, a rat insulinoma cell line, with or without the test peptides or the HSA-peptide conjugates at increasing concentrations. Activation of the GLP-1 receptor is measured by quantification of the intracellular cAMP after cell lysis. EC$_{50}$ values (concentration of test compound leading to a half maximal stimulation of camp production) are calculated from the resulting dose response curves.

Example 5

Assessment of HSA-Calcitonin Conjugates

The HSA-Calcitonin conjugate is assayed for osteoclast activity as compared to native Calcitonin. The BD BioCoat Osteologic Bone Cell Culture System is used to assess the effect of treatment with the HSA-peptide conjugate and the native Calcitonin peptide on bone resorption of calcium. The BD BioCoat Osteologic Bone Cell Culture System involves sub-micron synthetic calcium phosphate thin films coated onto various culture vessels. This system has been used as an alternative method for compound screening for direct assessment of osteoclast and osteoblast activity in vitro. The thin film design permits easy and reliable quantification of results.

Example 6

Construction of Aldehyde Tagged Human Serum Albumin Carrier Proteins

The following describes production of an exemplary ald-tagged HSA.

A. Primer Design:

A nucleic acid encoding the wildtype HSA was inserted into a vector which can be exploited for as a template for subcloning. Using a vector with the appropriate internal restriction sites the first PCR product was:

-xmaI-----HSA-stop_codon-----xhoI-

After insertion of this sequence in a vector, variants were made using longer primers such as:

-xmaI------HSA-6xhis-stop_codon-----xhoI-
-xmaI------HSA-LCTPSR-stop_codon-----xhoI The following primers were used for PCR cDNA amplification.

```
Forward:
                                      (SEQ ID NO: 98)
5'-AATCCCGGGATGAAGTGGGTAACCTTTATTTCCC-3'

Reverse:
                                      (SEQ ID NO: 99)
5'-TGACTCGAGTTATAAGCCTAAGGCAGCTTGACTTG-3'
```

The double underline represents the native sequence, with the single underline the newly introduced restriction sites for further cloning.

A 1830 bp fragment was isolated after gel purification. This was followed by digestion with XmaI and XhoI, and the DNA fragment inserted in the expression vector. The open reading frame for HSA in the expression vector was as follows.

HSA-Encoding Nucleic Acid Sequence:

```
                                     (SEQ ID NO: 100)
aatcccgggatgaagtgggtaacctttatttcccttcttttttctctt tagctcggcttattccaggggtgtgatcgtcgagatgcacacaagag tgaggttgctcatcggataaagatttgggagaagaaaatttcaaagc caggtgttgattgcctttgctcagtatcttcagcagtgtccatttga agatcatgtaaaattagtgaatgaagtaactgaatttgcaaaaacat gtgttgctgatgagtcagctgaaaattgtgacaaatcacttcatacc cttttggagacaaattatgcacagttgcaactcttcgtgaaaccta tggtgaaatggctgactgctgtgcaaaacaagaacctgagagaaatg aatgcttcttgcaacacaaagatgacaacccaaacctcccccgattg gtgagaccagaggttgatgtgatgtgcactgatttcatgacaatgaa gagacatattgaaaaaatacttatatgaaattgccagaagacatcct tactttatgccccggaactccttttcttttgctaaaaggtataaagc tgcttttacagaatgttgccaagctgctgataaagctgcctgcctga gccaaagctcgatgaacttcgggatgaagggaaggcttcgtctgcca aacagagactcaagtgtgccagtctccaaaaatttggagaaagagct ttcaaagcatgggcagtagctcgcctgagccagagatttcccaaagc tgagtttgcagaagtttccaagttagtgacagatcttaccaaagtcc acacggaatgctgccatggagatctgcttgaatgtgctgatgacagg gcggaccagccaagtatatctgtgaaaatcaagattcgatctccagt aaactgaaggaatgctgtgaaaaacctctgttggaaaaatcccactg cattgccgaagtggaaaatgatgagatgcctgctgacttgccttcat tagctgctgattttgttgaaagtaaggatgtttgcaaaaactatgct gaggcaaaggatgtcttcctgggcatgttttttgtatgaatatgcaag aaggcatcctgattactctgtcgtgctgctgctgagacttgccaaga catatgaaaccactctagagaagtgctgtgccgctgcagatcctcat gaatgctatgccaaagtgacgatgaatttaaacctcttgtggaagag cctcagaatttaatcaaacaaaattgtgagctattgagcagcttgga gagtacaaattccagaatgcgctattagttcgttacaccaagaaagt accccaagtgtcaactccaactcagtagaggtctcaagaaacctagg aaaagtgggcagcaaatgagtaaacatcctgaagcaaaaagaatgcc ctgtgcagaagactatctatccgtggtcctgaaccagttatgtgtga gcatgagaaaacgccagtaagtgacagagtcaccaaatgctgcacag aatccttggtgaacaggcgaccatgcttttcagctctggaagtcgat gaaacatacgttcccaaagagtttaatgctgaaacattcaccaccat gcagatatatgcacactactgagaaggagagacaaatcaagaaacaa actgcacttgttgagctcgtgaaacacaagcccaaggcaacaaaaga gcaactgaaagctgttatggatgatttcgcagcttttgtagagaagt gctgcaaggctgacgataaggagacctgctttgccgaggagggtaaa aaacttgttgctgcaagtcaagctgccttaggcttaactcgag
```

Amino Acid Sequence of Encoded HSA

The HSA native leader sequence (single and double underlined residues) is removed in 2-step process (in humans) before secretion of mature protein:

```
                                        (SEQ ID NO: 101)
NPGMKWVTFI SLLFLFSSAY SRGVFRRDAH KSEVAHRFKD

LGEENFKALV LIAFAQYLQQ CPFEDHVKLV NEVTEFAKTC

VADESAENCD KSLHTLFGDK LCTVATLRET YGEMADCCAK

QEPERNECFL QHKDDNPNLP RLVRPEVDVM CTAFHDNEET

FLKKYLYEIA RRHPYFYAPE LLFFAKRYKA AFTECCQAAD

KAACLLPKLD ELRDEGKASS AKQRLKCASL QKFGERAFKA

WAVARLSQRF PKAEFAEVSK LVTDLTKVHT ECCHGDLLEC

ADDRADLAKY ICENQDSISS KLKECCEKPL LEKSHCIAEV

ENDEMPADLP SLAADFVESK DVCKNYAEAK DVFLGMFLYE

YARRHPDYSV VLLLRLAKTY ETTLEKCCAA ADPHECYAKV

FDEFKPLVEE PQNLIKQNCE LFEQLGEYKF QNALLVRYTK

KVPQVSTPTL VEVSRNLGKV GSKCCKHPEA KRMPCAEDYL
```

SVVLNQLCVL HEKTPVSDRV TKCCTESLVN RRPCFSALEV

DETYVPKEFN AETFTFHADI CTLSEKERQI KKQTALVELV

KHKPKATKEQ LKAVMDDFAA FVEKCCKADD KETCFAEEGK

KLVAASQAAL GLTR

B. Construction of C-terminal Modified HSA

Using the plasmid with native HSA as a PCR template a new 3' HSA PCR primer with additional restriction sites for appending C-terminal tags onto recombinant HSA was designed as follows:

(SEQ ID NO: 102)
5'-ATA<u>CTCGAG</u>TTA<u>GTCGAC</u>TTC<u>AAGCTT</u><u><u>TAAGCCTAAGGCAGCTTG</u></u><u><u>ACTTG</u></u>-3'

Double underline: native C-terminus of HSA sequence.
Single underline adjacent double underline: HinDIII site
Bold residues=Stop codon
Single underline 3' of stop codon: SalI site
Single underline 5' of stop codon: XhoI site The SalI and HindIII were provided in the primer as these are not in the plasmid constructs. Used in conjunction with the same Forward primer used for original HSA amplification from cDNA, an 1863 residue PCR product was obtained as follows (with the predicted amino sequence following):

(SEQ ID NO: 103)
```
aatcccgggatgaagtgggtaaccatataccct tctattctctttagctcggcttattccagggg
tgtgatcgtcgagatgcacacaagagtgaggagctcatcggtttaaagataggagaagaaaatt
tcaaagccaggtgagattgcctttgctcagtatcttcagcagtgtccatttgaagatcatgtaaa
attagtgaatgaagtaactgaatttgcaaaaacatgtgttgctgatgagtcagctgaaaattgtg
acaaatcacttcatacccta ttggagacaaattatgcacagagcaactcttcgtgaaacctatgg
tgaaatggctgactgctgtgcaaaacaagaacctgagagaaatgaatgcacttgcaacacaaaga
tgacaacccaaacct cccccgattggtgagaccagaggttgatgtgatgcactgcattcatga
caatgaagagacatttagaaaaaatacttatatgaaattgccagaagacatcct tactatatgcc
ccggaactccat tattgctaaaaggtataaagctgctatacagaatgagccaagctgctgataaa
gctgcctgcctgagccaaagctcgatgaacttcgggatgaagggaaggcttcgtctgccaaacag
agactcaagtgtgccagtctccaaaaatttggagaaagagctttcaaagcatgggcagtagctcg
cctgagccagagatttcccaaagctgagtttgcagaagtaccaagttagtgacagatcttaccaa
agtccacacggaatgctgccatggagatctgct tgaatgtgctgatgacagggcggaccagccaa
gtatatctgtgaaaatcaagattcgatctccagtaaactgaaggaatgctgtgaaaaacctctgt
tggaaaaatcccactgcattgccgaagtggaaaatgatgagatgcctgctgacttgccttcatta
gctgctgattagttgaaagtaaggatgatgcaaaaactatgctgaggcaaaggatgtcttcctgg
gcatgatagtatgaatatgcaagaaggcatcctgattactctgtcgtgctgctgctgagacttgc
caagacatatgaaaccactctagagaagtgctgtgccgctgcagatcctcatgaatgctatgcca
aagtgacgatgaatttaaacctcagtggaagagcctcagaatttaatcaaacaaaattgtgagct
attgagcagcaggagagtacaaattccagaatgcgctattagttcgttacaccaagaaagtaccc
caagtgtcaactccaactcagtagaggtctcaagaaacctaggaaaagtgggcagcaaatgagta
aacatcctgaagcaaaagaatgccctgtgcagaagactatctatccgtggtcctgaaccagtta
tgtgtgagcatgagaaaacgccagtaagtgacagagtcaccaaatgctgcacagaatccaggtga
acaggcgaccatgctatcagctctggaagtcgatgaaacatacgacccaaagagataatgctgaa
acattcaccaccatgcagatatatgcacactactgagaaggagagacaaatcaagaaacaaactg
cacttgttgagctcgtgaaacacaagcccaaggcaacaaaagagcaactgaaagctgttatggat
gatttcgcagcttttgtagagaagtgctgcaaggctgacgataaggagacctgctagccgaggag
ggtaaaaaacttgagctgcaagtcaagctgccttaggcttaaagcttgaagtcgactaactcgag
ata
```

(SEQ ID NO: 104)
```
NPGMKWVTFI SLLFLFSSAY SRGVFRRDAH KSEVAHRFKD LGEENFKALV LIAFAQYLQQ

CPFEDHVKLV NEVTEFAKTC VADESAENCD KSLHTLFGDK LCTVATLRET YGEMADCCAK

QEPERNECFL QHKDDNPNLP RLVRPEVDVM CTAFHDNEET FLKKYLYEIA RRHPYFYAPE

LLFFAKRYKA AFTECCQAAD KAACLLPKLD ELRDEGKASS AKQRLKCASL QKFGERAFKA

WAVARLSQRF PKAEFAEVSK LVTDLTKVHT ECCHGDLLEC ADDRADLAKY ICENQDSISS

KLKECCEKPL LEKSHCIAEV ENDEMPADLP SLAADFVESK DVCKNYAEAK DVFLGMFLYE

YARRHPDYSV VLLLRLAKTY ETTLEKCCAA ADPHECYAKV FDEFKPLVEE PQNLIKQNCE

LFEQLGEYKF QNALLVRYTK KVPQVSTPTL VEVSRNLGKV GSKCCKHPEA KRMPCAEDYL

SVVLNQLCVL HEKTPVSDRV TKCCTESLVN RRPCFSALEV DETYVPKEFN AETFTFHADI

CTLSEKERQI KKQTALVELV KHKPKATKEQ LKAVMDDFAA FVEKCCKADD KETCFAEEGK

KLVAASQAAL GLKLEVDLEI
```

The product was digested with XmaI and XhoI and inserted into the expression vector, then digested with HinDIII and SalI (sequentially) for insertion of a synthetic piece of double-stranded DNA with complementary sticky ends.

The sequence of the synthetic DNA encoding the HSA having an ald tag LCTPSR (SEQ ID NO:1) at the C terminus is provided below (with the predicted amino sequence following):

(SEQ ID NO: 105)
```
aacccgggcatgaaatgggtgacctttattagcctgctgtttctgtttagcagcgcgtatagccg cggcgtgtttcgccgcgatgcgcataaaagcgaagtggcgcatcgctttaaagatctgggcgaag aaaactttaaagcgctggtgctgattgcgtttgcgcagtatctgcagcagtgcccgatgaagatc atgtgaaactggtgaacgaagtgaccgaatttgcgaaaacctgcgtggcggatgaaagcgcggaa aactgcgataaaagcctgcataccctgtaggcgataaactgtgcaccgtggcgaccctgcgcgaa acctatggcgaaatggcggattgctgcgcgaaacaggaaccggaacgcaacgaatgctactgcag cataaagatgataacccgaacctgcgcgcgcctggtgcgcccggaagtggatgtgatgtgcaccgc gatcatgataacgaagaaacctactgaaaaaatatctgtatgaaattgcgcgccgccatccgtat tatatgcgccggaactgctgttttttgcgaaacgctataaagcggcgtttaccgaatgctgccag gcggcggataaagcggcgtgcctgctgccgaaactggatgaactgcgcgatgaaggcaaagcgag cagcgcgaaacagcgcctgaaatgcgcgagcctgcagaaatttggcgaacgcgcgtttaaagcgt gggcggtggcgcgcctgagccagcgctttccgaaagcggaatttgcggaagtgagcaaactggtg accgatctgaccaaagtgcataccgaatgctgccatggcgatctgctggaatgcgcggatgatcg cgcggatctggcgaaatatatttgcgaaaaccaggatagcattagcagcaaactgaaagaatgct gcgaaaaaccgctgctggaaaaaagccattgcattgcggaagtggaaaacgatgaaatgccggcg gatctgccgagcctggcggcggattttgtggaaagcaaagatgtgtgcaaaaactatgcggaagc gaaagatgtgtttctgggcatgtttctgtatgaatatgcgcgccgccatccggattatagcgtgg tgctgctgctgcgcctggcgaaaacctatgaaaccaccctggaaaaatgctgcgcggcggcggat ccgcatgaatgctatgcgaaagtgatgatgaatttaaaccgctggtggaagaaccgcagaacctg attaaacagaactgcgaactgatgaacagctgggcgaatataaatttcagaacgcgctgctggtg cgctataccaaaaaagtgccgcaggtgagcaccccgaccctggtggaagtgagccgcaacctggg caaagtgggcagcaaatgctgcaaacatccggaagcgaaacgcatgccgtgcgcggaagattatc tgagcgtggtgctgaaccagctgtgcgtgctgcatgaaaaaaccccggtgagcgatcgcgtgacc aaatgctgcaccgaaagcctggtgaaccgcgcccgtgctttagcgcgctggaagtggatgaaac ctatgtgccgaaagaatttaacgcggaaacctttacctttcatgcggatatttgcaccctgagcg
```

```
aaaaagaacgccagattaaaaaacagaccgcgctggtggaactggtgaaacataaaccgaaagcg accaaagaacagctgaaagcggtgatggatgattagcggcgtagtggaaaaatgctgcaaagcgg atgataaagaaacctgctttgcggaagaaggcaaaaaactgctgtgcaccccgagccgcgtggat ctggaaatt
```

(SEQ ID NO: 106)
NPG<u>MKWVTFI SLLFLFSSAY SRGVFRR</u>DAH KSEVAHRFKD LGEENFKALV LIAFAQYLQQ

CPFEDHVKLV NEVTEFAKTC VADESAENCD KSLHTLFGDK LCTVATLRET YGEMADCCAK

QEPERNECFL QHKDDNPNLP RLVRPEVDVM CTAFHDNEET FLKKYLYEIA RRHPYFYAPE

LLFFAKRYKA AFTECCQAAD KAACLLPKLD ELRDEGKASS AKQRLKCASL QKFGERAFKA

WAVARLSQRF PKAEFAEVSK LVTDLTKVHT ECCHGDLLEC ADDRADLAKY ICENQDSISS

KLKECCEKPL LEKSHCIAEV ENDEMPADLP SLAADFVESK DVCKNYAEAK DVFLGMFLYE

YARRHPDYSV VLLLRLAKTY ETTLEKCCAA ADPHECYAKV FDEFKPLVEE PQNLIKQNCE

LFEQLGEYKF QNALLVRYTK KVPQVSTPTL VEVSRNLGKV GSKCCKHPEA KRMPCAEDYL

SVVLNQLCVL HEKTPVSDRV TKCCTESLVN RRPCFSALEV DETYVPKEFN AETFTFHADI

CTLSEKERQI KKQTALVELV KHKPKATKEQ LKAVMDDFAA FVEKCCKADD KETCFAEEGK

KLL<u>CTPSR</u>VD LEI

The plasmid encoding recombinant HSA was further modified to include the FGE motif at the C-terminus. Primers, designed for the insertion of FGE motif and thrombin-cleavable affinity tag at C-terminus, were ligated into the vector using standard molecular biology techniques. The insert design was as follows:

(SEQ ID NO:: 107)
HinDIII-LCTPSR-LVPRGS-PstI-HHHHHH-SalI (SEQ ID NO: 108)
5' AGCTTCTTTGTACCCCTAGCAGGCTGGTGCCGCGCGGCAGCCTGCAG

CATCATCACCACCATCACG (SEQ ID NO: 109)
5' AGAAACATGGGGATCGTCCGACCACGGCGCGCCGTCGGACGTCGTAG

TAGTGGTGGTAGTGCAGCT

PstI site allows for detection of insert via diagnostic digestion instead of sequencing each miniprep. LVPRGS is a thrombin cleavage site. The ORF translates to:

(SEQ ID NO: 110)
MKWTFISLLF LFSSAYSRGV FRRDAHKSEV AHRFKDLGEE

NFKALVLIAF AQYLQQCPFE DHVKLVNEVT EFAKTCVADE

SAENCDKSLH TLFGDKLCTVA TLRETYGEMA DCCAKQEPER

NECFLQHKDD NPNLPRLVRP EVDVMCTAFH DNEETFLKKY

LYEIARRHPY FYAPELLFFAK RYKAAFTECC QAADKAACLLP

KLDELRDEGK ASSAKQRLKCA SLQKFGERA FKAWAVARLSQ

RFPKAEFAEV SKLVTDLTKV HTECCHGDLL ECADDRADLA

KYICENQDSI SSKLKECCEK PLLEKSHCIA EVENDEMPAD

LPSLAADFVE SKDVCKNYAE AKDVFLGMFL YEYARRHPDY

SVVLLLRLAK TYETTLEKCC AAADPHECYAK VFDEFKPLVE

EPQNLIKQNCE LFEQLGEYKFQ NALLVRYTKK VPQVSTPTLV

EVSRNLGKVG SKCCKHPEAK RMPCAEDYLS VVLNQLCVLH

EKTPVSDRVT KCCTESLVNR RPCFSALEVD ETYVPKEFNA

ETFTFHADIC TLSEKERQIK KQTALVELVK HKPKATKEQL

KAVMDDFAAF VEKCCKADDK ETCFAEEGKK LVAASQAALG

LKL<u>LCTPSR</u>LV P<u>RGSLQ</u>HHHH HHVD

Figure 13:
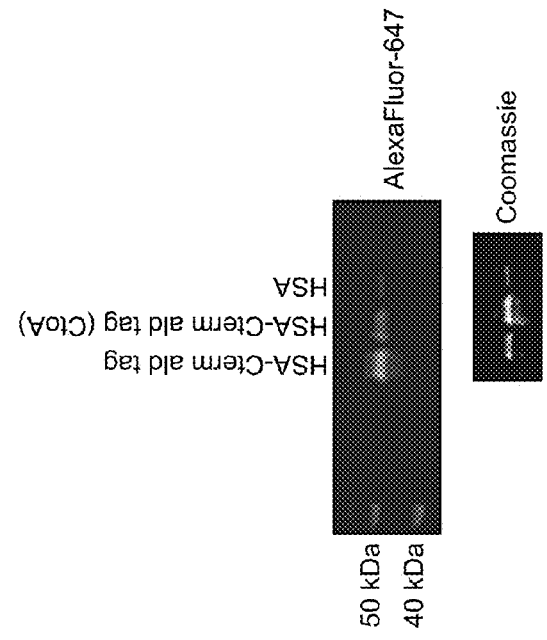
FIG. 13 is a picture of a protein gel illustrating HSA, purified using Ni/NTA, purified using Ni/NTA, containing an aldehyde tag at the C terminus conjugated with a fluorophore. The negative control, CtoA construct, does not get converted to a formylglycine and is subsequently not conjugated when reacted with the fluorophore.

The construct was expressed in *S. cerevisae* and purified using affinity column purification (FIG. 13). The modified protein was reacted with purified FGE to convert the cysteine to formyl glycine. The recombinant HSA was reacted with a fluorophore containing a hydrazide and the conversion and conjugation was quantified by measuring the resulting fluorescence of the modified protein (FIG. 13).

C. Construction of N-terminal Modified HSA

Generating the N-terminal aldehyde tagged HSA was accomplished by inserting an in-frame synthetic gene where the N-terminus of mature HSA was modified with the aldehyde tag. The synthetic gene was cloned into a yeast expression vector using standard molecular biology techniques. The designed sequence is as follows. Bold/underline=restriction site arrays aaacgatg = kozak (shine dalgarno) sequence aagtgggtaacctttatttcccttctattctctttagctcggcttattccaggggtgtgtttcgtcga (SEQ ID NO: 11) = prepro region (removed from mature protein)

caccatcatcaccaccatcac (SEQ ID NO: 112) = 7xHIS tag ctggtgccgcgcggcagc (SEQ ID NO: 113) = thrombin recognition site ctttgtacccctagcagg (SEQ ID NO: 114) = LCTPSR motif (SEQ ID NO: 1)

ggaggc = diglycine linker taa = stop codon (SEQ ID NO: 115)
aaataaagcttcccgggggatccaaacgatgaagtgggtaacctttatttcccttcttttttctcttta
gctcggcttattccaggggtgtgtttcgtcgagatgcacacaagcaccatcatcaccaccatcacctg
gtgccgcgcggcagcctttgtaccctagcaggggaggcagtgaggttgctcatcggtttaaagattt
gggagaagaaaatttcaaagccttggtgttgattgcctttgctcagtatcttcagcagtgtccatttg
aagatcatgtaaaattagtgaatgaagtaactgaatttgcaaaaacatgtgttgctgatgagtcagct
gaaaattgtgacaaatcacttcatacccttttttggagacaaattatgcacagttgcaactcttcgtga
aacctatggtgaaatggctgactgctgtgcaaaacaagaacctgagagaaatgaatgcttcttgcaac
acaaagatgacaacccaaacctcccccgattggtgagaccagaggttgatgtgatgtgcactgcttttt
catgacaatgaagagacattttttgaaaaaatacttatatgaaattgccagaagacatccttacttttta
tgcccccggaactccttttctttgctaaaaggtataaagctgcttttacagaatgttgccaagctgctg
ataaagctgcctgcctgagccaaagctcgatgaacttcgggatgaagggaaggcttcgtctgccaaac
agagactcaagtgtgccagtctccaaaaatttggagaaagagctttcaaagcatgggcagtagctcgc
ctgagccagagatttcccaaagctgagtttgcagaagtttccaagttagtgacagaccttaccaaagt
ccacacggaatgctgccatggagacctgcttgaatgtgctgatgacagggcggaccttgccaagtata
tctgtgaaaatcaagattcgatctccagtaaactgaaggaatgctgtgaaaaacctctgttggaaaaa
tcccactgcattgccgaagtggaaaatgatgagatgcctgctgacttgccttcattagctgctgattt
tgttgaaagtaaggatgtttgcaaaaactatgctgaggcaaaggatgtcttcctgggcatgttttttgt
atgaatatgcaagaaggcatcctgattactctgtcgtgctgctgctgagacttgccaagacatatgaa
accactctagagaagtgctgtgccgctgcagatcctcatgaatgctatgccaaagtgttcgatgaatt
taaacctcttgtggaagagcctcagaatttaatcaaacaaaattgtgagcttttgagcagcttggag
agtacaaattccagaatgcgctattagttcgttacaccaagaaagtaccccaagtgtcaactccaact
cttgtagaggtctcaagaaacctaggaaaagtgggcagcaaatgttgtaaacatcctgaagcaaaaag
aatgccctgtgcagaagactatctatccgtggtcctgaaccagttatgtgtgttgcatgagaaaacgc
cagtaagtgacagagtcaccaaatgctgcacagaatccttggtgaacaggcgaccatgcttttcagct
ctggaagtcgatgaaacatacgttcccaaagagtttaatgctgaaacattcaccttccatgcagatat
atgcacactttctgagaaggagagacaaatcaagaaacaaactgcacttgttgagctcgtgaaacaca
agcccaaggcaacaaaagagcaactgaaagctgttatggatgatttcgcagcttttgtagagaagtgc
tgcaaggctgacgataaggagacctgctttgccgaggagggtaaaaaacttgttgctgcaagtcaagc
tgccttaggcttataatgaattcgtcgacctcgaggatatcacaag The expected ORF product was (SEQ ID NO: 116)
```
MKWVTFISLL FLFSSAYSRG VFRRDAHKHH HHHHHLVPRG
SLCTPSRGGS EVAHRFKDLG EENFKALVLI AFAQYLQQCP
FEDHVKLVNE VTEFAKTCVA DESAENCDKS LHTLFGDKLC
TVATLRETYG EMADCCAKQE PERNECFLQH KDDNPNLPRL
VRPEVDVMCT AFHDNEETFL KKYLYEIARR HPYFYAPELL
FFAKRYKAAF TECCQAADKA ACLLPKLDEL RDEGKASSAK
QRLKCASLQK FGERAFKAWA VARLSQRFPKA EFAEVSKLVT
DLTKVHTECC HGDLLECADDRADLAKYICE NQDSISSKLK
ECCEKPLLEK SHCIAEVEND EMPADLPSLA ADFVESKDVC
KNYAEAKDVF LGMFLYEYAR RHPDYSVVLL LRLAKTYETT
LEKCCAAADP HECYAKVFDE FKPLVEEPQN LIKQNCELFE
QLGEYKFQNA LLVRYTKKVP QVSTPTLVEV SRNLGKVGSK
CCKHPEAKRM PCAEDYLSVV LNQLCVLHEK TPVSDRVTKC
CTESLVNRRP CFSALEVDET YVPKEFNAET FTFHADICTL
SEKERQIKKQ TALVELVKHK PKATKEQLKA VMDDFAAFVE
KCCKADDKET CFAEEGKKLV AASQAALGL
```

The construct was expressed in *S. cerevisae* and purified using affinity column purification. The modified protein was reacted with purified FGE to convert the cysteine to formylglycine. The recombinant HSA was reacted with a fluorophore containing a hydrazide and the conversion and conjugation was quantified by measuring the resulting fluorescence of the modified protein.

D. Construction of Internal Modified HSA

Generating the internal aldehyde tagged HSA was accomplished by inserting an in-frame synthetic gene where key restriction sites are placed where mature HSA is to be modified with the aldehyde tag. The synthetic gene was cloned into a yeast expression vector using standard molecular biology techniques. The designed sequence was as follows:

(SEQ ID NO: 117)
```
CGAAGGATCCAAACGATGAAGTGGGTAACCTTTATTTCCCTTCTTTTTC
TCTTTAGCTCGGCTTATTCCAGGGGTGTGTTTCGTCGAGATGCACACAA
GAGTGAGGTTGCTCATCGGTTTAAAGATTTGGGAGAAGAAAATTTCAA
GCCTTGGTGTTGATTGCCTTTGCTCAGTATCTTCAGCAGTGTCCATTTG
AAGATCATGTAAAATTAGTGAATGAAGTAACTGAATTTGCAAAAACATG
TGTTGCTGATGAGTCAGCTGAAAATTGTGACAAATCACTTCATACCCTT
TTTGGAGACAAATTATGCACAGTTGCAACTCTTCGTGAAACCTATGGTG
AAATGGCTGACTGCTGTGCAAAACAAGAACCTGAGAGAAATGAATGCTT
CTTGCAACACAAAGATGACAACCCAAACCTCCCCCGATTGGTGAGACCA
GAGGTTGATGTGATGTGCACTGCTTTTCATGACAATGAAGAGACATTTT
TGAAAAAATACTTATATGAAATTGCCAGAAGACATCCTTACTTTTATGC
CCCGGAACTCCTTTTCTTTGCTAAAAGGTATAAAGCTGCTTTTACAGAA
TGTTGCCAAGCTGCTGATAAAGCTGCCTGCCTGTTGCCAAAGCTCGATG
AACTTCGGGATGAAGGGAAGGCTTCGTCTGCCAAACAGAGACTCAAGTG
TGCCAGTCTCCAAAAATTTGGAGAAAGAGCTTTCAAAGCATGGGCAGTA
GCTCGCCTGAGCCAGAGATTTCCCAAGGCTGAGTTTGCAGAAGTTTCCA
AGTTAGTGACTGACCTTACCAAAGTCCACACGGAATGCTGTCACGGAGA
CCTGCTTGAATGTGCTGATGACAGGGCGGACCTTGCCAAGTATATCTGT
GAAAATCAAGATTCGATCTCCAGTAAACTGAAGGAATGCTGTGAAAAAC
CTCTGTTGGAAAAATCCCACTGCATTGCCGAAGTGGAAAATGATGAGAT
GCCTGCTCTCGAGCCTTCTACTAGTGCTGATTTTGTTGAAAGTAAGGAT
GTTTGCAAAAACTATGCTGAGGCAAAGGATGTCTTCCTGGGCATGTTTT
TGTATGAATATGCAAGAAGGCATCCTGATTACTCTGTCGTGCTGCTGCT
GAGACTTGCCAAGACATATGAAACCACACTTGAGAAGTGCTGTGCCGCC
GCTGATCCTCATGAATGCTATGCCAAAGTGTTCGATGAATTTAAACCTC
TTGTGGAAGAGCCTCAGAATTTAATCAAACAAAATTGTGAGCTTTTTGA
GCAGCTTGGAGAGTACAAATTCCAGAATGCGCTATTAGTTCGTTACACC
AAGAAAGTACCCCAAGTGTCAACTCCAACTCTTGTAGAGGTCTCAAGAA
ACCTAGGAAAAGTGGGCAGCAAATGTTGTAAACATCCTGAAGCAAAAAG
AATGCCCTGTGCAGAAGACTATCTATCCGTGGTCCTGAACCAGTTATGT
GTGTTGCATGAGAAAACGCCAGTAAGTGACAGAGTCACCAAATGCTGCA
CAGAATCCTTGGTGAACAGGCGACCATGCTTTTCAGCTCTGGAAGTCGA
TGAAACATACGTTCCCAAAGAGTTTAATGCTGAAACATTCACCTTCCAT
GCAGATATATGCACACTTTCTGAGAAGGAGAGACAAATCAAGAAACAAA
CTGCACTTGTTGAGCTTGTGAAACACAAGCCCAAGGCAACAAAAGAGCA
ACTGAAAGCTGTTATGGATGATTTCGCAGCTTTTGTAGAGAAGTGCTGC
AAGGCTGACGATAAGGAGACCTGCTTTGCCGAGGAGGGTAAAAAACTTG
TTGCTGCAAGTCAAGCTGCCTTAGGCTTACCCGGGTCTACTCCGCGGCT
GGTGCCGCGCGGCAGCCTTCAACATCATCACCACCATCACGTCGACTAA
TGGAATTCCCTA
```

The expected ORF was:

(SEQ ID NO: 118)
```
MKWVTFISLL FLFSSAYSRG VFRRDAHKSE VAHRFKDLGE
ENFKALVLIA FAQYLQQCPF EDHVKLVNEV TEFAKTCVAD
ESAENCDKSL HTLFGDKLCT VATLRETYGE MADCCAKQEP
ERNECFLQHK DDNPNLPRLV RPEVDVMCTA FHDNEETFLK
KYLYEIARRH PYFYAPELLF FAKRYKAAFT ECCQAADKAA
CLLPKLDELR DEGKASSAKQ RLKCASLQKF GERAFKAWAV
ARLSQRFPKA EFAEVSKLVT DLTKVHTECC HGDLLECADD
RADLAKYICE NQDSISSKLK ECCEKPLLEK SHCIAEVEND
EMPALEPSTS ADFVESKDVC KNYAEAKDVF LGMFLYEYAR
RHPDYSVVLL LRLAKTYETTL EKCCAAADPH ECYAKVFDEF
```

```
KPLVEEPQNL IKQNCELFEQ LGEYKFQNAL LVRYTKKVPQ

VSTPTLVEVS RNLGKVGSKC CKHPEAKRMP CAEDYLSVVL

NQLCVLHEKT PVSDRVTKCC TESLVNRRPC FSALEVDETY

VPKEFNAETF TFHADICTLS EKERQIKKQT ALVELVKHKP

KATKEQLKAV MDDFAAFVEK CCKADDKETC FAEEGKKLVA

ASQAALGLPG STPRLVPRGS LQHHHHHHVD
```

6×His-HSA synthetic gene was ligated into pCR blunt II-TOPO vector, followed by digestion of pRW33 with EcoRI and BamHI to cut out 6×His-HSA, which was purified and then ligated into pcDNA3.1 using the EcoRI and BamHI sites. The resulting vector was Digested with XhoI/SpeI and the annealed primers:

```
                                    (SEQ ID NO: 119)
5'-CTAGCCTTTGTACCCCTAGCAGGG-3'
and
                                    (SEQ ID NO: 120)
5-CTAGCCCTGCTAGGGGTACAAAGA-3'
``` were ligated in generating the aldehyde tag. The designed sequence was as follows:

```
                                                  (SEQ ID NO: 121)
CCGGAACTCCTTTTCTTTGCTAAAAGGTATAAAGCTGCTTTTACAGAAT

GTTGCCAAGCTGCTGATAAAGCTGCCTGCCTGTTGCCAAAGCTCGATGA

ACTTCGGGATGAAGGGAAGGCTTCGTCTGCCAAACAGAGACTCAAGTGT

GCCAGTCTCCAAAAATTTGGAGAAAGAGCTTTCAAAGCATGGGCAGTAG

CTCGCCTGAGCCAGAGATTTCCCAAGGCTGAGTTTGCAGAAGTTTCCAA

GTTAGTGACTGACCTTACCAAAGTCCACACGGAATGCTGTCACGGAGAC

CTGCTTGAATGTGCTGATGACAGGGCGGACCTTGCCAAGTATATCTGTG

AAAATCAAGATTCGATCTCCAGTAAACTGAAGGAATGCTGTGAAAAACC

TCTGTTGGAAAAATCCCACTGCATTGCCGAAGTGGAAAATGATGAGATG

CCTGCTCTCGATCTTTGTACCCCTAGCAGGGCTACTAGTGCTGATTTTG

TTGAAAGTAAGGATGTTTGCAAAAACTATGCTGAGGCAAAGGATGTCTT

CCTGGGCATGTTTTTGTATGAATATGCAAGAAGGCATCCTGATTACTCT

GTCGTGCTGCTGCTGAGACTTGCCAAGACATATGAAACCACACTTGAGA

AGTGCTGTGCCGCCGCTGATCCTCATGAATGCTATGCCAAAGTGTTCGA

TGAATTTAAACCTCTTGTGGAAGAGCCTCAGAATTTAATCAAACAAAAT

TGTGAGCTTTTTGAGCAGCTTGGAGAGTACAAATTCCAGAATGCGCTAT

TAGTTCGTTACACCAAGAAAGTACCCCAAGTGTCAACTCCAACTCTTGT

AGAGGTCTCAAGAAACCTAGGAAAAGTGGGCAGCAAATGTTGTAAACAT

CCTGAAGCAAAAAGAATGCCCTGTGCAGAAGACTATCTATCCGTGGTCC

TGAACCAGTTATGTGTGTTGCATGAGAAAACGCCAGTAAGTGACAGAGT

CACCAAATGCTGCACAGAATCCTTGGTGAACAGGCGACCATGCTTTTCA

GCTCTGGAAGTCGATGAAACATACGTTCCCAAAGAGTTTAATGCTGAAA

CATTCACCTTCCATGCAGATATATGCACACTTTCTGAGAAGGAGAGACA

AATCAAGAAACAAACTGCACTTGTTGAGCTTGTGAAACACAAGCCCAAG

GCAACAAAAGAGCAACTGAAAGCTGTTATGGATGATTTCGCAGCTTTTG

TAGAGAAGTGCTGCAAGGCTGACGATAAGGAGACCTGCTTTGCCGAGGA

GGGTAAAAAACTTGTTGCTGCAAGTCAAGCTGCCTTAGGCTTACCCGGG

TCTACTCCGCGGCTGGTGCCGCGCGGCAGCCTTCAACATCATCACCACC

ATCACGTCGACTAATGGAATTCCCTA
```

The expected ORF product was:

```
                                                  (SEQ ID NO: 122)
MKWVTFISLL FLFSSAYSRG VFRRDAHKSE VAHRFKDLGE

ENFKALVLIA FAQYLQQCPF EDHVKLVNEV TEFAKTCVAD

ESAENCDKSL HTLFGDKLCT VATLRETYGE MADCCAKQEP

ERNECFLQHK DDNPNLPRLV RPEVDVMCTA FHDNEETFLK

KYLYEIARRH PYFYAPELLF FAKRYKAAFT ECCQAADKAA

CLLPKLDELR DEGKASSAKQ RLKCASLQKF GERAFKAWAV

ARLSQRFPKA EFAEVSKLVT DLTKVHTECC HGDLLECADD

RADLAKYICE NQDSISSKLK ECCEKPLLEK SHCIAEVEND

EMPALDLCTP SRATSADFVE SKDVCKNYAE AKDVFLGMFL

YEYARRHPDY SVVLLLRLAK TYETTLEKCC AAADPHECYA

KVFDEFKPLV EEPQNLIKQN CELFEQLGEY KFQNALLVRY

TKKVPQVSTP TLVEVSRNLG KVGSKCCKHP EAKRMPCAED

YLSVVLNQLC VLHEKTPVSD RVTKCCTESL VNRRPCFSAL

EVDETYVPKE FNAETFTFHA DICTLSEKER QIKKQTALVE

LVKHKPKATK EQLKAVMDDF AAFVEKCCKA DDKETCFAEE

GKKLVAASQA ALGLPGSTPR LVPRGSLQHH HHHVD
```

6×His-LCTPSR-HSA (HHHHHHLCTPSR (SEQ ID NO:127)) was expressed and purified from CHO cells. 6×His-LCTPSR-HSA (SEQ ID NO:127) was transfected in pcDNA3.1 into CHO cells in Opti-MEM serum-free medium using Lipofectin transfection reagent in a 10 cm dish. After 3 h at 37° C., the Opti-MEM medium was removed and added 10 mL of HAM'S F12 serum-free medium. After 3 days at 37°, the media was collected and added 10 mL Binding Buffer (20 mM Na2PO4, 500 mM NaCl, 20 mM Imidazole, pH 7.5) and 200 μl of Ni-NTA resin. After incubating with rotation for 1 h at 4° C., the mixture was applied to a column. The resin was washed with 5 mL Binding Buffer and then eluted with 5×500 μl Elution Buffer (20 mM Na2PO4, 500 mM NaCl, 500 mM Imidazole, pH 7.5). The samples were run on 10% Tric-HCl gels and either stained with Coomassie or transferred to nitrocellulose for immunoblotting with an anti-His antibody to verify the presence of protein.

E. Construction HSA Modified with Two Aldehyde Tags, Internally Modified and C-terminally Modified HSA The vectors containing recombinant HSA was digested with XmaI/SacII and the annealed primers 5'-CCGGACTTTGTACCCCTAGCAGGGGGC-3' (SEQ ID NO:123) and 5'-CCCCTGCTAGGGGTACAAAGT-3' (SEQ ID NO:124) were ligated in resulting in the insertion of the aldehyde tag. The designed sequence was as follows:

(SEQ ID NO: 125)
```
GAGACATTTTTGAAAAAATACTTATATGAAATTGCCAGAAGACATCCTT

ACTTTTATGCCCCGGAACTCCTTTTCTTTGCTAAAAGGTATAAAGCTGC

TTTTACAGAATGTTGCCAAGCTGCTGATAAAGCTGCCTGCCTGTTGCCA

AAGCTCGATGAACTTCGGGATGAAGGGAAGGCTTCGTCTGCCAAACAGA

GACTCAAGTGTGCCAGTCTCCAAAAATTTGGAGAAAGAGCTTTCAAAGC

ATGGGCAGTAGCTCGCCTGAGCCAGAGATTTCCCAAGGCTGAGTTTGCA

GAAGTTTCCAAGTTAGTGACTGACCTTACCAAAGTCCACACGGAATGCT

GTCACGGAGACCTGCTTGAATGTGCTGATGACAGGGCGGACCTTGCCAA

GTATATCTGTGAAAATCAAGATTCGATCTCCAGTAAACTGAAGGAATGC

TGTGAAAAACCTCTGTTGGAAAAATCCCACTGCATTGCCGAAGTGGAAA

ATGATGAGATGCCTGCTCTCGATCTTTGTACCCCTAGCAGGGCTACTAG

TGCTGATTTTGTTGAAAGTAAGGATGTTTGCAAAAACTATGCTGAGGCA

AAGGATGTCTTCCTGGGCATGTTTTTGTATGAATATGCAAGAAGGCATC

CTGATTACTCTGTCGTGCTGCTGCTGAGACTTGCCAAGACATATGAAAC

CACACTTGAGAAGTGCTGTGCCGCCGCTGATCCTCATGAATGCTATGCC

AAAGTGTTCGATGAATTTAAACCTCTTGTGGAAGAGCCTCAGAATTTAA

TCAAACAAAATTGTGAGCTTTTTGAGCAGCTTGGAGAGTACAAATTCCA

GAATGCGCTATTAGTTCGTTACACCAAGAAAGTACCCCAAGTGTCAACT

CCAACTCTTGTAGAGGTCTCAAGAAACCTAGGAAAAGTGGGCAGCAAAT

GTTGTAAACATCCTGAAGCAAAAGAATGCCCTGTGCAGAAGACTATCT

ATCCGTGGTCCTGAACCAGTTATGTGTGTTGCATGAGAAAACGCCAGTA

AGTGACAGAGTCACCAAATGCTGCACAGAATCCTTGGTGAACAGGCGAC

CATGCTTTTCAGCTCTGGAAGTCGATGAAACATACGTTCCCAAAGAGTT

TAATGCTGAAACATTCACCTTCCATGCAGATATATGCACACTTTCTGAG

AAGGAGAGACAAATCAAGAAACAAACTGCACTTGTTGAGCTTGTGAAAC

ACAAGCCCAAGGCAACAAAAGAGCAACTGAAAGCTGTTATGGATGATTT

CGCAGCTTTTGTAGAGAAGTGCTGCAAGGCTGACGATAAGGAGACCTGC

TTTGCCGAGGAGGGTAAAAAACTTGTTGCTGCAAGTCAAGCTGCCTTAG

GCTTACCCGGACTTTGTACCCCTAGCAGGGGGCGGCTGGTGCCGCGCGG

CAGCCTTCAACATCATCACCACCATCACGTCGACTAATGGAATTCCCTA
```

The expected ORF product was:

(SEQ ID NO: 126)
```
MKWVTFISLL FLFSSAYSRG VFRRDAHKSE VAHRFKDLGE

ENFKALVLIA FAQYLQQCPF EDHVKLVNEV TEFAKTCVAD

ESAENCDKSL HTLFGDKLCT VATLRETYGE MADCCAKQEP

ERNECFLQHK DDNPNLPRLV RPEVDVMCTA FHDNEETFLK

KYLYEIARRH PYFYAPELLF FAKRYKAAFT ECCQAADKAA

CLLPKLDELR DEGKASSAKQ RLKCASLQKF GERAFKAWAV

ARLSQRFPKA EFAEVSKLVT DLTKVHTECC HGDLLECADD

RADLAKYICE NQDSISSKLK ECCEKPLLEK SHCIAEVEND
```

```
EMPALDLCTP SRATSADFVE SKDVCKNYAE AKDVFLGMFL

YEYARRHPDY SVVLLLRLAK TYETTLEKCC AAADPHECYA

KVFDEFKPLV EEPQNLIKQN CELFEQLGEY KFQNALLVRY

TKKVPQVSTP TLVEVSRNLG KVGSKCCKHP EAKRMPCAED

YLSVVLNQLC VLHEKTPVSD RVTKCCTESL VNRRPCFSAL

EVDETYVPKE FNAETFTFHA DICTLSEKER QIKKQTALVE

LVKHKPKATK EQLKAVMDDF AAFVEKCCKA DDKETCFAEE

GKKLVAASQA ALGLPGLCTP SRGRLVPRGS LQHHHHHHV D
```

Example 7

Production of Drug-HSA Conjugate

Purified HSA modified with aldehyde tags was added to a buffered solution of peptide that has been functionalized with an N-terminus amino-oxy functionality. The conjugation reaction is carried out in a buffered solution at a pH of 6.0 with 100 mM aniline added. A three-fold excess of aminooxy peptide to aldehyde was added to the reaction mixture to drive the reaction to completion. After addition of peptide to a solution of the ald-tagged HSA, the mixture was stirred at room temp for 2 h, dialyzed and the protein-peptide conjugate purified using FPLC.

Example 8

Expression of Aldehyde-Tagged HSA with *Pichia Pastoris*

6×His-LCTPSR-HSA (SEQ ID NO:127) was transformed into the *Pichia* strain GS115 using pRW39 (6×His-LCTPSR-HSA (SEQ ID NO:127) in pPIC3.5K). pRW39 was linearized with BglII. 20 μg of DNA in 10 μL water was added to 80 μL of freshly competent GS115 cells and electroporated in a 2 mm cuvette (2000V). 1 mL of ice cold 1M sorbitol was added immediately after electroporation. The cells were plated on regeneration dextrose Bacto agar plates (lacking histidine to select for HIS+transformants) and incubated 30° C. for 3 days. Colonies were isolated and tested for resistance to G418 to select for those colonies containing multiple copies of aldehyde-tagged-HSA integrated into the *Pichia* genome.

Figure 14:
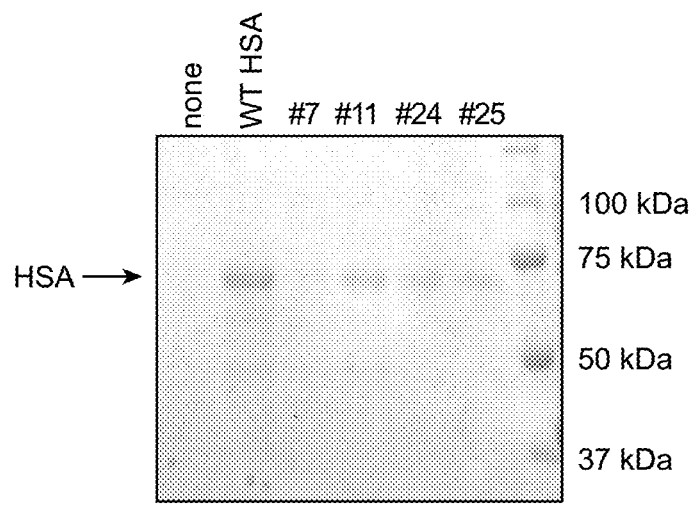
FIG. 14 is a picture of a gel showing Ald tag-HSA was expressed in and secreted from the yeast *Pichia pastoris*. A *Pichia* strain expressing no HSA (none), wild-type HSA (WT HSA), or ald tag-HSA (clones #7, 11, 24, 25) was grown in methanol-containing medium to induce expression of HSA. After 6 days, the media was collected, cleared of cells, run on an SDS-PAGE gel, and stained with Coomassie Blue. proteing gel is a Ald tag-HSA was expressed in and secreted from the yeast *Pichia pastoris*. A *Pichia* strain expressing no HSA (none), wild-type HSA (WT HSA), or ald tag-HSA (clones #7, 11, 24, 25) was grown in methanol-containing medium to induce expression of HSA. After 6 days, the media was collected, cleared of cells, run on an SDS-PAGE gel, and stained with Coomassie Blue.

Colonies were grown 10 mL of buffered buffered glycerol-complex medium overnight at 30° C. Cultures were centrifuged the cells were resuspended in buffered methanol-complex medium to induce expression of 6×His-LCTPSR-HSA (SEO ID NO:127), integrated into the Pichia genome under the control of a methanol-inducible promoter. The cells were grown for 6 days at 30° C. Methanol was added to each culture every 24 h to 0.5%. After 6 days, cells were cleared from the media by centrifugation and 10 uL of the media was run on an SDS-PAGE gel, and the gel was stained with Coomassie Blue. As a negative control, the original untransformed GS115 strain was also grown and taken through the same procedure. As a positive control for methanol induction and secretion of a protein into the media, a GS115 strain containing wild-type HSA integrated into the *Pichia* genome under control of the methanol-inducible promoter was also grown. The colonies expressed aldehyde-tagged-HSA and secreted it into the media (see FIG. 14).

Example 9

Expressing and Purifying Aldehyde-Tagged-HSA from CHO Cells

Figure 15:
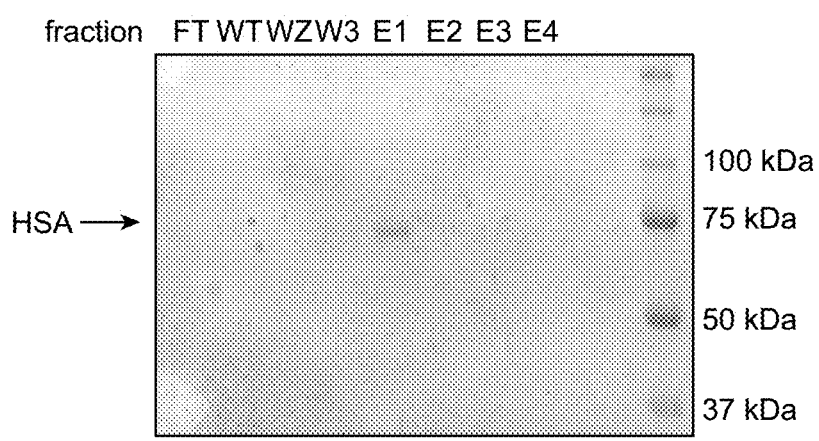
FIG. 15 is a picture of a gel showing aldehyde-tagged-HSA was expressed and secreted from CHO cells. After 72 h, the media was collected, cleared of cells, and purified on Ni-NTA resin. Flow-through (FT), wash (W) and elution (E) fractions were collected, run on an SDS-PAGE gel and stained with Coomassie Blue.

24 µg of a DNA construct containing aldehyde-tagged-HSA in pcDNA3.1 (pRW38) was transfected into CHO-K1 cells in Opti-MEM serum-free medium using Lipofectin transfection reagent in a 10 cm dish. After 5 h at 37° C., the Opti-MEM was removed and Ex-Cell 325 protein-free medium (+1% FBS+L-glut+Pen/Strep) was added. After 72 h at 37°, the media was collected and cleared of debris. 10 mL Binding Buffer (20 mM $Na_2PO_4$, 500 mM NaCl, 20 mM Imidazole, pH 7.5) and 200 µl of Ni-NTA resin was added. After incubating with rotation for 1 h at 4° C., the mixture was added to a column and the flow-through fraction was collected. The resin was washed with 4 mL Binding Buffer and then eluted 5 times with 500 µL Elution Buffer (20 mM $Na_2PO_4$, 500 mM NaCl, 500 mM Imidazole, pH 7.5). 10 µL of the media was run on an SDS-PAGE gel, and the gel was stained with Coomassie Blue (FIG. 15).

That which is claimed is:

1. A method of producing a carrier protein-drug conjugate, the method comprising:
   (a) combining in a reaction mixture:
      (1) an aldehyde-tagged carrier protein comprising a heterologous sulfatase motif, wherein the heterologous sulfatase motif is less than 13 amino acid residues and contains a sequence of the formula:

$X_1Z_1X_2Z_2X_3Z_3$ wherein:
      $Z_1$ is a 2-formylglycine residue;
      $Z_2$ is a proline or alanine residue;
      $X_1$ is present or absent and, when present, is any amino acid,
      wherein $X_1$ is present when the sulfatase motif is at the N-terminus of the polypeptide;
      $X_2$ and $X_3$ are each independently any amino acid; and
      $Z_3$ is a basic amino acid; and
      (2) a drug for conjugation to the carrier protein, wherein the drug comprises a reactive partner for an aldehyde of the carrier protein;
   wherein the drug is provided in the reaction mixture in an amount sufficient to provide for a desired drug to carrier protein ratio, said combining being under conditions suitable to promote reaction between the aldehyde of the carrier protein and the reactive partner of the drug to generate a carrier protein-drug conjugate; and
   (b) isolating the carrier protein-drug conjugate from the reaction mixture; and
   wherein the heterologous sulfatase motif of the carrier protein-drug conjugate contains a sequence of the formula:

$X_1(FGly')X_2Z_2X_3Z_3$ where FGly' is of the formula:

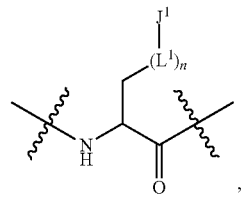

wherein:
      $J^1$ is the drug;
      each $L^1$ is independently selected from alkylene, substituted alkylene, alkenylene, substituted alkenylene, alkynylene, substituted alkynylene, arylene, substituted arylene, cycloalkylene, substituted cycloalkylene, heteroarylene, substituted heteroarylene, heterocyclene, substituted heterocyclene, acyl, amido, acyloxy, urethanylene, thioester, sulfonyl, sulfonamide, sulfonyl ester, O, and NH; and
      n is a number selected from 1 to 40.

2. The method of claim 1, wherein the carrier protein is folded prior to said combining.

3. The method of claim 2, wherein the carrier protein presents the drug on a solvent-accessible surface of the carrier protein-drug conjugate when the carrier protein is folded.

4. The method of claim 1, wherein the carrier protein-drug conjugate comprises two or more heterologous sulfatase motifs.

5. The method of claim 4, wherein the carrier protein-drug conjugate comprises three or more heterologous sulfatase motifs.

6. The method of claim 4, wherein the heterologous sulfatase motifs are positioned in the carrier protein-drug conjugate at at least one of the N-terminus of the carrier protein, the C-terminus of the carrier protein, and a solvent-accessible loop of the carrier protein.

7. The method of claim 4, wherein the two or more heterologous sulfatase motifs are provided as a concatamer and are separated by a flexible linker.

8. The method of claim 1, wherein the carrier protein-drug conjugate has a drug to carrier protein ratio of 2:1 or more.

9. The method of claim 1, wherein the carrier protein-drug conjugate has a drug to carrier protein ratio of 3:1 or more.

10. The method of claim 1, wherein the carrier protein-drug conjugate has a drug to carrier protein ratio of 4:1 or more.

11. The method of claim 1, wherein the carrier protein-drug conjugate has a drug to carrier protein ratio of 5:1 or more.

12. The method of claim 1, wherein the carrier protein is albumin.

13. The method of claim 1, wherein the covalently bound drug is a peptide drug.

14. The method of claim 13, wherein the peptide drug is glucagon-like peptide 1 (GLP-1) or a biologically active variant thereof.

15. The method of claim 13, wherein the peptide drug is calcitonin or a biologically active variant thereof.

16. The method of claim 1, wherein the covalently bound drug is a small molecule drug.

17. The method of claim 1, wherein $Z_3$ is arginine (R).

18. The method of claim 1, wherein $X_1$, when present, is an aliphatic amino acid, a sulfur-containing amino acid, or a polar, uncharged amino acid; and $X_2$, and $X_3$ are each independently an aliphatic amino acid, a sulfur-containing amino acid, or a polar, uncharged amino acid.

19. The method of claim 1, wherein the $X_1$, when present, is L, M, V, S or T.

20. The method of claim 1, wherein $X_2$ and $X_3$ are each independently S, T, A, V, G, or C.

21. The method of claim 1, wherein the heterologous sulfatase motif is less than 12 amino acid residues.

22. The method of claim 1, wherein the heterologous sulfatase motif is less than 11 amino acid residues.

23. The method of claim 1, wherein the heterologous sulfatase motif is less than 10 amino acid residues.

24. The method of claim 1, wherein the heterologous sulfatase motif is less than 9 amino acid residues.

25. The method of claim 1, wherein the heterologous sulfatase motif is less than 8 amino acid residues.

26. The method of claim 1, wherein the heterologous sulfatase motif is less than 7 amino acid residues.

\* \* \* \* \*